(12) United States Patent
Metzger et al.

(10) Patent No.: US 8,071,319 B2
(45) Date of Patent: *Dec. 6, 2011

(54) RAPID MICROBIAL DETECTION AND ANTIMICROBIAL SUSCEPTIBIILITY TESTING

(75) Inventors: Steven W. Metzger, Westminister, CO (US); David C. Howson, Denver, CO (US); David A. Goldberg, Boulder, CO (US); Daniel A. Buttry, Laramie, WY (US)

(73) Assignee: Accelr8 Technology Corporation, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/021,087

(22) Filed: Jan. 28, 2008

(65) Prior Publication Data

US 2008/0241858 A1 Oct. 2, 2008

Related U.S. Application Data

(63) Continuation of application No. 11/303,803, filed on Dec. 16, 2005, now Pat. No. 7,341,841, which is a continuation of application No. 10/888,828, filed on Jul. 8, 2004, now Pat. No. 7,687,239.

(60) Provisional application No. 60/486,605, filed on Jul. 12, 2003, provisional application No. 60/571,479, filed on May 13, 2004, provisional application No. 60/637,423, filed on Dec. 16, 2004, provisional application No. 60/638,989, filed on Dec. 22, 2004.

(51) Int. Cl.
*G01N 33/53* (2006.01)
(52) U.S. Cl. ........................................ 435/7.2
(58) Field of Classification Search .................. None
See application file for complete search history.

(56) References Cited

U.S. PATENT DOCUMENTS

| | | | |
|---|---|---|---|
| 3,493,772 A * | 2/1970 | Burzio et al. ................... 377/10 |
| 3,811,036 A * | 5/1974 | Perry ............................ 377/10 |
| 3,832,532 A * | 8/1974 | Praglin et al. ................ 435/32 |
| 3,935,073 A | 1/1976 | Waters |
| 4,199,449 A | 4/1980 | Slejko |
| 4,199,499 A | 4/1980 | Smithwick, Jr. et al. |
| 4,200,493 A | 4/1980 | Wilkins et al. |
| 4,246,343 A | 1/1981 | Wilkins et al. |
| 4,259,442 A | 3/1981 | Gayral |
| 4,288,543 A * | 9/1981 | Sielaff et al. ................... 435/34 |
| 4,313,734 A | 2/1982 | Leuvering |
| 4,481,137 A | 11/1984 | Ohnishi et al. |
| 4,487,839 A | 12/1984 | Kamentsky |
| 4,508,832 A | 4/1985 | Carter et al. |
| 4,521,522 A | 6/1985 | Lundstrom et al. |
| 4,537,861 A | 8/1985 | Elings et al. |
| 4,716,123 A | 12/1987 | Wood |
| 4,752,567 A | 6/1988 | De Brabander et al. |
| 4,778,758 A | 10/1988 | Ericsson et al. |
| 4,805,623 A | 2/1989 | Jobsis |
| 4,876,208 A | 10/1989 | Gustafson et al. |
| 4,885,077 A | 12/1989 | Karakelle et al. |
| 5,017,009 A | 5/1991 | Schutt et al. |
| 5,079,172 A | 1/1992 | Hari et al. |
| 5,082,630 A | 1/1992 | Partin et al. |
| 5,173,164 A | 12/1992 | Egen et al. |
| 5,196,527 A | 3/1993 | Ookuma et al. |
| 5,240,618 A | 8/1993 | Caldwell et al. |
| 5,288,611 A | 2/1994 | Kohne |
| 5,314,805 A | 5/1994 | Haugland et al. |
| 5,329,461 A | 7/1994 | Allen et al. |
| 5,350,697 A | 9/1994 | Swope et al. |
| 5,405,783 A | 4/1995 | Pirrung et al. |
| 5,466,416 A | 11/1995 | Ghaed et al. |
| 5,488,567 A | 1/1996 | Allen et al. |
| 5,496,701 A | 3/1996 | Pollard-Knight |
| 5,556,764 A | 9/1996 | Sizto et al. |
| 5,599,668 A | 2/1997 | Stimpson et al. |
| 5,604,099 A | 2/1997 | Erlich et al. |
| 5,622,868 A | 4/1997 | Clarke et al. |
| 5,656,432 A | 8/1997 | Claverys et al. |
| 5,792,622 A | 8/1998 | Botsford |
| 5,828,716 A | 10/1998 | Bisconte de Saint Julien |
| 5,843,651 A | 12/1998 | Stimpson et al. |
| 5,849,486 A | 12/1998 | Heller et al. |
| 5,866,345 A | 2/1999 | Wilding et al. |
| 5,872,013 A | 2/1999 | Leunissen et al. |
| 5,993,634 A | 11/1999 | Simpson et al. |
| 6,017,696 A | 1/2000 | Heller |
| 6,043,048 A | 3/2000 | Johnston et al. |
| 6,051,380 A | 4/2000 | Sosnowski et al. |
| 6,054,270 A | 4/2000 | Southern |

(Continued)

FOREIGN PATENT DOCUMENTS

EP 0 498 920 8/1992

(Continued)

OTHER PUBLICATIONS

International Search Report, PCT/US99/10917, Jul. 30, 2001, 6 pages.
International Search Report, PCT/US03/06086, Jun. 27, 2003, 5 pages.
European Search Report, EP 03 716230.2, Oct. 15, 2007, 2 pages.
Beaglehole, "Performance of a Microscopic Imaging Ellipsometer," Rev. Sci. Instrum. 1988, 59 (12), pp. 2557-2559.
Benecky et al., "Simultaneous Detection of Multiple Analytes Using Copalis Technology: A Reduction to Practice," Clin. Chem. 1998, 44(9), pp. 2052-2054.
De Brabander et al., "Detection of Gold Probes With Video-Enhanced Contrast Microscopy: Nanovid Microscopy," Amer. J. Anatomy 1989, 185, pp. 282-295.

(Continued)

*Primary Examiner* — Ann Lam
(74) *Attorney, Agent, or Firm* — Dorsey & Whitney LLP

(57) ABSTRACT

A method for the detection of microorganisms in a sample comprising contacting said sample with a biosensor concentration module, allowing microorganisms to grow for a first period of time and detecting growth of discrete microorganisms as an indication of the presence of said microorganisms.

7 Claims, 17 Drawing Sheets

U.S. PATENT DOCUMENTS

| | | | |
|---|---|---|---|
| 6,099,803 | A | 8/2000 | Ackley et al. |
| 6,101,946 | A | 8/2000 | Martinsky |
| 6,136,171 | A | 10/2000 | Frazier et al. |
| 6,143,247 | A | 11/2000 | Sheppard, Jr. et al. |
| 6,153,416 | A | 11/2000 | Yuan |
| 6,176,620 | B1 | 1/2001 | Obara |
| 6,214,560 | B1 | 4/2001 | Yguerabide et al. |
| 6,245,508 | B1 | 6/2001 | Heller et al. |
| 6,251,615 | B1 | 6/2001 | Oberhardt |
| 6,264,825 | B1 | 7/2001 | Blackburn et al. |
| 6,270,953 | B1 | 8/2001 | Malcus-Vocanson et al. |
| 6,290,839 | B1 | 9/2001 | Kayyem et al. |
| 6,379,897 | B1 | 4/2002 | Weidenhammer et al. |
| 6,391,546 | B1 | 5/2002 | Karube et al. |
| 6,391,577 | B1 | 5/2002 | Mikkelsen et al. |
| 6,403,367 | B1 | 6/2002 | Cheng et al. |
| 6,472,166 | B1 | 10/2002 | Wardlaw et al. |
| 6,472,228 | B2 | 10/2002 | Wang et al. |
| 6,548,263 | B1 | 4/2003 | Kapur et al. |
| 6,551,841 | B1 | 4/2003 | Wilding et al. |
| 6,605,453 | B2 | 6/2003 | Graves et al. |
| 6,611,765 | B2 | 8/2003 | Boeufgras et al. |
| 6,716,620 | B2 | 4/2004 | Bashir et al. |
| 6,809,862 | B2 | 10/2004 | Behnsen et al. |
| 6,841,379 | B2 | 1/2005 | Matson |
| 6,844,028 | B2 | 1/2005 | Mao et al. |
| 7,108,775 | B2 | 9/2006 | Bahatt et al. |
| 7,258,837 | B2 | 8/2007 | Yager et al. |
| 7,306,924 | B2 | 12/2007 | Gomez et al. |
| 7,341,841 | B2 * | 3/2008 | Metzger et al. ............... 435/7.2 |
| 7,435,579 | B2 | 10/2008 | Bashir et al. |
| 7,687,239 | B2 * | 3/2010 | Goldberg et al. ............. 435/7.2 |
| 2001/0009774 | A1 | 7/2001 | Shin et al. |
| 2001/0053535 | A1 | 12/2001 | Bashir et al. |
| 2002/0028519 | A1 * | 3/2002 | Yguerabide et al. .......... 436/518 |
| 2002/0119455 | A1 | 8/2002 | Chan |
| 2002/0155490 | A1 | 10/2002 | Skinner et al. |
| 2003/0036054 | A1 | 2/2003 | Ladisch |
| 2003/0119028 | A1 | 6/2003 | Graves et al. |
| 2003/0124623 | A1 * | 7/2003 | Yager et al. ................... 435/7.5 |
| 2003/0153023 | A1 | 8/2003 | Starzl et al. |
| 2003/0157587 | A1 | 8/2003 | Gomez et al. |
| 2003/0170613 | A1 * | 9/2003 | Straus .............................. 435/5 |
| 2003/0186341 | A1 | 10/2003 | Kuhn et al. |
| 2004/0089546 | A1 | 5/2004 | Bahatt et al. |
| 2004/0189311 | A1 | 9/2004 | Glezer et al. |
| 2005/0048599 | A1 | 3/2005 | Goldberg et al. |
| 2005/0112544 | A1 | 5/2005 | Xu et al. |
| 2007/0037225 | A1 | 2/2007 | Metzger et al. |
| 2007/0298513 | A1 | 12/2007 | Starzl et al. |
| 2010/0048428 | A1 * | 2/2010 | Coyer et al. .................... 506/32 |

FOREIGN PATENT DOCUMENTS

| | | | |
|---|---|---|---|
| GB | 1520733 | | 8/1978 |
| JP | 2002-330799 | | 11/2002 |
| WO | WO 90/11525 | | 10/1990 |
| WO | WO 94/02831 | | 2/1994 |
| WO | WO 95/28641 | | 10/1995 |
| WO | 96/14431 | A1 | 5/1996 |
| WO | WO 98/22808 | | 5/1998 |
| WO | WO 99/20789 | | 4/1999 |
| WO | WO 99/58948 | | 11/1999 |
| WO | WO 00/024941 | | 5/2000 |
| WO | 02/38724 | A2 | 5/2002 |
| WO | WO 03022999 | * | 10/2002 |
| WO | WO 03/022999 | | 3/2003 |
| WO | 03/065009 | A2 | 8/2003 |
| WO | WO 03/073100 | | 9/2003 |

OTHER PUBLICATIONS

Elghanian et al., "Selective Colorimetric Detection of Pooynucleotides Based on the Distance-Dependent Optical Properties of Gold Nanoparticles," Science 1997, 277, pp. 1078-1081.

Gao et al., "Epipolarization Microscopic Immunogold Assay: A Combination of Immunogold Silver Staining, ELISA and Epipolarization Microscopy," Biotech. & Histochem., 1995, 70(4), pp. 211-216.

Geerts et al., "Nanovid Microscopy," Nature 1991, vol. 351, pp. 765-766.

Jin et al., A Biosensor Concept Based on Imaging Ellipsometry for Visualization of Biomolecular Interactions, Anal. Biochem. 1995, 232, pp. 69-72.

Kubitschko et al., Refractometric Immunosens Only, "Sensitivity Enhancement of Optical Immunosensors with Nanoparticles," Analytical Biochem. 1997, 253, pp. 112-122.

Okano et al., "Using Microparticle Labeling and Counting for Attomole-Level Detection in Heterogeneous Immunoassay," Analytical Biochem., 1992, 202, pp. 120-125.

Salmon et al., "Video-Enhanced Differential Interference Contrast Light Microscopy," BioTechniques, 1989, 7(6), pp. 624-633.

Stimpson et al., "Real-Time Detection of DNA Hybridization and Melting on Oligonucleotide Arrays by Using Optical Wave Guides," Genetics, Proc. Natl. Acad. Sci. USA, vol. 92, Jul. 1995, pp. 6379-6383.

Taton et al., "Two-Color Labeling of Oligonucleotide Arrays via Size-Selective Scattering of Nanoparticle Probes," J. Am. Chem. Soc. 2001, 123, pp. 5164-5165.

Vener et al., "A Novel Approach to Nonradioactive Hybridization Assay of Nucleic Acids Using Stained Latex Particles," Analytical Biochem. 1991, 198, pp. 308-311.

Rabinovitch et al., "Removal and Inactivation of *Staphylococcus epidermidis* Biofilms by Electrolysis," Applied and Environmental Microbiology, 2006, 72, pp. 6364-6366.

Van der Borden et al., "Electric Current-Induced Detachment of *Staphylococcus epidermidis* Biofilms from Surgical Stainless Steel," Applied and Environmental Microbiology, 2004, 70, pp. 6871-6874.

Ateya, D.A., Sachs, F., Gottlieb, P.A., Besch, S., and Hua, S.Z. (2005) Volume cytometry: microfluidic sensor for high-throughput screening in real time. Anal Chem 77, 1290-4.

Bae, Y.M., Oh, B.K., Lee, W., Lee, W.H., and Choi, J.W. (2004) Immunosensor for detection of *Yersinia enterocolitica* based on imaging ellipsometry. Anal Chem 76, 1799-803.

Balaban, N.Q., Merrin, J., Chait, R., Kowalik, L., and Leibler, S. (2004) Bacterial persistence as a phenotypic switch. Science 305, 1622-5.

Barton, A.J., Sagers, R.D., and Pitt, W.G. (1996) Measurement of bacterial growth rates on polymers. J Biomed Mater Res 32, 271-8.

Bridson, E.Y., and Gould, G.W. (2000) Quantal Microbiology. Lett. Appl. Microbiology 30, 95-98.

Cabrera, C.R., and Yager, P. (2001) Continuous concentration of bacteria in a microfluidic flow cell using electrokinetic techniques. Electrophoresis 22, 355-62.

Dai, J., Ito, T., Sun, L., and Crooks, R.M. (2003) Electrokinetic trapping and concentration enrichment of DNA in a microfluidic channel. J. Am. Chem. Soc. 125,13026-27.

Delehanty, J.B., and Ligler, F.S. (2002) A microarray immunoassay for simultaneous detection of proteins and bacteria. Anal Chem 74, 5681-7.

Desai, M.J., and Armstrong, D.W. (2003) Separation, Identification, and Characterization of Microorganisms by Capillary Electrophoresis. Microbiology and Molecular Biology Reviews, 38-51.

Elfwing, A., LeMarc, Y., Baranyi, J., and Ballagi, A. (2004) Observing growth and division of large numbers of individual bacteria by image analysis. Appl Environ Microbiol 70, 675-8.

Ertl, P., and Mikkelsen, S.R. (2001) Electrochemical biosensor array for the identification of microorganisms based on lectin-lipopolysaccharide recognition. Anal Chem 73, 4241-8.

Ertl, P., Wagner, M., Corton, E., and Mikkelsen, S.R. (2003) Rapid identification of viable *Escherichia coli* susbpecies with electrochemical screen-printed biosensor array. Biosens Bioelectron 18, 907-16.

Forero, M.G., Cristobal, G., and Alvarez-Borrego (2003) in "Applications of Digital Image Processing XXVI" (Tescher, A.G., Ed.), vol. 5203, pp. 71-81, SPIE.

Friedman, N., Vardi, S., Ronen, M., Alon, U., and Stavans, J. (2005) Precise Temporal Modulation in the Response of the SOS DNA Repair Network in Individual Bacteria. PLoS Biol 3, e238, pp. 1261-1263.

Geesey, G.G., and White, D.C. (1990) Determination of bacterial growth and activity at solid-liquid interfaces. Annu Rev Microbial 44, 579-602.

Huang, T., Geng, T., Sturgis, J., Haibo, L., Gomez, R., Bashir, R., Bhunia, A.K., Robinson, J.P., and Ladisch, M. (2003) Lysozyme for capture of microorganisms on protein biochips. Enzyme and Microbial Technol 33, 958-66.

Huang, Y., Ewalt, K.L., Tirado, M., Haigis, R., Forster, A., Ackley, D., Heller, M.J., O'Connel, J.P., and Krihak, M. (2001) Electric Manipulation of Bioparticles and Macromolecules on Microfabricated Electrodes. Anal Chem 73, 1549-59.

Ji, J., Schanzle, J.A., and Tabacco, M.B. (2004) Real-time detection of bacterial contamination in dynamic aqueous environments using optical sensors. Anal Chem 76, 1411-8.

Koh, C.G., Tan, W., Zhao, M.Q., Ricco, A.J., and Fan, Z.H. (2003) Integrating polymerase chain reaction, valving, and electrophoresis in a plastic device for bacterial detection. Anal Chem 75, 4591-8.

Lagally, E.T., Scherer, J.R., Blazej, R.G., Toriello, N.M., Diep, B.A., Ramchandani, M., Sensabaugh, G.F., Riley, L.W., and Mathies, R.A. (2004) Integrated portable genetic analysis microsystem for pathogen/infectious disease detection. Anal Chem 76, 3162-70.

Lawrence, J.R., et al., "Computer-enhanced darkfield microscopy for the quantitative analysis of bacterial growth and behavior on surfaces." J. Microbial. Methods 10:123-138, (1989).

Lloyd, D., and Hayes, A.J. (1995) Vigour, vitality and viability of microorganisms. FEMS Microbio Lett 133, 1-7.

Maeyama, R., Mizunoe, Y., Anderson, J.M., Tanaka, M., and Matsuda, T. (2004) Confocal imaging of biofilm formation process using fluoroprobed *Escherichia coli* and fluoro-stained exopolysaccharide. J Biomed Mater Res A 70, 274-82.

Markx, G.H. et al., "Dielectrophoretic characterization and separation of micro-organisms" Microbiology, 140, 585-591 (1994).

Markx, G.H. et al., Dielectrophoretic Separation of Cells: Continuous Separation:, Biotechnol. Bioeng. 45, 337-343 (1995).

Meinders, J.M., Van der Mei, H.C., and Busscher, H.J. (1992) In situ enumeration of bacterial adhesion in a parallel plate flow chamber—elimination or in focus flowing bacteria from the analysis. J Microbiol Methods 16, 119-24.

Miller, C., Thomsen, L.E., Gaggero, C., Mosseri, R., Ingmer, H., and Cohen, S.N. (2004) SOS response induction by beta-lactams and bacterial defense against antibiotic lethality. Science 305, 1629-31.

Mueller, M., de la Pena, A., and Derendorf, H. (2004) Issues in pharmacokinetics and pharmacodynamics of anti-infective agents: kill curves versus MIC. Antimicrob Agents Chemother 48, 369-77.

Ozkan, M., Pisanic, T., Scheel, J., Barlow, C., Esener, S.C., and Bhatia, S.N. (2003) Electro-Optical Platform for the Manipulation of Live Cells. Langmuir 19, 1532-38.

Plowman, "Planar integrated optical methods for examining thin films and their surface alayers," Biomaterials, 1998, 19, pp. 341-355.

Rosch, P., Harz, M., Schmitt, M., Peschke, K.D., Ronneberger, 0., Burkhardt, H., Motzkus, H.W., Lankers, M., Hofer, S., Thiele, H., and Popp, J. (2005) Chemotaxonomic identification of single bacteria by micro-Raman spectroscopy: application to clean-room-relevant biological contaminations. Appl Environ Microbiol 71, 1626-37.

Rowe, C.A., Tender, L.M., Feldstein, M.J., Golden, J.P., Scruggs, S.B., MacCraith, B.D., Cras, J.J., and Ligler, F.S. (1999) Array biosensor for simultaneous identification of bacterial, viral, and protein analytes. Anal Chem 71, 3846-52.

Sapsford, K.E., Rasooly, A., Taitt, C.R., and Ligler, F.S. (2004) Detection of *Campylobacter* and *Shigella* species in food samples using an array biosensor. Anal Chem 76, 433-40.

Stewart, E.J., Madden, R., Paul, G., and Taddei, F. (2005) Aging and death in an organism that reproduces by morphologically symmetric division. PLoS Biol 3, e45.

Tison, D.L. (1990) Culture confirmation of *Escherichia coli* serotype 0157:H7 by direct immunofluorescence. J Clin Microbiol 28, 612-3.

Weeratna et al., "Gene Expression Profiling: From Microarrays to Medicine", J. Cini. Immunol. 24:213 (2004).

Wit, P., and Busscher, H.J. (1998) Application of an artificial neural network in the enumeration of yeasts and bacteria adhering to solid substrata. J Microbiol Methods 32, 281-90.

Gast et al., "Detection of Salmonella entertidis in Incubated Pools of Egg Contents by Fluorescence Polarization and Lateral Flow Immunodiffusion", Poultry Science, 82, 2003, pp. 687-690.

Sippy et al., "Rapid electrochemical detection and identification of catalase positive micro-organisms", Biosensors & Bioelectronics, 18, 2003, pp. 741-749, Available online @ www.sciencedirect.com.

\* cited by examiner

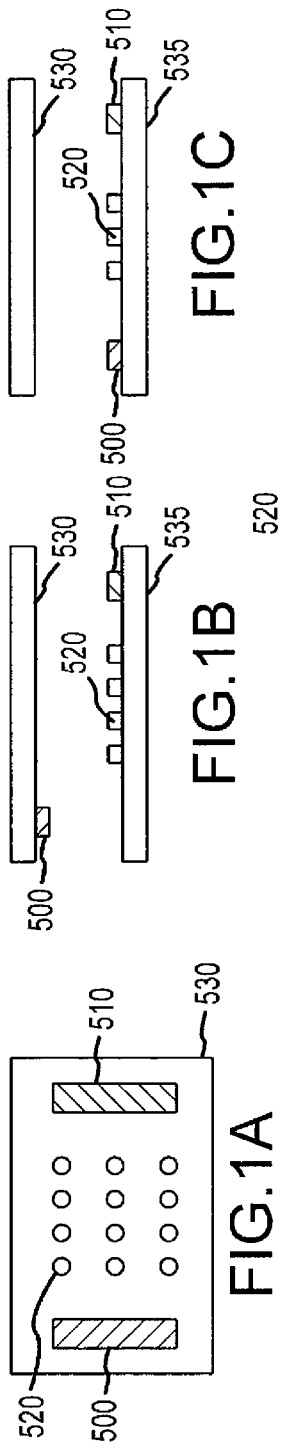
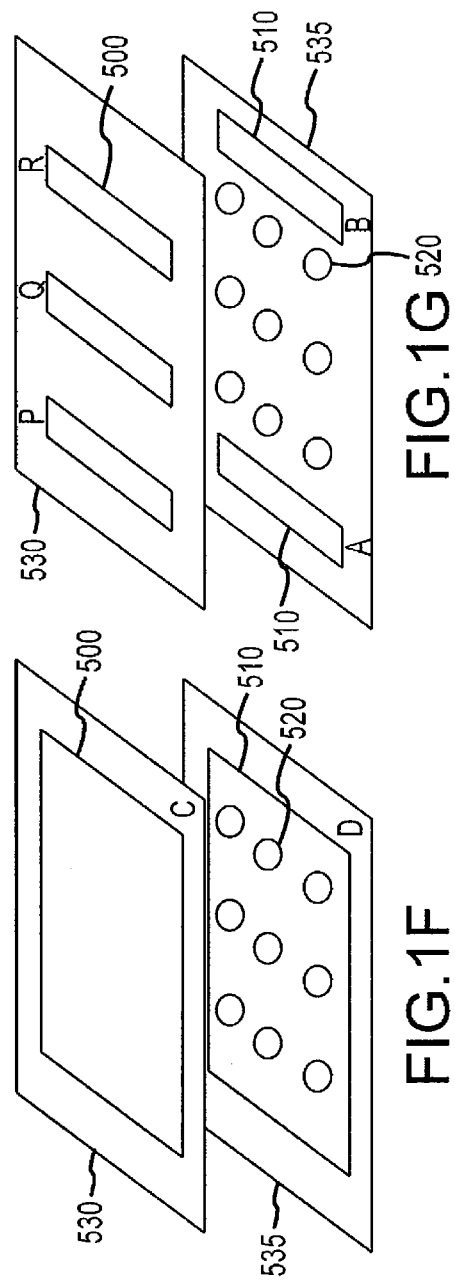

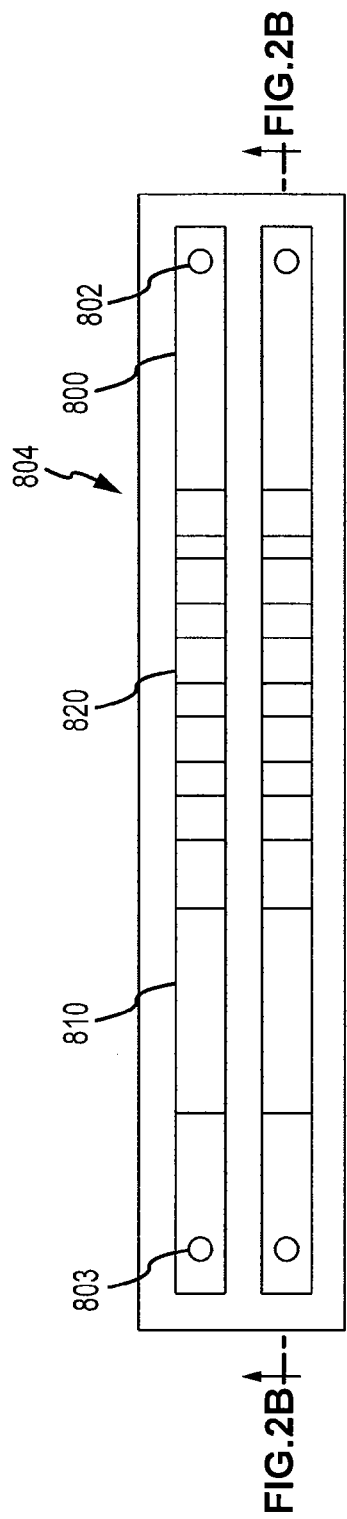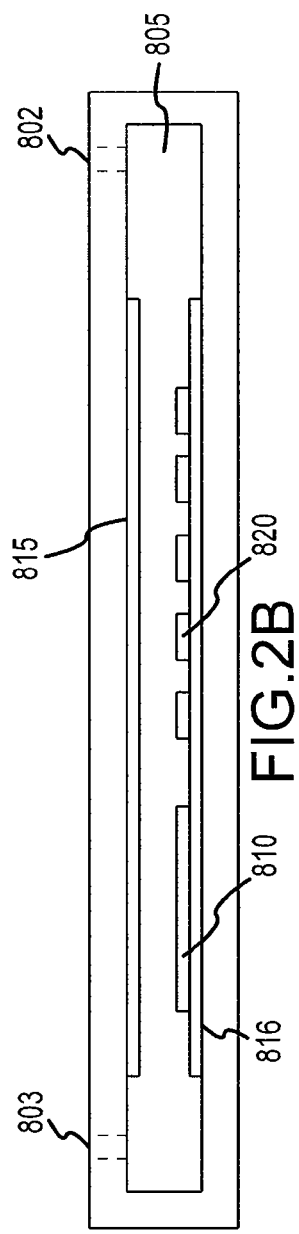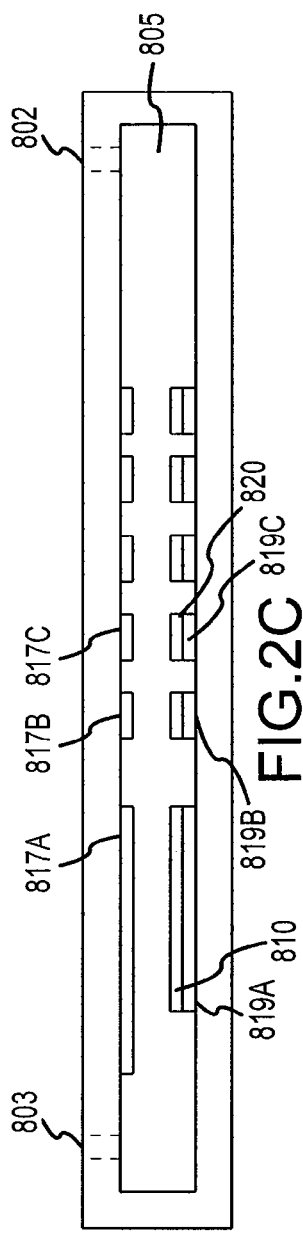

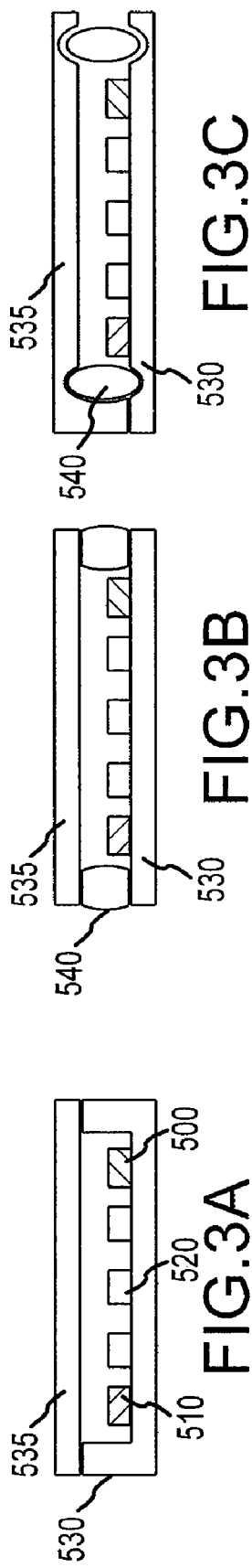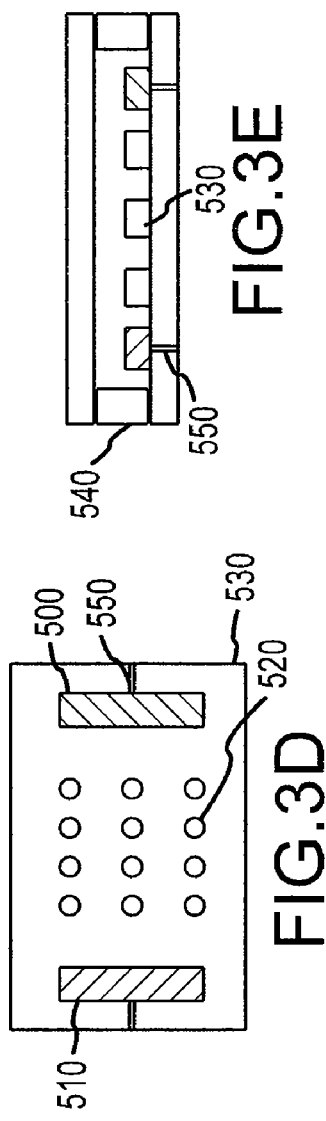

RAPID MICROBIAL DETECTION AND ANTIMICROBIAL SUSCEPTIBIILITY TESTING

CROSS REFERENCE TO OTHER APPLICATIONS

This application is a Continuation of U.S. application Ser. No. 11/303,803, filed Dec. 16, 2005, now U.S. Pat. No. 7,341, 841 which application claims the benefit under 35 U.S.C. 119(e) of U.S. Application Ser. No. 60/637,423, filed Dec. 16, 2004, and U.S. Application Ser. No. 60/638,989, filed Dec. 22, 2004; and U.S. patent application Ser. No. 11/303,803 is a Continuation-In-Part of U.S. application Ser. No. 10/888, 828, filed Jul. 8, 2004 now U.S. Pat. No. 7,687,239 which claims the benefit under 35 U.S.C. 119(e) of U.S. Application Ser. No. 60/486,605, filed Jul. 12, 2003 and U.S. Application Ser. No. 60/571,479, filed May 13, 2004; all of which are incorporated by reference herein in their entirety.

BACKGROUND OF THE INVENTION

The medical outcomes of treating human infections (e.g. ventilator acquired pneumonia, infectious meningitis, bacteremia, and the like) can be significantly affected by the length of time required to perform analysis of the quantity and the identity of bacteria and the susceptibility of the bacteria to various antibiotics. Conventionally, the time for analysis can be 24 to 48 hours or more, during which time-the condition of the patient can deteriorate as the bacteria multiply (see, for example, U.S. Pat. No. 4,778,758 to Ericsson et al., U.S. Pat. No. 3,935,073 to Waters, U.S. Pat. No. 6,043,048 to Johnston et al., and U.S. Pat. No. 4,259,442 to Gayral). Contemporary microbial analysis starts with growth of bacteria from a clinical specimen, such as sputum, blood, and the like, to high concentration in culture medium, typically on the order of 100 million organisms per milliliter. Clinical specimens may contain only a few individual organisms (e.g. in testing blood for bacteremia), and diagnostic thresholds even for high-concentration specimens are typically several thousand-fold lower than quantitative culturing detection limits.

After achieving initial bulk growth up to an adequate working concentration, the operator then performs one or more biochemical tests or growth on selective media that incorporate selective biochemical reagents. Thus the standardized current procedures require at least two sequential growth cycles, each typically requiring many hours to complete.

Additionally, drug susceptibility testing requires determination of failure to grow in selective media. Proof of the absence of growth requires additional time in culture over that which might be required of a direct indicator of cell death. It is well recognized in the medical community that in certain circumstances such methods, which attempt to prove the absence of growth, produce results that do not correlate adequately with the actual results of treatment.

As a result of these and other serious deficiencies, contemporary practice fails to provide the attending physician with the specific diagnostic information that the physician needs in order to select an effective drug to treat the infection within the desired time window. For example, in ventilator-associated pneumonia, clinical research has demonstrated that the odds ratio for increased morbidity and mortality after 24 hours of ineffective treatment remains at 7:1 despite a change to effective treatment. That is, unless the physician initiates effective treatment, i.e. antimicrobial drugs of a type and concentration adequate to quickly kill the infectious organisms within substantially less than 24 hours from symptom onset, a change from ineffective to effective therapy will not significantly improve outcomes for approximately 87% of patients so treated.

Physicians are well aware of the risk of delay, and so prescribe treatment typically using a combination of broad-spectrum drugs selected empirically, based on a particular hospital or community history of microbial drug resistance or susceptibility. Clinical research has demonstrated that such empiric drug treatment is ineffective in approximately 25% to 50% of cases. Additionally, exposure of a patient to inadequate therapy not only increases the individual patient's costs and medical risks, but also increases the likelihood of fostering the emergence of resistant organisms. The latter problem increases the medical risk not only for the individual patient, but for all other individuals in the hospital and community who may later become infected with resistant organisms.

It is well recognized in the clinical research literature that prior exposure of a patient to ineffective antibiotics constitutes a significant risk factor in the later emergence of resistant organisms in that patient. For these and other reasons, it is desirable within the medical community to devise diagnostic methods that do not suffer the deficiencies of delay and inaccuracy that characterize current practices.

In theory, alternatives to microbial growth culturing include direct microbial analytical methods such as immunoassays of various kinds. Antibodies against various microbes are commercially available or may be readily developed. In fact, many different types of immunoassay are now routinely used in certain aspects of diagnosis for microbial infection. However, none yet exist for routine bacterial identification, quantitation, and drug susceptibility testing for many serious infectious diseases.

Similarly, the rapid detection of various microbes such as bacteria, viruses, molds, and the like are also desirable for testing contamination in food and water, and in detecting the presence of potential biological warfare agents. In the food industry many products are commercially available for detecting microbial contaminants. In certain circumstances, some of these provide results in approximately 24 hours for a limited set of particular organisms. However all commercial products still require sample enrichment by means of bacterial culturing before applying the tests.

In the research literature concerning defense for biological warfare, many rapid detection devices have also been described, including some that provide results in one hour or even less. Furthermore, some such devices do not require growth cultures before being used.

However, the sensitivity of devices so far described in the literature for food testing or bio-defense falls far short of the requirements for medical diagnostics. Furthermore, these non-diagnostic applications do not require drug susceptibility testing and so the aforesaid devices do not provide it nor apparently do they lend themselves to adaptation for such a purpose.

A key limitation with these devices and with laboratory methods such as ELISA is their dependency on the target analyte concentration. They rely on passive diffusion of target to an immuno-capture or other detection surface. The rate of occurrence of intimate probe-to-target proximity events, and hence the detection reaction rate, depends on analyte concentration in the sample solution or suspension. This problem is exacerbated by the very low diffusion rates of bacteria.

In order to increase sensitivity with these devices, it is necessary to substantially increase analyte concentration. Researchers have described several stratagems to increase target analyte concentration and also speed the response time for analysis of various bio-molecular and microbial targets. For example, the electrophoresis of target to the probe has been described before by Nanogen, Inc. of San Diego, Calif. (e.g. U.S. Pat. No. 5,849,486 to Heller, U.S. Pat. No. 6,017,696 to Heller, U.S. Pat. No. 6,051,380 to Sosnowski et al., U.S. Pat. No. 6,099,803 to Ackley et al., U.S. Pat. No. 6,245,508 to Heller et al., and U.S. Pat. No. 6,379,897 to Weidenhammer et al.). These systems and methods describe an addressable array of electrodes to which individual probes are attached at each individual electrode, and then which are sequentially and very rapidly reacted with probes. The reported increase in speed of reaction between the target and probes is hundreds or thousands fold. These systems, however, suffer from a number of limitations, including the need to sequentially immobilize probes on the addressable electrodes, the need to perform sequential reactions, and limitations on the detection methods that can be employed due to the higher voltages that are required for electrophoresis, precluding the use of transparent electrodes (e.g. through the use of indium tin oxide), that cannot operate at the voltages used by the Nanogen system. Furthermore, the higher voltages at which the Nanogen system operate generate oxidation products that are potentially harmful to the probes or targets, and which therefore requires the use of complex passivation surfaces to protect the probes and targets. Systems that could make use of high-speed microarray printing, which did not require complex passivation surfaces, and which did not require the electronic and other control necessary for addressable electrodes would greatly reduce the expense and complexity of such systems.

With regards to the use of immobilized probes for the detection of bacteria or other microorganisms, it is also of use to determine the antimicrobial activity of different therapeutic agents, such as antibiotics. There has been a profusion of systems that use nucleic acid or antibody probes to determine the identity of bacteria in a sample (e.g. U.S. Pat. No. 5,656,432 to Clayerys et al. and U.S. Pat. No. 6,403,367 to Cheng et al.). It is difficult with these systems to determine susceptibility to antimicrobial agents, given the difficulty of finding nucleic acid or antibody markers that reliably correlate with antimicrobial resistance or behavior. It is to the solution of these and other problems that the present invention is directed.

BRIEF DESCRIPTION OF THE DRAWINGS

FIGS. 1A-1L depict a variety of electrophoretic configurations with first and second electrophoresis electrodes 500 and 510, detection surfaces 520, first and second substrates 530 and 535 that form one or more detection chambers (not shown).

FIGS. 2A-2D depict a variety of schematics of possible biosensor cartridges. FIG. 2A is a top schematic diagram of a bacterial detection cell 804, and FIG. 2B is a side view schematic diagram of the bacterial detection cell of FIG. 32A through the cross-section X. The cell 804 comprises two chambers 805 (also depicted herein as microchannels 700), of which there can be as few as one and tens or even hundreds. Each chamber will be used either to handle a different bacterial sample, or to handle side-by-side a single sample, in which the bacteria will be treated with different growth media, antibiotics or other anti-organism agents, antibiotic concentration profiles, temperatures, or other physical, chemical or biological conditions to which the bacteria will be subjected. The chambers 805 are shown as enclosed on all sides, but it is consistent with the present invention for the chamber to be open, such as in a format of a microtiter plate well. If the chamber 805 is closed, an input port 803 and an output port 802 are provided for changing the solution within the chamber 805. FIG. 2C is a side view schematic diagram of the bacterial detection cell of FIG. 2B with the use of addressable electrodes. FIGS. 2A, 2B and 2C all depict an optional "preconcentration" area 810, which can have it's own electrode 819A or not (FIG. 2B). Inlet and/or outlet ports 802 are also depicted. FIG. 2D also depicts another embodiment, utilizing a single reference electrode and several working electrodes, one 500 underlying the preconcentration capture surface 810 and one 501 underlying a plurality of detection surfaces 520, although one detection surface can also be used. In general, interconnects are not shown.

FIGS. 3A-3F similarly depict the views of a variety of additional potential biosensor cartridges; FIG. 3A utilizes a first substrate with a depression such that the chambers are formed when the second substrate is added to the top; FIGS. 3B and 3C utilize a gasket 540 between the two substrates. FIGS. 3D, 3E and 3F depict several configurations of electrophoresis configurations, as well as electrical interconnects 550, either on the surface of the first substrate (FIG. 3D, only first "bottom" substrate shown) or through the first substrate (FIG. 3E). Inlet and/or outlet ports are not depicted.

FIGS. 4A and 4D depict multichannel biosensor cartridges. Note that the different sample modules (600 et seq.) can be connected individually to the microchannels, for example when a first microchannel is to evaluate a first antimicrobial agent and a second microchannel is to evaluate a second agent, or when different samples are to be tested in different microchannels. In addition or alternatively, some sample modules may be connected to all channels, for example when a single sample is to be evaluated on all the channels or for common reagents. FIGS. 4A and 4B depict the 8 channel device used in the examples. In this case there are fluidic channels for moving fluid (705) as distinct from fluidic channels 700 containing the detection surface 520. Note the electrophoresis electrodes and their interconnects are not shown, nor are the sample and reagent inlets.

Figure 1H:
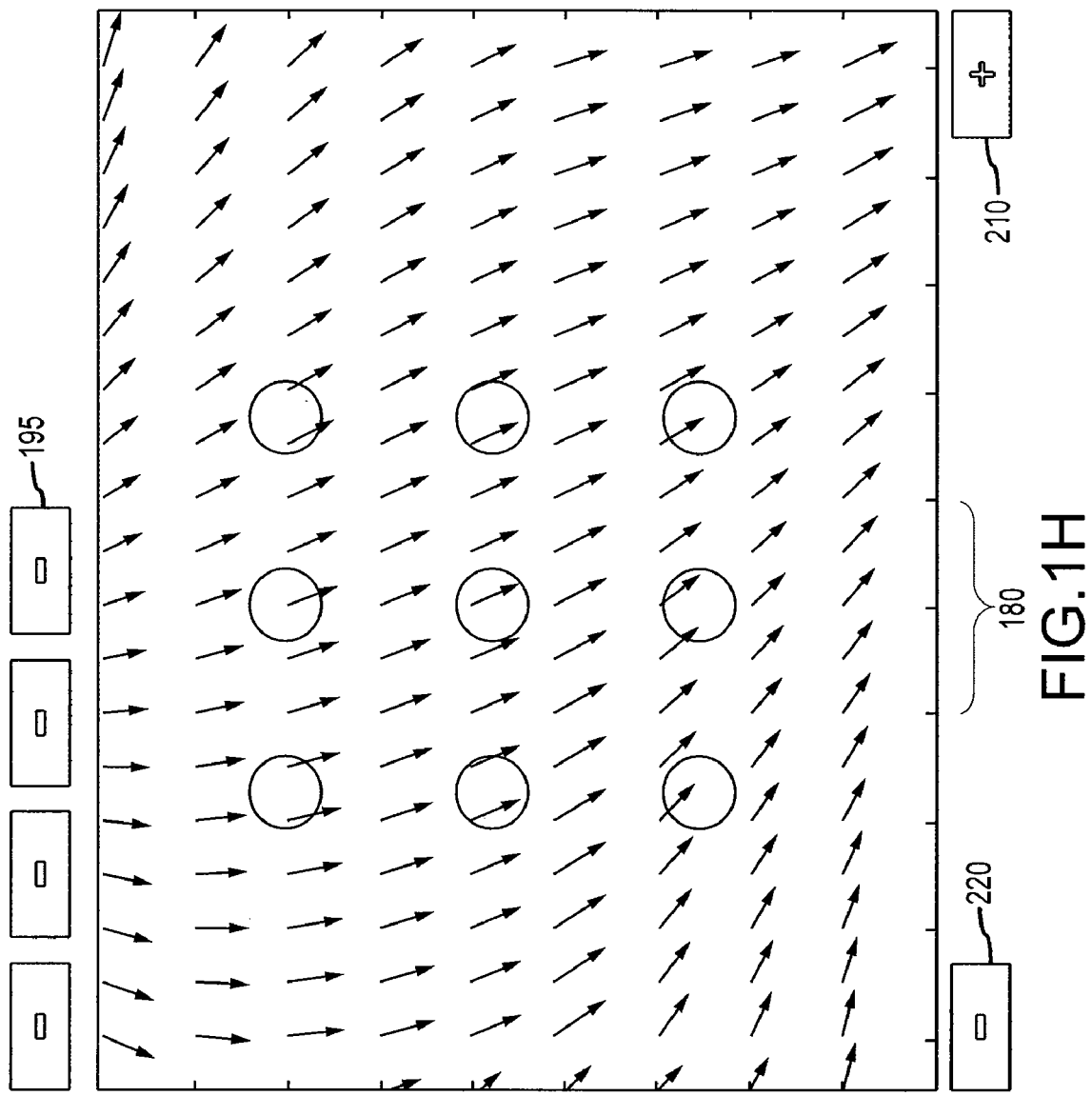

In addition, all figures from U.S. application Ser. No. 10/888,828 and the accompanying legends and text are hereby expressly incorporated by reference.

SUMMARY OF THE INVENTION

The present invention is directed to a variety of compositions and methods for the detection, identification and characterization of microorganisms.

In a first aspect, the invention provides methods for the detection of microorganisms in a sample comprising contacting the sample with a biosensor cartridge. The biosensor comprises a concentration module and at least one detection surface. The microorganisms are concentrated onto the detection surface in such a manner as to result in a plurality of the microorganisms binding to the detection surface in spatially discrete sites. The microorganisms are allowed to grow for a first period of time and then growth is detected as an indication of the presence of the microorganisms.

In an additional aspect, the method further comprises adding at least one bioactive agent (particularly antimicrobial agents) during the growth conditions and optionally taking a number of growth readings or evaluations. A plurality of agents are optionally added, either sequentially or simultaneously, or to aliquots of the sample.

In a further aspect, the invention provides concentration modules utilizing a method selected from the group consisting of electrophoresis, centrifugation, filtration and dielectrophoresis.

In an additional aspect, the detection surface can comprises either a plurality of individual detection sites or a single site. The detection surface(s) can optionally comprise selective capture ligands, or a nonspecific surface.

In a further aspect, growth is detected by monitoring alterations in the physical area on the surface associated with an individual microorganism as it grows. In some embodiments, detecting is done by detecting the presence of daughter cells at the spatially discrete sites. Some aspects include the use of labels.

In an additional aspect, the biosensor cartridge comprises a plurality of channels, each comprising a detection surface. Optionally, the biosensor further comprises a plurality of storage modules.

In a further aspect, the invention provides methods of diagnosing a microbial infection in a patient comprising providing a matrix of time versus kill curves for a panel of antimicrobial agents against a panel of microorganisms, and contacting a sample from the patient with a biosensor. The patient microorganisms are monitored for growth in the presence of the panel of antimicrobial agents and at least one of the patient microorganisms is identified by comparing its growth to the matrix.

In an additional aspect, the invention provides methods of screening for an antimicrobial agent of at least one microorganism comprising contacting the microorganism with a biosensor as outlined herein, concentrating the microorganisms, adding at least one candidate antimicrobial agent, and detecting alterations in the growth of discrete microorganisms as compared to the absence of the candidate agent.

In a further aspect, the methods of the invention are directed to determining the concentration dependence of a growth inhibitory agent on a sample of microorganisms. The method comprises immobilizing individual microorganisms in discrete locations on a substrate and incubating the microorganisms and lineal descendants in the presence of the agent. The amount of microorganisms are determined at intervals, and the kinetics of growth inhibition is related to the concentration dependence of the agent.

In an additional aspect, the methods are directed to determining the resistance to a growth inhibitory agent on a sample of microorganisms. The method comprises immobilizing a multiplicity of individual microorganisms in discrete locations on a substrate and incubating. The amount of microorganisms is analyzed at intervals at each location, thereby indicating the effect of the agent on each microorganism and its descendants, and the individual effects are summed.

DETAILED DESCRIPTION OF THE INVENTION

The present invention is based on the use of a new form of microbial detection analysis, termed herein "quantum microbiology" (sometimes referred to herein as "QM"). Standard quantitative microbiological analyses rely on "colony forming units", or "CFUs", a term which refers to whatever produces a visually detectable microbial colony on a nutrient agar plate. That is, the traditional "quantum" is a visible colony of microorganisms on an agar plate. QM, however, allows the quantification and/or qualification of microorganisms on a single cell basis (e.g., the "quantum" in this case is a single cell, or a clonal population from a single cell). This has a number of profound advantages, including the fact that the individual doubling time of a single cell of the type of interest in diagnosis is generally 20-60 minutes, rather than the 12 to 48 hours generally required using current techniques to visualize changes in CFUs, making methods based on the present techniques far more rapid, a significant advantage in life-threatening microbial infections. Thus, the techniques of the invention are sometimes referred to herein as kinetic techniques, which allow rate analyses using repeated measurements of the same cells over time. Additionally, the present methods allow for high redundancy of the diagnostic call, in that each of the cells within the clones formed from the individual cells provides quantitative and/or qualitative information. For example, each daughter and grand-daughter cell can be assigned an identity and relatedness based on the factors outlined herein, and thus statistically significant data can be obtained even for very rare cells, due to the verification of the presence and/or identity of their progeny within a sample, including their clonal relationship.

The present invention also provides methods for the quantification and/or qualification of antimicrobial susceptibility and resistance (e.g. in the case of bacterial infections, antibiotic resistance and susceptibility), which leads not only to therapeutic decisions but also to the ability to both identify microorganisms based on a "fingerprint" or "profile" of antimicrobial susceptibility, but also to generate therapeutic decisions even in the absence of such identification; in this embodiment, efficacy of agent is the measurement. In this case, results can be correlated with the "minimum inhibitory concentration", or "MIC", of an antibiotic for a microorganism.

The present invention also provides for rapid quantification and/or qualification of microorganisms within a patient sample by using systems that allow concentration of the microorganisms on a detection surface. For example, one significant problem in biodetection is the fact that many clinical samples may be either quite dilute (e.g. blood), or the microbial count per unit sample can be low. As outlined, the present invention provides methods of concentrating the microorganisms to allow both faster and more accurate detection within a biosensor. Furthermore, the preferred detection methods are not dependent upon the analyte concentration per se, which is the case with most conventional methods. Instead, the methods of the invention count the absolute number of individual organisms regardless of their concentration in the specimen or sample vehicle. This discrete counting method provides substantial advantages over concentration-based detection in reducing noise levels and increasing sensitivity. While a wide variety of useful concentration and collection techniques are included herein as described below, electrophoretic transport of the microorganisms to the detection surface is of particular interest. The system can take a variety of configurations, as outlined herein. In general, two different main configurations are used, although additional configurations are both discussed herein and contemplated. In one system, a first electrode and a second electrode are used to generate an electric field to effect electrophoretic transport and the detection surface(s) are between these electrodes (see for example FIGS. 1A, 1E, 1F). This can be in the horizontal direction (FIG. 1C) or in the vertical direction (see for example FIGS. 1B and 1F). In addition, different channels comprising the detection surface(s) can be used with a single set of electrodes (see for example FIG. 1E). Alternatively, sets of electrodes are used. In one aspect, each detection surface in an array can have an associated electrode (e.g., as outlined herein, either in close spatial proximity or the electrode itself is used as the detection surface) with one or more counterelectrodes (see FIGS. 1G, 1H, 1I and 1J); again, in either the horizontal (FIG. 1J) or vertical (FIG. 1K) orientation. In some cases, an electric field is applied as between the sets, or alternatively sequentially to different electrodes to move sample from one detection surface (associated with an electrode) to another (see for example Nanogen, U.S. Pat. No. 5,849,486 and U.S. Pat. No. 6,017,696, among others). Another aspect of the use of sets of electrodes is used in FIGS. 1H and 1G, wherein sets of first and second electrodes are used to set up electric fields. As will be appreciated by those skilled in the art, the concentration modules depicted in FIG. 1 may have additional components, such as microfluidic components as outlined below as well as be part of larger systems.

Using these configurations, and others outlined herein, the speed of microorganism binding to the detection surface is significantly increased. That is, increasing the concentration of the microorganisms in the vicinity of the detection surface, for example by electrophoresis, results in faster kinetics. Similarly, in the case where capture ligands are used, the speed is increased by both increasing the concentration of the microorganism in the vicinity of the capture ligand and reducing the distance a given microorganism must travel to find a binding ligand.

In some embodiments, the sequential or simultaneous use of a plurality of electrophoresis electrodes allows multidimensional electrophoresis, i.e. the solution may be targeted, "mixed" or "stirred" in the vicinity of the detection surface, to further increase the kinetics of binding. For example, polarities can be reversed to allow microorganisms that may not have bound to the detection surface to travel back "over" the surface, resulting in increased binding. Also, electrodes may be located and field polarity switched according to a programmed sequence so as to provide agitation in two dimensions of a plane, or in three dimensions.

In addition, due to the fact that many embodiments of the present invention rely on the sequential capture of the microorganisms followed by growth of the microorganisms (either in the presence or absence or both of antimicrobial agents), followed by detection, the toxicity of the electrophoretic buffers is important. Many traditional electrophoretic redox mediators can be toxic to cells (e.g. benzoquinone), either through oxygen activation and via alkylation of essential macromolecules. Accordingly, the present invention provides a number of electrophoretic buffers that utilize special pairs redox mediators with a number of advantages. First of all, these redox mediators allow low voltage electrophoresis to preserve viability of the microorganisms, as well as the use of particular electrode materials that have limited utility in high voltage electrophoresis (for example, indium tin oxide, "ITO" electrodes). In addition, these redox mediators find use in "closed systems", e.g. systems not open to the atmosphere. These are important for several reasons: bubble formation or other reactive species are not generated during the electrophoresis step, which can cause a number of problems, and secondly, closed systems are preferred to prevent the exposure of the technician to the potentially infectious samples, as well as reduce problems associated with discarding biological samples.

In general, the invention provides methods for the identification (including diagnosis) of microorganisms and microbial infections (including polymicrobial infections) in patients. There are a variety of methods used for identification of different microorganisms within the samples, e.g. providing specificity, although others are both outlined herein and contemplated. In one aspect, a plurality of detection surfaces are used. In one embodiment, each detection surface has a different specific capture ligand. That is, one detection surface may include capture ligands comprising antibodies to specific microbial species or genera, and another a different capture ligand to a different specific species. In some embodiments, a plurality of detection surfaces are used that are fluidically separated from one another; for example, as outlined below, one biosensor cartridge of the invention can have a plurality of detection modules, for example detection channels, where one sample can be divided into the detection modules and can then be subjected to different conditions, e.g. different antimicrobial agents, for evaluation. As outlined herein, the plurality of different detection surfaces on a single biosensor cartridge can all have non-specific capture, or specific capture ligands.

In some embodiments, the detection surface(s) rely on non-specific capture of the microorganisms, but the detection method relies on specific binding ligands; e.g. antibodies to a specific species of microorganism may be used with a fluorescent label. In this embodiment, simultaneous detection usually relies on different binding ligands containing different labels, while sequential detection can be done using one or more washing steps followed by a different binding ligand with the same label. Another aspect of the invention avoids the use of either specific capture or specific labeling. In this aspect, the invention provides for specific identification of a microorganism using spatial separation of the microorganisms on the detection surface based on detectable or known changes. For example, the ability to detect the division of single microorganisms allows identification on the basis of any number of parameters, particularly kinetic parameters, including but not limited to growth rates, assessment of metabolic activity, rate of cell kill with different antibiotics, as well as microorganism morphology, which can include size, shape, and relationships to sibling organisms (e.g. growth into clusters or chains, two-dimensional growth on the surface or three-dimensional growth away from the surface). In addition to the evaluation of rates, single data point analysis may also be done (e.g. increased area associated with an individual microorganism on the surface (e.g. positive growth), stagnant area (no positive growth) or loss of area (e.g. negative growth, apoptosis and/or death). Many of these parameters can be built into matrices or "fingerprints", that allow or improve the identification of a microorganism on the basis of a multiparameter analysis of its kill rates with different antibiotics and antibiotics combinations, for example.

The present invention also provides a number of devices that find use in the present methods. In general, the biosensor devices are designed to fit into a detection unit, and generally utilize a number of components, which can either be "on-chip" (e.g. part of a biosensor cartridge) or "off-chip" (where some of the components are part of separate device or devices into which the biosensor cartridge fits). These components include, but are not limited to, one or a plurality (e.g. an array) of detection surface(s), concentration modules (which as outlined herein frequently is configured with the detection surface(s)), detection modules (again, frequently configured with the detection surface(s)), input and output ports, channels, pumps, mixers, valves, heaters, fluid reservoirs (including sample reservoirs, reagent reservoirs, and buffer reservoirs), concentration controllers (e.g. in the case of electrophoresis, electrical controllers), and data collection and analysis (e.g. computer) components.

It should be noted that the discussion below is focused on the use of microorganisms as target analytes, but the detection of other target analytes, such as nucleic acids, proteins, molds, eukaryotic cells such as cancer cells, etc. is outlined in U.S. application Ser. No. 10/888,828, hereby incorporated by reference in its entirety.

For example, it should be noted that certain organisms that would be detected in the manner of the present invention may not be viable by themselves, but may be require a host (e.g. for the detection of a virus, prion, molecular markers, or intracellular bacteria). In that case, the detection surface can comprise host cells that support the growth of the virus or other organism. In that case, the detection of the infected target host cell proceeds in a manner to the methods outlined herein, and is generally done according to the characteristics of the virus and the host, and can include the presence of cell surface markers indicative of infection (for example by using labeled antibodies), by changes in the physiology of the host that results from infection, or through lysis or death of the host. It should be noted that the associated cells can also comprise helper cells, which aid in the growth of the organisms being tested through their proximity to the tested cells.

Accordingly, the present invention provides devices and methods for the detection, quantification, qualification and/or identification of microorganisms in samples.

Microorganism Detection

By "microorganism" herein is meant a member of one of following classes: bacteria, fungi, algae, and protozoa, and which can for purposes of the present invention include viruses, prions or other pathogens. In one aspect, bacteria, and particular human and animal pathogens are evaluated. Suitable microorganisms include any of those well established in the medical art and those novel pathogens and variants that emerge from time to time. Examples of currently known bacterial pathogens, for example, include, but are not limited to genera such as *Bacillus, Vibrio, Escherichia, Shigella, Salmonella, Mycobacterium, Clostridium, Cornyebacterium, Streptococcus, Staphylococcus, Haemophilus, Neissena, Yersinia, Pseudomonas, Chlamydia, Bordetella, Treponema, Stenotrophomonas, Acinetobacter, Enterobacter, Kiebsiella, Proteus, Serratia, Citrobacter, Enterococcus, Legionella, Mycoplasma, Chlamydophila, Moraxella, Morganella*, and other human pathogens encountered in medical practice. Similarly, microorganisms may comprise fungi selected from a set of genera such as *Candida, Aspergillus*, and other human pathogens encountered in medical practice. Still other microorganisms may comprise pathogenic viruses (sometimes human pathogens) encountered in medical practice, including, but not limited to, orthomyxoviruses, (e.g. influenza virus), paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLVI and II), papovaviruses (e.g. papillomavirus), polyomaviruses, and picornaviruses, and the like. In the viral aspect, in general, the methods and compositions of the invention may be used to identify host cells harboring viruses.

Samples

The invention provides methods of detecting microorganisms within samples. As will be appreciated by those skilled in the art, the sample solution may comprise any number of sources, including, but not limited to, bodily fluids (including, but not limited to, blood, urine, serum, lymph, saliva, anal and vaginal secretions, perspiration, peritoneal fluid, pleural fluid, effusions, ascites, and purulent secretions, lavage fluids, drained fluids, brush cytology specimens, biopsy tissue, explanted medical devices, infected catheters, pus, biofilms and semen) of virtually any organism, with mammalian samples, particularly human samples, and environmental samples (including, but not limited to, air, agricultural, water and soil samples) finding use in the invention. In addition, samples can be taken from food processing, which can include both input samples (e.g. grains, milk or animal carcasses), samples in intermediate steps of processing, as well as finished food ready for the consumer. The value of the present invention for veterinary applications should be appreciated as well, and its use for the analysis of milk in the diagnosis and treatment of mastitis, and the analysis of respiratory samples for the diagnosis of bovine respiratory disease, is of particular note.

Samples can range from less than a milliliter up to a liter for certain respiratory lavage fluids, and can further range in bacterial concentration from less than one bacterium to greater than $10^9$ bacteria per milliliter. Furthermore, the sample can be present in blood, urine, sputum, lavage fluid or other medium. Sample concentration both concentrates the sample so that bacteria that are present in small numbers can all be effectively introduced into the system, as well as so the background liquid medium can be normalized, or in some cases eliminated or reduced, to have consistent properties upon introduction to the system. It should be noted, however, that certain samples, however, can be used without concentration or other modification within the present invention.

Detecting Growth

"Growth" as used herein includes positive, neutral and negative growth. "Positive growth" in the case of microorganisms that are cells (e.g. bacteria, protozoa and fungi) refers to the increase in size and/or procession of cell division, and particularly includes the production of daughter cells. Thus, "detecting positive growth" of a discrete microorganism refers to detecting either an increase in the size of the microorganism and/or detecting the presence of cell division, which may or may not increase the total area occupied by the microorganism. It should be noted that in some cases, as is outlined herein, positive growth can be detected as an increase in the area on the detection surface that the parent cell or daughter cells occupy. Other microorganisms can grow "off" the surface and thus may not increase their "footprint" on the detection surface while they increase volume.

In the case of viruses, "positive growth" refers to the reproduction of viruses, generally within a host cell, and can include host cell lysis, in the case of lytic viruses. Thus the "positive growth" of a virus may sometimes be detected as a loss of the discrete host cell.

"Detecting growth" can also refer to detecting a lack of growth, e.g. either neutral or negative growth. That is, some antimicrobial agents act by retarding positive growth yet do not kill the cells; this is generally referred to a "neutral growth". Thus, detecting little or no change in the size, shape, volume and/or area of a cell (on a surface) is included within the evaluation of "growth", e.g. in the absence of an agent, a microorganism will exhibit positive growth, but in the presence of the agent, a lack of growth is significant, even if the microorganism does not die. It should be noted that in some cases, there will be small changes in the size, shape, volume and/or area of a cell on the detection surface, but this can be distinguished from positive growth.

"Detecting growth" can also refer to detecting negative growth, e.g. necrosis. In addition, there have been some limited discussions of bacterial programmed cell death (e.g. apoptosis and/or autophagic cell death), which would be considered negative growth as well. In general, detecting negative growth relies on changes, usually but not always decreases, in microorganism size, shape, area or volume that can be detected by the methods of the invention.

Thus, "detecting growth" can refer to detecting positive growth, a lack of growth, e.g. detecting cells that are not actively dividing but are not growing positively, and negative growth, e.g. death.

In general, the invention is unique in that detecting growth is done at the individual or discrete microorganism level, rather than at the colony level. Thus, "detecting growth of a discrete microorganism" is done as an evaluation of growth of an individual cell in a period of time such that a small population of daughter cells can be formed, but prior to the ability to visually see a colony with the naked eye. Thus, the "quantum microbiology" component of the invention allows detection within only a few doubling times of a microorganism, rather than tens or hundreds of doubling times. In addition, as outlined herein, the methods of the invention do not require an initial growth of microorganisms (either liquid or solid) prior to the assay; the present invention is sensitive enough to start with biological samples with no growth prior to the assay. In general, the methods of the invention utilize from 1 to about 10 doubling times total, with from about 1 to about 4 being particularly useful, and 1 to 2 being ideal in situations where the "time to answer" is being minimized.

A variety of methods of detecting growth are outlined below.

Antimicrobial Agents

As is more fully described below, the methods optionally include the determination of the susceptibility, resistance or tolerance level of microorganisms to antimicrobial agents. "Antimicrobial agents" are a type of bioactive agents, outlined below, and are agents that modulate growth of microorganisms, as defined above.

As is known in the art, and depending on the microorganism, a variety of antimicrobial agents are tested, frequently in a matrix setting of different agents and different concentrations of agents. Suitable antimicrobial agents include, but are not limited to, antibiotic families such as cephalosporins, penicillins, carbapenems, monobactams, other novel beta-lactam antibiotics, beta-lactamase inhibitors, quinolones, fluoroquinolones, macrolides, ketolides, glycopeptides, aminoglycosides, fluoroquinolones, ansamycins, azalides, lincosamides, lipopeptides, glycolipopeptides, streptogramins, polymyxins, tetracyclines, phenicols, oxazolidinones, nitroamidazoles, folate pathway inhibitors, and other families, as well as bacteriophages, including novel agents, used as antibiotics in clinical practice or in research. Antiviral agents are also included within the definition of antimicrobial agents and include both known approved antiviral agents as well as experimental ones. In addition, combinations of these agents can be tested, particularly in light of the evolution of resistant strains. Also, as described herein, the concentration of the antimicroorganism agent may be changed over time to reflect the pharmacokinetics of the antimicroorganism agent in animal tissue. Furthermore, the assays herein can be used to test candidate antimicrobial agents and their efficacy, including measurement of MIC, MBC, time-kill kinetics, suppression of cell division, resistance induction and selection, and pharmacodynamic parameters.

In general, the methods of the invention utilize a number of steps as outlined below, generally comprising an optional sample preparation step, depending on the nature and concentration and volume of the sample; a concentration step, optionally including a preconcentration step; associating the microorganisms on the detection surface(s) at predominantly independent sites, which may be part of the concentration step; subjecting the microorganisms to growth conditions, in the presence or absence (or both) of antimicrobial agents; and detecting the presence or absence (or both, in the case of mixed populations) of the microorganisms. Additional methods are involved in the assessment of the susceptibility to antimicrobial agents.

The invention further provides device(s) to accomplish these methods, as outlined herein.

Sample Preparation

In one aspect, the invention provides preparing the sample prior to introduction to the concentration step (e.g. electrophoretic step) or detection surface(s). The method of preparation depends upon the type of material being assayed, and can include the maceration of solid tissue, centrifugation, ion exchange beads or columns, chromatography, filtration, stacking electrophoresis, or forms of biochemical separation. In one aspect, buffer exchange is done, and sample preparation agents can be added. For example, a simultaneous concentration (as outlined below) and sample preparation step can be done, for example by centrifuging the sample down and resuspending the microorganisms in suitable buffers. For example, when microorganisms are the target analyte, saponins can be used, generally in a range from about 0.01%-1% as is known in the art, to disrupt animal cells and cell debris. Similarly, reducing agents such as DTT can be use to disrupt mucus in samples, and in some cases this may be done enzymatically as well. Additionally, protease inhibitors can be included (e.g. protease inhibitor mix from Roche, Complete from Boeringer, leupeptin, PMSF)—these are used to prevent protease action on cell surfaces, which tends to decrease their charge. In general, the preparation aspect may include any techniques as are already well known to those skilled in the art and novel techniques and improvements as may be devised by practitioners and researchers from time to time.

It should be noted that many prior art techniques rely on an initial liquid growth of the microorganisms within a sample prior to analysis (plating, etc.). In one aspect of the invention, no initial (e.g. pre-application to the biosensor) growth phase is done.

Concentration of Microorganisms

As outlined herein, it is generally, but not always required, to concentrate the microorganisms within the sample either prior to, during or after application to the biosensor and the detection surface(s). Suitable concentration methods include, but are not limited to, electrophoresis, dielectrophoresis, centrifugation, affinity capture, phase partitioning, magnetic field capture, filtration, gravity, recirculation or diffusion, or combinations of these. It is also convenient as part of or prior to the concentration step to perform a pre-filtering in order to remove either larger or smaller (or both) contaminants, while allowing the passage of the bacteria to be monitored. Such filters can comprise nitrocellulose, nylon, cellulose, or other membranes, bead filters (including size filters), or other filters as may be convenient.

Preconcentration

In one embodiment, the microorganisms are "preconcentrated". "Preconcentrated" in this context means that the microorganisms are partially concentrated prior to growth on the detection surface(s). The preconcentration performs two functions. Firstly, the ratio of number of microorganisms to the volume of the sample is increased, so that the greatest possible fraction of the sample can be used in the system. A second reason is that the microorganisms may be in a liquid whose electrical or other properties are incompatible or non-optimal for the detection system. For example, if electrophoretic methods are subsequently to be used, the efficacy of such methods is improved generally by the use of low electrolyte buffers. In such case, the microorganism sample liquid will be replaced by a liquid that is more compatible with the system.

There are two main preconcentration methods; one done prior to introduction of the microorganisms to the biosensor cartridge, and one done on the cartridge.

Pre-Cartridge: Affinity Capture

In some cases, it is desirable to preconcentrate the microorganisms prior to introduction to the cartridge. This may be done in some cases by using an elutable collector. In such a system, the sample is filtered through a matrix (generally referred to as a "column") which is densely packed with a material that reversibly binds the microorganisms. Once the sample has been run through the column, the microorganisms are eluted, generally through chemical, enzymatic or physical changes such as salt concentration, pH, etc. Such a collector can be used to concentrate the microorganisms in a smaller volume of buffer, to place the microorganisms into a uniform medium that is well suited for further steps in the method, as well as to remove contaminating material that has size or charge differences from the microorganisms that are desired to be monitored. (Thus, it should be noted that in some cases, there may be just a buffer exchange and no actual concentration, although this is generally not the case).

A preferred embodiment of this sample preparation is that of a cartridge with volume of 50-1000 microliters, and preferably less than 250 microliters, in which an ionic exchange resin, generally beads, is packed. In this aspect of the invention, the sample can be pressed through the cartridge either without modification, or with the addition of a buffer to regulate the pH, and/or also in the presence of a preferably non-ionic detergent, in order to reduce non-specific binding of the microorganisms to the system components or to each other. It is preferable for the pH to be relatively neutral (in the range of pH 6 to 8), and in any case sufficient that the microorganisms remain viable and maintain a negative charge, and that the resin maintain a positive charge. This negative charge is typical for most microorganisms, but it should be noted that for any organism that is typically positively charged, a cationic resin can be substituted for the anionic resin, and the control of pH will be the opposite of what is described above and below for negatively charged organisms.

The microorganisms can in general be eluted from the resin in a volume not significantly different than that of the cartridge, and with care taken not to mix the eluting solution, even smaller than that of the cartridge. In general, after elution from the cartridge, the solution will be neutralized, preferably with a zwitterionic buffer so that the conductance of the buffer is not increased too much. Other properties of the resulting medium can be adjusted as needed, including ionic strength, conductance, the presence of surfactants, the presence of nutrients or growth factors for the microorganisms, and the pH. In general, as will be discussed below, it is preferable for the microorganisms to be in relatively low conductance solution. Given that the elution will be performed at pH's either above 3 or below 11, the resulting neutralized solution is likely to have an ionic strength of less than 10 mM salt, which is preferable for the subsequent steps. This affinity capture can be used alternatively as a sample preparation method, but also results in a pre-concentration of microorganisms, and can be sued for that purpose as described below.

Preconcentration in the Cartridge

Figure 2D:
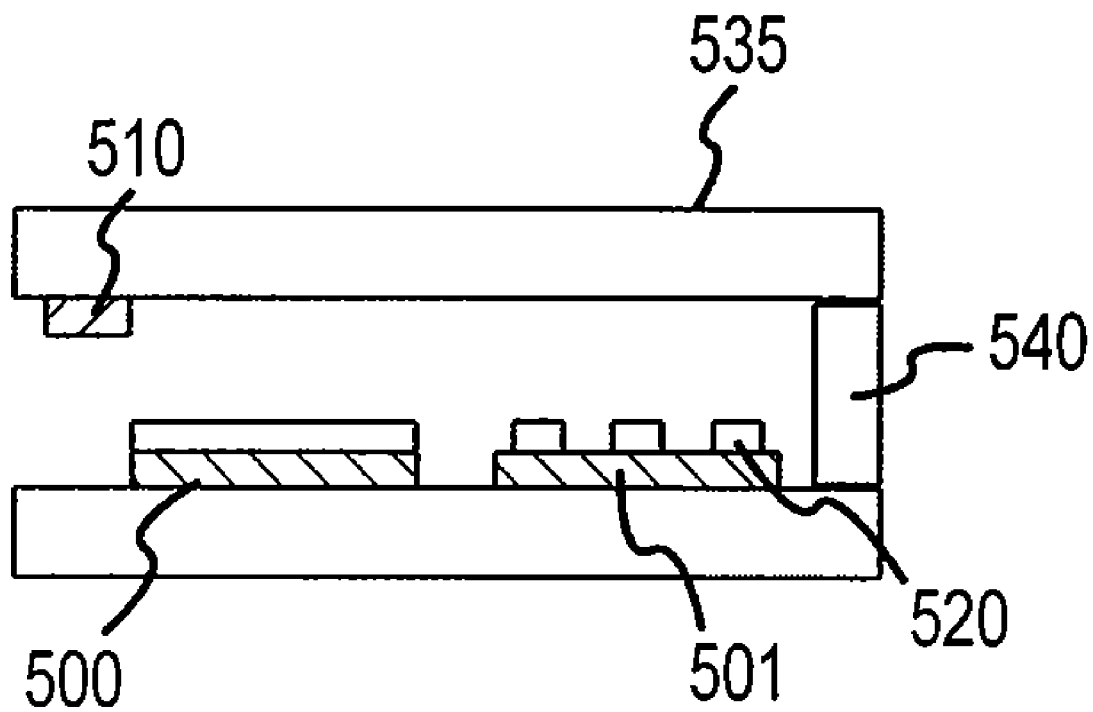

As will be appreciated by those skilled in the art, there are a wide variety of methods to preconcentrate the microorganisms, several of which are depicted in the Figures. Any of the techniques outlined below may be used to preconcentrate the microorganisms on a preconcentration surface such as depicted in FIG. 2. For example, as depicted in FIG. 2, and described in further detail below, electrophoresis is used to collect the microorganisms on a non-specific surface, and then the targets are driven off the preconcentration surface onto the detection surface(s). Alternatively, again as described below, membranes or filters can be used, with positive pressure or centrifugation, for example, to preconcentrate the analytes prior to application to the detection surface(s).

Electrophoretic Systems and Geometries

After the optional preconcentration step, a useful method of the present invention is to electrophoretically concentrate the microorganisms onto a detection surface on which to monitor the growth of the microorganisms and assess their susceptibility to anti-organism agents (AOAs). The method uses multiple electrodes placed at different potentials, between which the microorganisms are introduced in an electrolyte. When constituents in the electrolyte undergo oxidation and reduction (redox) reactions at the electrodes, there is an electric field that is generated within the electrolyte that the microorganisms, being generally charged (and whose charge can be somewhat manipulated by varying the composition and pH of the electrolyte, and/or alternatively using electrophoretic tags that add charge), will migrate to one or the other electrode under the influence of the electric field.

Figure 1K:
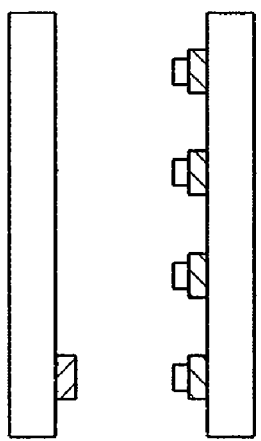
Figure 1J:
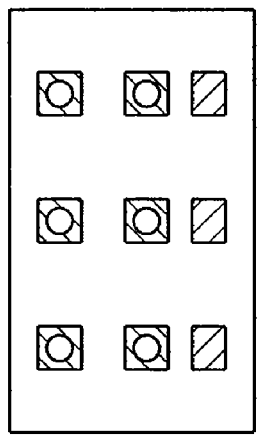
Figure 1I:
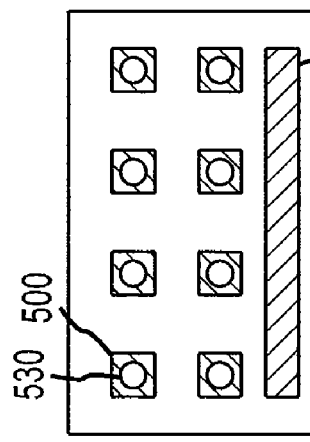
Figure 1L:
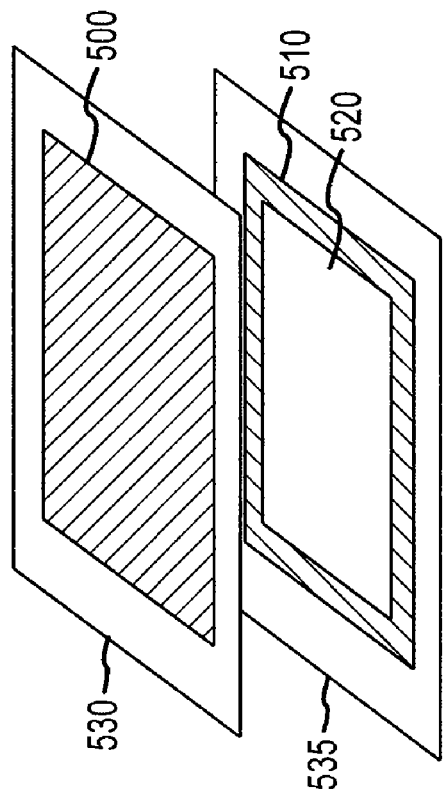

Accordingly, in one aspect, the microorganisms within the sample are concentrated onto the detection surface(s). As outlined herein, there are several general configurations that are used. Generally, in one aspect, there is a "bulk" electrophoretic step, using a first electrode and a second electrode to generate an electric field, and the detection surface(s) are between these electrodes, either in a horizontal or vertical direction. Several of these embodiments are shown in FIG. 1. In another aspect, sets of electrodes are used to either generate a single electric field (FIG. 1D), multiple electric fields (FIGS. 1G, 1I, 1J and 1K), or sequential electric fields (FIGS. 1I 1J and 1K). Additionally, an alternative way to categorize these systems is those in which the detection surface(s) have underlying electrode(s) (sometimes referred to herein as "closely associated electrodes", e.g. FIGS. 1F, 1I 1J, 1K and 1L) and those that do not (e.g. FIGS. 1A, 1B, 1C, 1D, 1E, 1G). As described herein, in one aspect, detection surface(s) can be directed placed onto electrodes to be considered as "underlying electrodes".

For all the embodiments discussed herein, the number, sizes, shapes and positions of the electrophoresis electrodes can be modified to generate either substantially uniform, variable or asymmetrical electric fields. As such, the size and shape of the electrodes depicted in the figures is representational only. In most cases, the figures do not depict the electrical interconnects used to connect the electrodes with the appropriate power source and controller, described below.

Accordingly, in one aspect, a single set of electrodes is used, with the detection surface(s) between these electrodes within the electric field. In one aspect, the electrodes and detection surfaces are on a single substrate; for example, as shown in FIG. 1A, first electrode 500 and second electrode 510 are on first substrate 530 with detection surfaces 520. Note that the electronic interconnects 550 are not depicted in these Figures, but may be either on the surface of the substrate (see for example FIG. 3D) or through the substrate (see for example FIG. 3E) for interconnection with power sources, generally off-chip. These systems with the functional components on a single substrate (including FIGS. 1A, 1D, 1E, 1H, 1I and 1J) can be open systems, e.g. they could be in the bottom of a microtiter well or other well on a planar surface, or they can be part of a closed system. Suitable closed systems include the use of a second substrate with a spacer to define a cavity, or the entire cartridge being formulated out of a single material (or made in layers that are subsequently assembled). Thus, FIG. 1A depicts a two electrode system with a plurality of detection surfaces within the electric field. FIG. 1E depicts a two electrode system with channels comprising one or more detection surfaces (the figure depicts multiple detection surfaces, (which in some embodiments will have different capture binding ligands) within each channel, but a single detection surface is also contemplated, particularly in the case of non-specific capture). FIG. 1D depicts multiple channels in the substrate (again, figure the depicts multiple detection surfaces, (which in some embodiments will have different capture binding ligands) within each channel, but a single detection surface is also contemplated, particularly in the case of non-specific capture), each with a set of electrophoresis electrodes. FIG. 1F depicts a biodetection cell wherein a single probe electrode 510 underlies multiple detection surfaces 520 which are placed into an array form. The walls of the cell are not placed in the diagram, but may be, for example, a gasket material to form a water tight seal. A reference electrode 500 is physically placed preferably above the probe electrode 510 and can optionally be of roughly similar size to the probe electrode, so that the electric field between the two electrodes is substantially uniform. In general, as is true for many of the embodiments herein, the electrodes are optionally roughly parallel to one another, so that the electrophoretic fields that are generated are roughly perpendicular to the surface of the probe electrode, and give rise to even deposition of the targets onto the detection surfaces.

In some embodiments, sets of electrodes are used to generate the electric fields. For example, alternative arrangements are shown in FIGS. 1G, 1I 1J and 1K. In FIG. 1G, the electrodes do not underlie the detection surfaces. In this case, the detection surfaces are arranged in an array format. Two electrode 510 are lateral to the array, and sit underneath an array of partial reference electrodes 500, labeled in this figure P, Q, and R. The number and type of partial reference electrodes can be varied, and the goal of the placement of the two electrode 510 and the partial reference electrodes 500, is to manage the strength and topology of the electric fields by adjusting the relative voltages of the electrodes. For instance, placing the second electrode and the partial reference electrodes P, Q and R at a negative bias, and the first electrode at a relatively positive bias will cause a largely horizontal electric field across the surface of the array. Multiple partial reference electrodes can be used to prevent the "shorting" of the electric field that could occur with a large, continuous electrode. FIG. 1H is similar, and shows the electric field strengths from the sets of electrodes, to provide a vertical component of the electric field at the location of the array that is relatively constant with a downwards component. By adjusting the relative strengths of the voltage bias at the different electrodes, a variety of different electric field topologies can be arranged for purposes that will be described below.

In some aspects, components are on two substrates; for example, in FIGS. 1B, 1C, 1F, 1G and 1K, one of the electrodes is on the "top" substrate (it should be noted that "top" and "bottom" as used herein are not meant to be limiting). Again, the side walls of the chamber are not shown.

Figure 10:
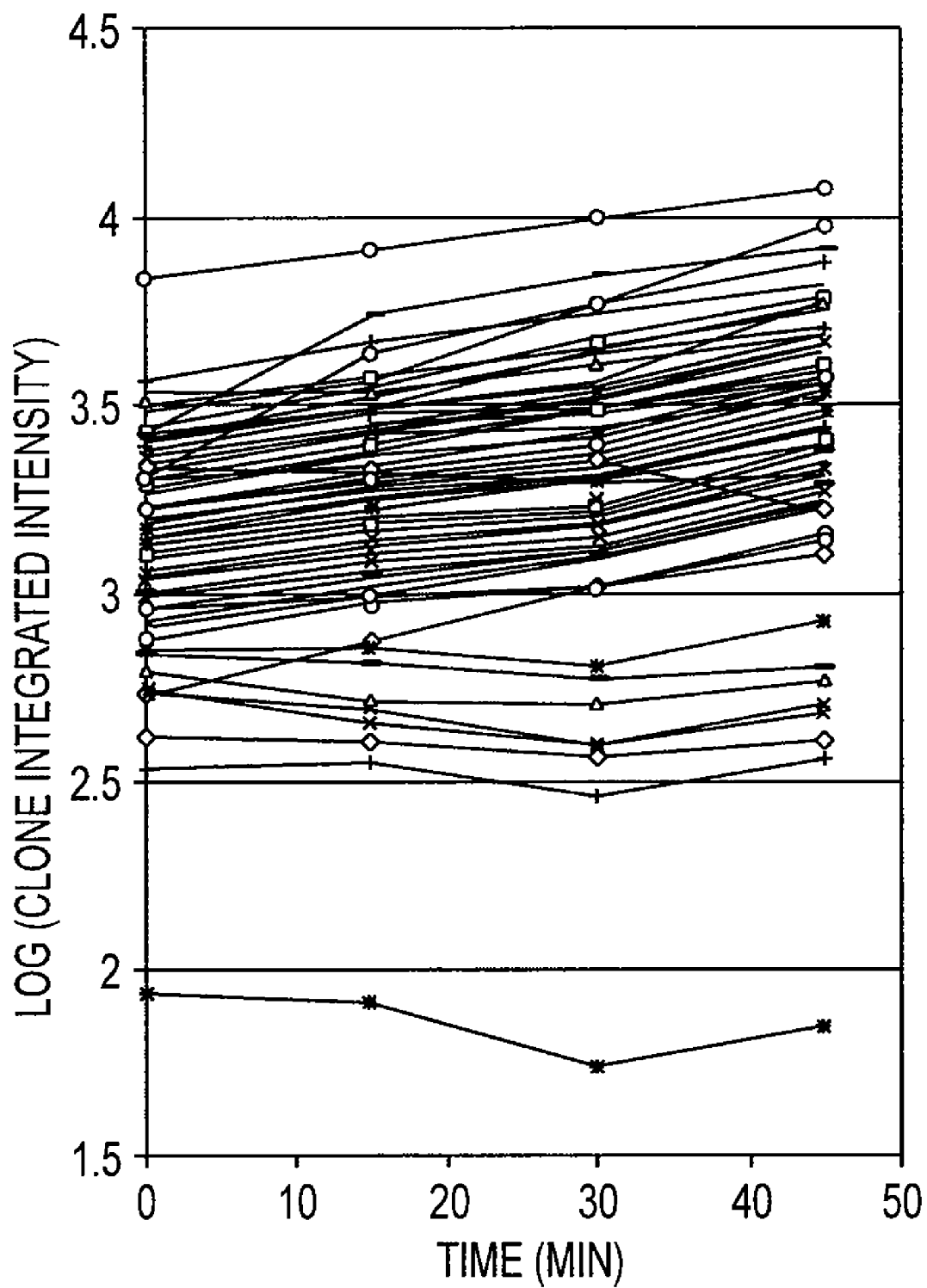
FIG. 10 depicts some results from Example 7.

In an additional aspect, the sets of electrodes are used to create sequential electric fields to allow the movement of analyte microorganisms between electrodes. This generally involves applying a potential between two electrodes, and then reversing the polarity of the second electrode to have it function as the "first" electrode in the second electrophoretic step. In this aspect, there may be one reference electrode (e.g. FIG. 1I) or several (e.g. FIG. 1J), and one or more detection surfaces associated with the working electrode (see for example FIGS. 1I 1J and 1K, all of which depict multiple detection surfaces, although a single detection surface is also contemplated). In addition, FIG. 2 depicts the use of a variety of preconcentration electrodes 810 and associated detection surfaces 820 and working electrodes 816 and 819. In the device of FIG. 2J, a potential can be applied between electrode 510 and electrode 500, and then between 500 and 501. Alternatively, within this same device, the potential can be applied between electrode 510 and simultaneously electrodes 500 and 501. In another example, in the device of FIG. 2C, which optionally includes electrodes 817B, 817C, etc., a potential can be applied as between electrode 817A and preconcentration electrode 819A, followed by sequential potentials between 819A and 819B, 819B and 819C, etc. Reference is also made to FIG. 10 and the accompanying text of U.S. application Ser. No. 10/084,632 hereby incorporated by reference in entirety.

In an optional step, weakly-adhered nonspecifically-bound material can be removed from the array by placing a small net positive bias to electrodes P, Q, and R, drawing the material away from the array.

In an additional aspect, the electrophoresis utilizes an electrophoretic tag as outlined herein; see also U.S. application Ser. No. 10/888,828. Generally, the tag is added at a concentration that allows the rapid association of the tag with the microorganism. This step can be done at any point in the assay, with one aspect being contacting the tag with the sample before loading. In some cases, using titratable electrostatic tags allows the adjustment of pH and other conditions during electrophoresis. A variety of electrophoretic tags are described in U.S. application Ser. No. 10/888,828, specifically in FIGS. 6 and 7. In general, electrophoretic tags have high electrostatic charges, and one or more tags can be used per microorganism. Electrophoretic tags are generally utilized in "sandwich" configuration, and as described in U.S. application Ser. No. 10/888,828, can be comprised of multiple functional components, including, but not limited to, indicator components, linkers, electrostatic components, etc.

If the electrode surface to which the microorganisms are drawn has a capture agent, to which the microorganisms bind, the electrodes can be switched off after the microorganisms have been concentrated on the surface, and the microorganisms will remain in place. The capture agent (sometimes referred to herein as the "capture ligand", the "capture probe" or the "capture agent") as will be described later in more detail, can be either generally "sticky" to a wide range of microorganisms (by, for example, general electrostatic or hydrophobic interactions), or alternatively, can be specific for a narrow range of microorganism specificities, such as by the use of antibodies that are strain specific. The capture agent is also referred in this specification as the "probe". It should be noted, however, that on occasion, the electrodes can be associated with a non-binding surface to which microorganisms do not bind, for concentration of the microorganisms temporarily, and such electrodes to which the microorganisms are drawn may also be referred to as probe electrodes.

In other embodiments, a biodetection cell can include a single probe electrode can underlie multiple probe locations which are placed into an array. The walls of the cell will generally comprise gasket material to form a water tight seal. A reference electrode is physically placed preferably above the probe electrode and of roughly similar size to the probe electrode, so that the electric field between the two electrodes is substantially uniform. However, it is also within the spirit of the present invention for the reference electrode to have various shapes and positions that allow for similar or even lesser uniformity. In general, the electrodes are roughly parallel to one another, so that the electrophoretic fields that are generated are roughly perpendicular to the surface of the probe electrode, and give rise to even deposition of the microorganisms onto the probe locations.

This arrangement of the probe electrode and the probe locations allows for standard methods of placement of probes on the electrode surface using known techniques, including but not limited to, spotting, printing, etc. Furthermore, the association of the microorganism with the probe can be performed in parallel with all of the different probe locations, rather than serially as performed with the prior art.

In an alternative arrangement, a biodetection cell can include electrodes that do not underlie the probe locations. In this case, the probes are placed in probe locations arranged in an array. A first electrode and a second electrode can be lateral to the array, and sit underneath an array of partial reference electrodes, labeled in this figure P, Q, and R. The number and type of partial reference electrodes can be varied, and the goal of the placement of the first electrode, the second electrode, and the partial reference electrodes, is to manage the strength and topology of the electric fields by adjusting the relative voltages of the electrodes. For instance, placing the second electrode and the partial reference electrodes P, Q and R at a negative bias, and the first electrode at a relatively positive bias will cause a largely horizontal electric field across the surface of the array. The need for the multiple partial reference electrodes is due to the "shorting" of the electric field that would occur with a large, continuous electrode, making it difficult to maintain an electric field across a larger electrode.

In other embodiments, the second electrode and the partial electrodes have a negative bias, and the first electrode has a relatively positive bias. The vertical component of the electric field at the location of the array is relatively constant with a downwards component. By adjusting the relative strengths of the voltage bias at the different electrodes, a variety of different electric field topologies can be arranged for purposes that will be described below.

Electrophoretic Buffers and Mediators

In one embodiment, the methods of the invention utilize low voltage electrophoresis and specifically selected redox mediators. The use of redox mediators has a variety of advantages, including, but not limited to, the generation of significant electric fields and currents below 1 volt of applied potential, the use of electrode materials that have limited utility in many high voltage applications, the ability to use a "closed system" due to the general recycling of the redox system that avoids exhaustion, the ability to use a wider variety of surface chemistries for detection surfaces, and low power requirements. In one aspect, the redox mediators are net neutral molecules to limit the electrophoretic effect on the charged analytes (e.g. microorganisms).

Low voltage electrophoretic transport enables use of materials that are limited by their own electrochemical or other physical properties. For example, indium tin oxide (ITO) is a heavily utilized commercial material since it is one of the few materials known to be both highly conductive and highly transparent. The use of indium tin oxide in electrophoretic applications has been limited by the fact that the material undergoes an electrochemical transition into a black non-transparent material at potentials above 1 volt relative to a standard hydrogen electrode. As a result, the application of ITO in systems relying on the hydrolysis of water is not generally feasible. However, significant current and electric fields can be generated with ITO electrodes by employing redox mediators and applied potentials below the critical breakdown potential.

In addition, the byproducts of the standard redox process can lead to very harsh conditions near the proximity of the electrodes including the formation toxic agents such as the reactive hypochlorite anion (bleach) when water is hydrolyzed in the presence of chlorine anions. In contrast, consumed redox mediators are regenerated with out the formation of side products such as gases or other reactive species. As a result, the system is more tightly controlled and useful provided the mediators themselves are non-reactive towards analyte of interest.

In some cases redox agents may be toxic to cells and cellular organisms. For example benzoquionones have been known to be toxic via two main mechanisms: oxygen activation by redox cycling and alklyation of essential macromolecules. Mediator toxicity maybe mitigated by limiting exposure of cells and cellular organisms, developing impermeable mediator derivatives, utilizing redox mediators with low standard redox potentials and/or reactivity.

In the case of cells and cellular organisms the standard redox potential of oxidizing agents loosely correlates with toxicity. Modification of standard redox potentials in the case of benzoquinones can be accomplished with the addition of electron donating groups such as alkyl (e.g. methyl or tert-butyl) or hydroxyl groups to the core ring structure.

Toxic oxidizing agents such as benzoquinone may also be substituted with non-toxic redox agents in asymmetric mediator systems. For example, the cell potential for the oxidation of water coupled with the reduction of hydroquinone is significantly less than one volt and useful in low voltage electrophoresis. Asymmetric mediator methods provide another route around toxicity issues associated with benzoquinone. Reducing agents such as dithiothreitol (DTT) or other suitable quenching agent may be used to chemically quench and oxidize benzoquinone into its non-toxic hydroquinone form as it is formed from the oxidation of hydroquinone, and the oxidized form of DTT can serve as the oxidizing agent instead of water. In general, the use of reducing agents such as DTT in the solution maintain a reducing environment which protects microorganisms from the damaging effects of strong oxidizing agents, and they are preferably present in excess to the constituents of the redox system, and more preferably in two-fold or more excess to the constituents of the redox system. For example, if the redox system comprises 10 mM hydroquinone as the reducing agent and water as the oxidizing agent, it is preferable for the DTT to be present in amounts of 20 mM or greater. Asymmetric redox mediator systems may also include multiple redox agents as in the case of a quinoxaline oxidizing agent used in conjunction with a catechol reducing agent.

Mediator toxicity may also be mitigated by minimizing the amount of electrophoresis time or time in the mediator solution followed by the rapid exchange of redox solution for non-toxic medium. Cell or cellular organism exposure to mediators may also be limited with the use of fluid flow. For example, laminar flow environments afford the opportunity to confine the toxic oxidizing agents like benzoquinone (BQ) to the cathode away from cells or cellular organisms confined within the non-toxic hydroquinone (HQ) reducing agent as illustrated below:

As the negatively charged cells pass through the chamber (from right to left) the HQ and BQ are reduced and oxidized at the respective electrodes generating an electric field while the cells are driven towards the anode away from the benzoquinone bulk solution. The HQ+cells solution may also contain a reducing agent (i.e. DTT) or other reagent designed to quench BQ formed at the anode resulting from the electrochemical reduction of HQ.

There are a number of methods that can be used to generate redox mediators which are not permeable to microorganisms based on physical size of mediator as well as other physical properties. These strategies are relevant in cases in which the toxicity results from mediator passage through cellular membranes and intracellular interference with organism or cellular respiration and/or reaction with other important molecules. Short oligomers of benzoquinones on molecular backbone such as polyethylene glycol or even polymeric forms of mediators will prevent intracellular damage. Furthermore, large steric groups such as tert-butyl or other alkane groups may also provide steric hindrance to prevent oxidative/reactive damage or intracellular permeation. Zwitterionic or charged versions of redox mediators may also be utilized to prevent intracellular migration. Other strategies include designing a reducing agent mediator in which the oxidized version is insoluble and forms a precipitant.

Accordingly, the present invention provides sets of redox mediators for use in electrophoretic transport of viable cells. An example of such reagents is the benzoquinone/hydroquinone system. In this case, hydroquinone is oxidized at the anode to benzoquinone, and benzoquinone is reduced at the cathode to hydroquinone. Because the reactions are complementary at the electrodes (i.e. have reversed potentials), the only cell potential is due to differences in concentration rather than differences in standard potential at the electrodes, and thus the electrophoresis redox reaction occur at relatively low potentials between the two electrodes. Furthermore, because the two species are not charged, the redox agents do not significantly increase the conductivity of the solution and thus do not compete with the charged molecules (e.g. DNA) or material (e.g. bacteria) for transport via electrophoresis.

Figure 14:
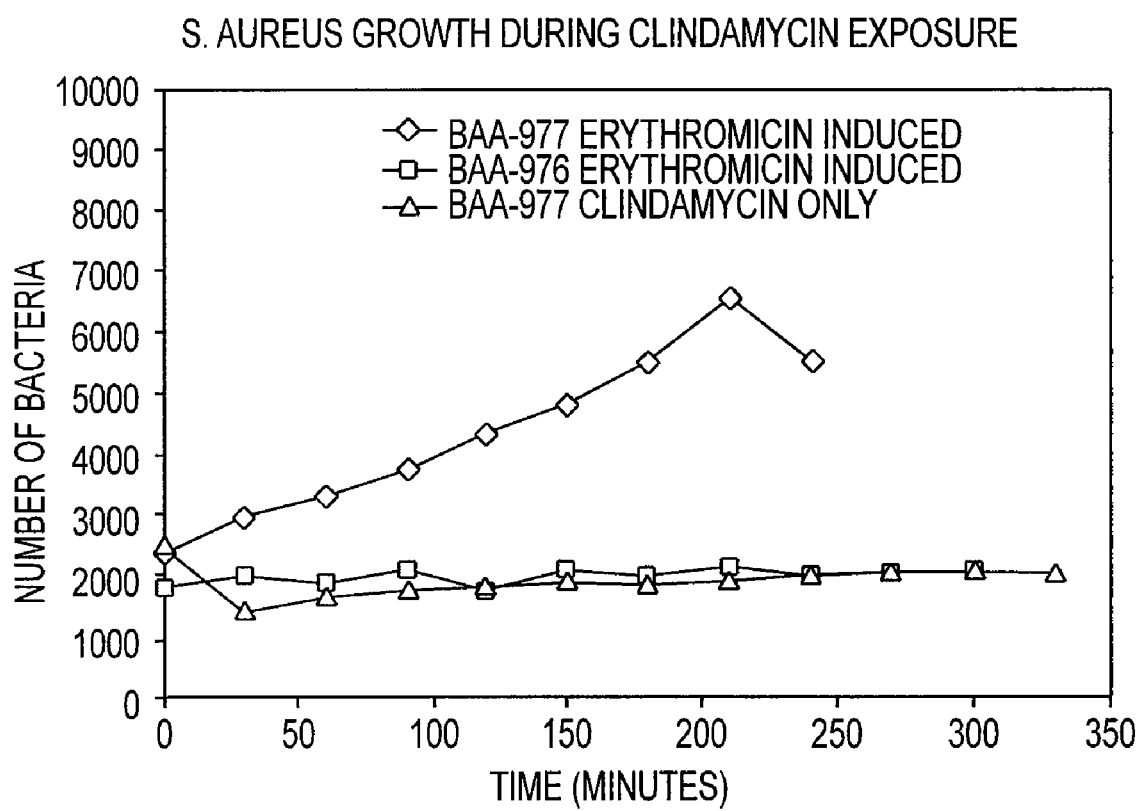
FIG. 14 depicts the growth curve of S. aureus as outlined in Example 10.

The redox scheme as described above can operate either with respect to a closed or open system. Reference is made to FIG. 14 of U.S. application Ser. No. 10/888,828 and the corresponding text, incorporated by reference herein. A closed system is closed off from the environment, and electrophoresis can be continued indefinitely without replenishing the redox reagents. This is beneficial for a number of reasons, including the containment of biological samples. An open system can be run either with the reversible redox reagents, or with replenishment. That is, there may be two pairs of reagents which do not regenerate each other (either directly as in benzoquinone and hydroquinone, or by mutual quenching of redox products, as described below). Thus, in this open system, in order to maintain electrophoresis, the reactants must be continuously replenished, which is accomplished generally by maintaining a flow of new reactants in the electrophoresis buffer into the space between the electrodes.

Depending on the amount of availability of charge carriers (which can be unrelated electrolyte, the redox mediators, or charged molecules or materials to be transported), the electrophoretic force, and therefore the rate at which molecules or materials can be transported, can be limited to the rate of diffusion of the redox mediators. This rate of diffusion can be improved significantly be making the distance between the cathode and the anode small—it is preferable for this distance to be less than or equal to 500 microns, even more preferable for this distance to be less than or equal to 250 microns, and even more preferable for this distance to be less than or equal to 100 microns.

There are numerous redox pairs that can operate within the present invention. As described above, benzoquinone and hydroquinone are well suited to this, and are preferably used in concentrations above 1 mM, more preferably used in concentrations above 10 mM, and most conveniently used in concentrations above 30 mM. It should be noted that the use of benzoquinone and hydroquinone are limited to an extent by their limited solubility, and so more polar or charged derivatives can be conveniently used to increase their solubility, such derivatives including the substitution of the ring carbons not bonded to carbon with halogens, nitrates, hydroxyls, thiols, carboxylates, and amines, and other such moieties. It should be noted that it is optimal for the system for the resulting redox agents to be uncharged (except as will be shown below), so that their distribution is not affected by the system electrophoresis, and so the substitution with a positively charged group (e.g. an amine) is balanced by a second substitution with a negatively charged group (e.g. a carboxylate), such as in 2-amino, 5-carboxy parabenzoquinone. In such cases of derivatized benzoquinones and hydroquinones, the concentrations of the redox reagents can be conveniently increased.

Other similar redox pairs include ketone/alcohol and aldehyde/alcohol pairs, whose ketone carbonyl group can be flanked by alkyl or aryl groups, which groups can also be derivatized with halogen, nitrate, hydroxyl, thiol, carboxlate; amino and other groups so as to modify the charge on the molecule or to increase its solubility. Another convenient system is that of dithiothreitol/dithioerythritol and their oxidized forms (which can be formed by the partial oxidation of solutions of the reduced forms, for example, by hydrogen peroxide), or alternatively by alkanes with terminal thiol groups (e.g. 1,5 dithiobutane). In general, it is preferable for the two thiols groups to be on the same molecule (as in dithiothreitol) as opposed to on separate molecules (e.g. as in beta-mercaptoethanol), so that the oxidation reaction is a unimolecular reaction that is relatively less sensitive to concentration (although the single thiols, such as betamercaptoethanol are acceptable reducing agents for many applications).

It should be noted that the redox pairs above are oxidized and reduced in pairs of electrons in such a manner that the charge on both redox pairs is the same, and is preferably neutral. The requirement that pairs of electrons be transferred can, however, reduce the rate of the reaction, and so it can also be convenient to use pairs in which one electron is transferred in the redox reaction. Examples of such pairs include ferrocene/ferrocinium and their derivatives, and ferrocyanide/ferricyanide. In such cases, it is preferable to use pairs in which the reduced product is neutrally charged, and the oxidized product is positively charged in those cases where negatively charged molecules or materials will be transported. The reason for this is that the oxidized product supplies counter-charge to the transport of the negatively charged transported molecules, and the reduced product is uncharged, and so does not compete for transport with the negatively charged transported molecules.

Another configuration of the system is that where the products of the redox reactions quench one another, such as in the following:

Anode: $2I^- \rightarrow 2e^- + I_2$

Cathode: $S_4O_6^{-2} + 2e - \rightarrow 2S_2O_3^{-2}$

The products of this reaction spontaneously react with one another according to $2S_2O_3^{-2} + I_2 \rightarrow S_4O_6^{-2} + 2I$, regenerating the starting state. The use of iodide or another halide is convenient, since the iodide is moved through electrophoresis towards the anode, and the resulting iodine is neutrally charged and can move through osmosis towards the other electrode where it will meet with the thiosulfate for the regeneration of the initial system.

In open loop systems without recycling, where the redoX pairs do not regenerate one another during their respective reactions, the range of redox agents is broader, and conveniently includes compounds including glutathione, ascorbate, methyl viologen, phenazine methosulfate, trolox, and others, including their redox pairs (such as GSSG for glutathione and dehydroascorbate for ascorbate, oxidized methyl viologen for methyl viologen). In this case, it is sometimes convenient that the charge of the molecule be such that the reactant be attracted towards the electrode at which it will participate in redox reactions (i.e. reactants to be oxidized at the anode should be negatively charged and reactants to be reduced at the cathode should be positively charged). This can generally be accomplished by derivatizing the molecule with one or more appropriately charged moieties. The main disadvantage of this is that a negatively charged redox agent, while increasing the rate of reaction, can also compete with the negatively charged transport molecules, such that increasing the amount of redox reactant can even reduce the overall transport of the transport molecules. Thus, care needs to be taken through experimentation to ensure that negatively charged redox reagents do not have an overall deleterious effect.

It should be noted, however, that small molecules of a redox pair, because of their high diffusion rates, are only moderately affected by the electrophoresis, and over the short distances that generally exist between the cathode and anode, show a modest gradient over the electrodes (often only 2-3 fold, and generally less than 10-fold). In this case, it may be useful to have one or both redox reagents be neutral or positively charged. In the case where both agents are positively charged, it is preferable that the agent that reacts at the positively charged anode be in larger overall molar concentrations to compensate for the lower local concentrations at the anode. In those cases where microorganisms are being transported in the presence of redox agents, it is important to note that some of the redox agents mentioned above can have toxicity for microorganisms. In cases where the subsequent growth or monitoring of live organisms is desired, this can be a significant problem. For that reason, it is useful either to use low concentrations of the toxic redox reagent (generally the oxidizing agent), to limit the duration at which the microorganism is exposed to the agent, or to use an agent with lower toxicity, even should that agent have less desirable redox properties. In addition, bacteria that have been exposed to a toxic redox agent can be treated after exposure to a counteracting agent. For example, should the toxic redox agent be an oxidizing agent, the addition of a reducing agent such as beta-mercaptoethanol or dithiothreitol can reduce the effects of the oxidizing agent. It should be noted that the one of the goals of the use of the redox agents is to allow electrophoresis to occur at a lower potential, both so as to minimize the production of harmful redox products (e.g. chlorine products from chloride), and as well so that optical detection can occur using ITO electrodes, which can be harmed by high potentials. Thus, the cell potential of the redox pairs chosen for the application is preferably under 2 V (the potential at which ITO begins to be affected), and even more preferably under 1 V and most preferably under 500 mV, since the range of potentials between the lowest potential at which electrophoresis occurs (i.e. 500 mV) and the endpoint (i.e. 2 V) will give some measure of control over the rates of electrophoresis. Even in those cases where the standard cell potentials of the redox agents may be outside of these ranges, the use of differing concentrations of oxidizing agent and reducing agent can provide a cell potential that allows for useful operation.

The general preferences of the redox mediators is that 1) they be soluble in water, and generally at a concentration of greater than 1 mM and more preferably at a concentration of greater than 10 mM, 2) that they be roughly uncharged at some pH between pH5 and pH 9, 3) that they have relatively low toxicity to microorganisms. Some redox mediators that meet some or all of the preferences to some extent include:

| Oxidizing Agent | Reducing Agent |
|---|---|
| 1,4 Benzoquinone | 1,4 Hydroquinone |
| Water | 1,4 Hydroquinone |
| 2,3-dihydroxy-1,4-dithiobutane | Dithiothreitol |
| Menadione | Menadiol |
| Adrenochrome | Reduced adrenochrome |
| 1,2 Benzoquinone | Catechol |
| Quinoxaline | Reduced quinoxaline |
| Chloranil | Tetrachloro-hydroquinone |
| Anthraquinone | Reduced anthraquinone |

Manipulation of Microorganism Charge

The effective charge of the microorganism may also be manipulated. The isoelectric point for a large number of bacteria have been characterized and reported in the scientific literature to generally range from pH 3 to pH 8, and most microorganisms of medical interest are negatively charged (i.e. with a negative zeta potential). In general, the mobility of microorganisms may be increased by increasing the pH of the electrophoresis buffer, which tends to deprotonate acidic groups, leaving the microorganisms more negatively charged. Additionally, the number of charged groups on the cells or cellular organisms can be altered with the chemical attachment of anionic or cationic reagents (i.e., carboxyl containing NHS esters). Cationic or anionic polymeric reagents (i.e., polyethyleneimine or poly-L-lysine) may also be physically absorbed on cells or cellular organisms. The use of metal chelators may also be employed to sop up polyvalent ions that will compete for the layer of counter ions tightly bound to the cells or cellular organisms decreasing their effective mobility. It should be noted that the use of physical or chemical attachment of anionic or cationic agents to the surface of microorganisms must be performed with care, to ensure that the identification agents or capture agents (e.g. antibodies) retain their affinity and specificity for the microorganism.

Dielectrophoresis

In one embodiment, the concentration method is dielectrophoresis. Dielectrophoresis relies on the polarization of the analyte and the creation of asymmetric electric fields. These methods generally require the use of electrodes that are shaped either in two or three dimensions so as to create electrical or electrophoretic fields that are non uniform. A description of the use of these dielectrophoretic electrodes is presented in G. H. Markx and R. Pethig, Dielectrophoretic Separation of Cells: Continuous Separation, Biotechnol. Bioeng. 45, 337-343 (1995), and G. H. Markx, Y. Huang, X. F. Zhou and R. Pethig, Dielectrophoretic characterization and separation of micro-organisms, Microbiology, 140, 585-591 (1994).

Centrifugation and Filtration

In one embodiment, the concentration method is either centrifugation or filtration, generally followed by resuspension of the microorganism in a small amount of fluid. It should also be noted that centrifugation can be accompanied by flocculation, precipitation or addition of a co-precipitate, and such methods are encouraged in that they permit the handling of very small numbers of microorganisms, and prevent aggregation of the microorganisms. In any of these cases, however, it is sometimes preferable that no material be added that will remain a particulate, especially with properties (size or density) similar to that of the microorganism (e.g. the use of polymer beads).

Both centrifugation and/or filtration can be done either prior to the introduction of the sample to the biosensor, or as part of the introduction step. For example, samples may be centrifuged or filtered, resuspended, and added to the biosensor. Alternatively, the biosensor may be configured such that the sample is added to a reservoir within the biosensor cartridge, the whole device is centrifuged to drive the microorganisms down to a surface of the biosensor (e.g. either a preconcentration or detection surface). Particular reference is made to the devices of FIGS. 39 and 40 of U.S. application Ser. No. 10/888,828, and the accompanying text outlining the methods and structures, hereby incorporated by reference.

Electrophoretic Stacking and Collection Electrodes

Another method in accord with the present invention is the use of electrokinetic concentration. In one such approach, concentration occurs at the boundary between two liquid columns in contact with each other in which one liquid has an ionic strength much lower than that of the other. Such a stacking or discontinuous buffer system is well known in the laboratory art of electrophoresis, including capillary electrophoresis. The present invention is well disposed to apply either weak or strong forms of discontinuous buffer concentration.

In another such approach a conductive electrode is placed beneath a non-binding zone in, for example, an antechamber to an analytical biosensor region. At the time of analyte concentration, this collector electrode receives a programmed electrical voltage that attracts analytes having the opposite polarity. The surface overlying the electrode is coated with a nonbinding, non-adsorbing material, such as deactivated OptiChem® produced by Accelr8 Technology Corporation. This electrical field serves to concentrate the analytes on the discrete area of the electrode material. Upon completion, termination or reversal of the electrical potential releases the organisms for further processing.

Microorganism Magnetic Concentration

In one embodiment, the concentration method is magnetic field capture. In this embodiment, similar to electrophoretic tags, a magnetic tag is utilized. Examples of such particles include Estapor particles from Bangs Laboratories (Fishers, Ind.), and Dynabeads from Dynal, Inc. (Norway). As described in U.S. application Ser. No. 10/888,828, these paramagnetic particles are preferably less than 1 micron in diameter, and more preferably less than 250 nm in diameter, and most preferably less than 100 nm in diameter; in general, the smaller the particle, the less it interferes with the diffusion of the microorganism to the detection surface(s). Instead of electrodes, the placement of permanent or electromagnets either above or below the detection surface allows the concentration. These magnets can be either "on-chip" or "off chip"; that is, they may be part of the biosensor cartridge, for example placed on the opposite surface from the detection surface, or as part of the device into which the biosensor is placed for manipulation or detection. Magnetic particulates including but not limited to ferrofluids and suspensions of small magnetic particulates of a size comparable to the size of a single magnetic domain can be bound to target in order to increase the net magnetization of the target and accelerate concentration. Furthermore, in the cases of target organisms of cellular nature, the magnetic particulates may be designed to have a faster rate of permeation into the organism as opposed to the rate of permeation out of the organism. Furthermore, the magnetic particulates may be designed to be irreversibly contained within the target organism. Most preferably the magnetic particles are super paramagnetic and of size comparable to a single magnetic domain.

Recirculation

In one embodiment, the concentration method is recirculation. That is, within a closed system, generally one or more channels containing one or more detection surfaces, recirculating the bulk sample through the channels and past the detection surface(s) will result in a higher percentage of microorganisms being concentrated at the detection surface(s). In general, these techniques utilize bulk flow methods relying on the use of pumps (either on-chip or off-chip) or mixers and optionally valves, such as duck bill values or differential fluidic valves, to have the bulk fluid flow in one direction This generally allows the microorganisms to be distributed along the surface, and can further allow for a larger fraction of the microorganisms to bind where there are multiple regions of potential binding. If these regions have different specificity for different species of microorganisms within the sample, then this allows the microorganisms to be moved from region to region until it contacts the region with the matching specificity.

Sample Aliquoting and Dynamic Range

It should be noted that the number of microorganisms in the sample can range over many orders of magnitude, but the dynamic range of the methods and device for the capture, growth and identification of the microorganisms may have a much smaller dynamic range. If the sample is dilute, then the entire sample will be preferably used in the subsequent analysis. However, if the sample is concentrated so that direct application would saturate the dynamic range of the device or method, then the sample will need to be diluted prior to application.

In order to determine the concentration of the microorganisms in the sample, a number of different methods are available. For example, the absorption of light is indicative of the concentration of microorganisms in solution. Alternatively, upon the concentration of organisms onto a surface according to the methods above, the surface can be imaged with an optical system and camera, and the field of view analyzed for the presence of microorganisms (e.g. by the ImageJ image analysis toolset from the National Institutes of Health, by the IMAQ image analysis toolset, or other commercial or proprietary tools, as necessary). Also, the microorganisms on a surface can be scanned with a scanning laser system, and the light scattering can be used to indicate the presence of a microorganism. Furthermore, the microorganism can be treated with an absorptive or fluorescent dye, and the total amount of absorption or fluorescence can be used to provide a rough estimate of the number of microorganisms on the surface. It should be noted that the number of microorganisms does not need at this stage to be quantified very accurately, and obtaining numbers of microorganisms within a factor of 2-3 fold is generally adequate in order to send to the system the correct number of microorganisms. The selection of a specific fraction of microorganisms can be performed in a number of different ways. In its most simple form, the sample can be manually withdrawn and possibly diluted, and an aliquot can be placed into the next part of the system manually. Preferably, the sample selection occurs through automatic means. For example, in a microfluidics-based device, a measured amount of the sample can be used, possibly with dilution with clean buffer.

Horizontal Forces and Flows

In addition to the concentration methods outlined herein, there are a number of different horizontal forces and flows that may be used to increase the kinetics or total binding of microorganisms to the detection surface. The methods of providing mixing, such as horizontal forces, can include physical mixing of the medium in the cell (e.g. through the use of a physical stirring mechanism, pumps, electroosmotic flow, surface wave acoustics, and other means), the use of horizontal electrophoretic forces on the microorganisms, the use of magnetic forces on the microorganisms, and other convenient means. Configurations specifically for mixing are outlined in U.S. application Ser. No. 10/888,828, particularly FIGS. 18 and 19, hereby incorporated by reference in its and their entirety. Those forces comprising bulk flow of the solution (e.g. electroosmosis, stirring, pumps, and surface wave acoustics) are particularly easy to implement. The vertical forces can comprise electrophoresis, dielectrophoresis, filtration, magnetic field attraction and other such forces as will bring the microorganisms into proximity with the detection surface.

It should be noted that the use of "vertical" and "horizontal" is used in relation to the surface of the electrodes, and is not related to gravity, up/down or other coordinate schemes. Given the orientation of the diagrams, horizontal can be understood in this context to be parallel to the electrode (or more generally, the surface on which the probe resides), while vertical can be understood in this context to be perpendicular to the electrode. Among these include electrophoretic forces, electroosmosis, acoustic waves, mechanical stirring, and fluid pumping. For example, in FIG. 4B, lateral electrodes 210 and 220 can be used to apply horizontal forces to microorganisms. In such case, the magnitude of the vertical electric field can be adjusted by the potential on the reference electrodes 195, in relation to the magnitude of the horizontal electric field from the electrodes 210 and 220.

It is also within the spirit of the present invention for the horizontal forces to switch direction, so that the microorganism moves back and forth over the detection surface. In such case, the microorganism will have multiple possibilities of interacting with the surface, and will thereby increase its binding. Also, in order to increase the amount of binding, the rate of horizontal movement can be decreased, or the rate of vertical movement increased.

With respect to acoustic waves, piezoelectric actuators can be placed either on the substrate 120 or on the cover 111 in a topological arrangement such that under a high frequency control signal, surface acoustic waves in the glass cause mass transport of the fluid in which the microorganisms is suspended. In such case, a convection current is created within the cell which maintains a constant laminar flow across the surface of the substrate 120. By alternating the control of the piezoelectric signals, periods of turbulent mixing can be alternated with periods of laminar flow.

Mechanical or electroosmotic pumping can also be used to create laminar flow across the surface 120. While mechanical pumping is convenient for larger volumes, electroosmotic pumping can be used to assist even in the case of extremely small volumes. In such case, the electroosmotic surfaces can be incorporated either into the substrate 120, or more conveniently into the cover 111, since the substrate 120 is often covered by a custom surface used primarily to bind probe 116 and to reduce the amount of nonspecific binding, and which may be a less effective surface for creating electroosmotic forces.

Capture of the Microorganisms

As is discussed herein, there are a variety of methods for the capture of microorganisms onto the surfaces of the invention. In general, these fall into two categories: specific and nonspecific capture. "Capture" in this context means that the microorganisms are associated with the detection surface(s) such that they do not significantly move or detach under the conditions of the assay. For example, this association is generally strong enough to allow washing steps without removing the microorganisms from the surface. In general, capture relies on non-covalent forces such as electrostatic interactions, hydrogen bonding, hydrophobicity, etc., although in some instances, covalent attachment (including for example cross-linking) can be done. Activated crosslinking may be achieved via thermal, light induced means.

Washing depends upon the difference in binding energies between desired and undesired materials. A practitioner of ordinary skill in the art can readily measure the binding energy differences using hydrodynamic flow and electrokinesis, as examples. By constructing such curves of binding energy for each type of substance, it is possible to optimize either single differential wash modes or combinations of such modes Non-Specific Capture of Microorganisms In general, there are a variety of techniques, including known techniques, that can be used to non-specifically capture microorganisms on the detection surface(s) (or on the preconcentration surface). As above, these techniques generally rely on hydrogen bonding, electrostatic and hydrophobic interactions, which can be used either singly or in combination.

There are a number of known materials that are "sticky" to either or both of microorganisms and/or biological molecules. These include any number of biological molecules and polymers, including, but not limited to, poly-ionic surfaces, particularly poly-cationic surfaces when the microorganisms have an overall negative charge, including polyamino acids (e.g. polylysine), and fibronectin. Furthermore, it is well known in the art that species of bacteria bind selectively to certain molecules. For example, it is well known that *Escherichia coli* binds mannose surfaces selectively. *Streptococcus* and *staphylococcus* organisms bind the Fc portion of antibodies via protein A mechanism. These receptor ligands may be utilized to immobilize bacteria on surfaces Highly hydrophobic surfaces, such as polystyrene, are generally "sticky" to microorganism and can also be used.

One polymeric surface of interest is OptiChem™, as described in U.S. Patent Publication No. 2003/0022216, which is a member of a class of "hydrogel" surfaces (including also CodeLink by Amersham) that are highly porous and which generally support, because of this porosity, the diffusion of redox mediators and interactions with the electrodes needed for the electrophoresis of microorganisms. This can be modified with particular groups to enhance non-specific adhesion, including diethylenetriamine (useful to enhance electrostatic interactions), and Tris and ethanol amine (useful to enhance hydrogen bonding). It can also be modified with hydrophobic moieties, which can include benzenes, naphthalenes, and compounds containing such moieties, which are preferably substituted with amines or sulfhydryls so that they can be conveniently linked to OptiChem or other similar hydrogels.

One of the important properties of these hydrogel surfaces is their lack of "stickiness" in their unsubstituted state for microorganisms. This makes these surfaces of particular value in coating surfaces of the devices of the present invention in areas where the microorganisms are not desired to bind, including, for example sample introduction wells, vias and channels, and even electrodes to which the microorganisms are not desired to bind, such as concentration electrodes.

Specific Capture

In general, one aspect of the invention provides for specific capture binding ligands attached to the detection surface(s). "Specificity" in this case will vary with the application, assay and sample. In some embodiments, it may be desirable to have an assay for a panel of different types of microorganisms, or for a panel of different species within a particular genus, or combinations. Thus, while non-specific capture is directed to most or all of the microorganisms within a sample, specific capture is directed to specific microorganisms. For example, it may be desirable to have specific capture ligands for different species of E. coli that will not cross-react with each other. In other cases, it may be suitable to have a capture ligand that binds to many or all E. coli strains, and another that binds to many or all species or strains of the Streptococcus genus. Combinations of these are also appropriate.

By "binding ligand" or "binding species" herein is meant a compound that is used to probe for the presence of the target microorganism, that will bind to the target microorganism. In one aspect, when labels are used, there may be two binding ligands used per target microorganism; a "capture" or "anchor" binding ligand that is attached to the detection surface as described herein, and a soluble binding ligand, that binds independently to the target microorganism and contains a label, as described below.

Generally, the capture binding ligand allows the attachment of microorganisms to the detection surface(s), for the purposes of detection. In a preferred embodiment, the binding is specific, and the binding ligand is part of a binding pair. By "specifically bind" herein is meant that the ligand binds the analyte, with specificity sufficient to differentiate between the specific microorganism and other microorganisms, components or contaminants of the test sample. However, as will be appreciated by those skilled in the art, it will be possible to detect analytes using binding that is not highly specific; for example, the systems may use different binding ligands, for example an array of different ligands, and detection of any particular analyte is via its "signature of binding to a panel of binding ligands, similar to the manner in which "electronic noses" work. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about 10-4 to 10-6 M-1, with at least about 10-5 to 109 being preferred and at least about 10-7 to 10-9 M-1 being particularly preferred. It should be noted that in the current invention, lower binding ligands can be utilized, because of the large number of interactions between an analyte the size of a microorganism and the ligand.

As will be appreciated by those skilled in the art, the composition of the binding ligand can vary. Binding ligands to a wide variety of analytes are known or can be readily found using known techniques. Antibodies to cell-surface proteins, lipids or carbohydrates are useful in one embodiment. The term "antibody" includes antibody fragments, as are known in the art, including Fab, Fab2, single chain antibodies (Fv for example), chimeric antibodies, etc., either produced by the modification of whole antibodies or those synthesized de novo using recombinant DNA technologies. The term "antibody" further comprises polyclonal antibodies and monoclonal antibodies, which can be agonist or antagonist antibodies, variant antibodies and antibodies derivatized by any number of chemical moieties, such as PEGylation. There are a number of commercially available antibodies to infectious microorganisms, see generally antibodies sold by Accurate Chemical, Biodesign, Fitzgerald, KPL, US Biological, Virostat, QED, Novus Biologicals, Cortex and Abcam, among others.

Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte, including surface moieties on the microorganisms.

In an additional aspect, the binding ligand proteins include peptides. For example, when the target on the microorganism is an enzyme, suitable binding ligands include substrates, inhibitors, and other proteins that bind the enzyme, i.e. components of a multi-enzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences. In a preferred embodiment, the binding ligands are portions (particularly the extracellular portions) of cell surface receptors that are known to multimerize. Similarly, there is a wide body of literature relating to the development of binding partners based on combinatorial chemistry methods.

The capture ligand is generally attached to the detection surface through an attachment linker, which may be a polymeric material as outlined herein, including both linear and branched polymers, or more linear linkers such as alkyl chains. The method of attachment of the capture binding ligands to the attachment linker will generally be done as is known in the art, and will depend on both the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups, thiols, aryl azides, alcohols, amines, epoxies, n-hydroxy-succinimide, biotin, avidin, and thiol groups. These functional groups can then be attached, either directly or indirectly through the use of a linker. Linkers are well known in the art; for example, homo- or hetero-bifunctional linkers as are well known (see 1994 Pierce Chemical Company catalog, technical section on cross-linkers, pages 1550200, incorporated herein by reference). It should also be noted that these same methods can be used to add labels to soluble binding ligands for detection, as outlined below. Furthermore, it is well known in the art that species of bacteria bind selectively to certain molecules. For example, it is well known that *Escherichia coli* binds mannose surfaces selectively. *Streptococcus* and *staphylococcus* organisms bind the Fc portion of antibodies via protein G or protein A mechanism, respectively. In addition, other types of bacteria may have binding sites, such as adhesins on fimbriae, that have preferred attachment substrates, such as specific polysaccharides or proteins. In such cases, capture may take place by providing such naturally preferred binding substrate zones.

Spacing

In one aspect of the invention, the spacing of the microorganisms on the surface is controlled. Bacteria electrophoretically transported from bulk solution to a surface tend to form semiorganized clusters on the surfaces, due to electrohydrodynamic flow. For QM purposes, a majority of the cells should be associated with the surface at individual discrete sites, that is, clustering is limited. There are a variety of ways to accomplish this. In one aspect, the viscosity of the electrophoretic solution is increased by adding a viscosity agent. Suitable viscosity agents include glycerol, saccharides, and polysaccharides such as dextrans, and polymers such as polyethylene glycol, These agents can be added at different concentrations, depending on their viscosity; for example, 10-25% glycerol, with 20% being a particular aspect, is useful. In some cases, other reagents may be added to reduce this "clustering" effect, optionally in conjunction with viscosity agents and the techniques outlined below. For example, surfactants, proteins such as albumins, caseins, etc., specific inhibitors of cellular adhesion, polymeric materials such as polyethylene glycol, and dextran can be added to reduce the clustering.

In another aspect, fluidic design and electrokinetic electrode geometry may be advantageously employed to provide or augment the spacing of the microorganisms on the surface.

In yet another aspect, the spacing of the microorganisms on the surface is done by controlling the density of either the specific capture ligands or the components that contribute to non-specific binding on the detection surface(s). For example, when specific capture ligands are used, the concentration of the ligand on the surface is controlled to allow a spatial density that allows the binding of individual microorganisms at discrete sites that are spatially separated. In one aspect, the separation distance is greater than the diameter of several microorganisms, such that a single microorganism bound at a discrete site can undergo several cycles of cell division and still be detectably distinct from other microorganisms bound at neighboring regions. The density of the capture ligands will depend in part on the size of the microorganism to be evaluated, as well as the concentration of the microorganism in the sample. As noted earlier in this specification, the number of microorganisms added to the system for binding to the capture surface can be regulated, In general, the number of microorganisms should be balanced with the size of the capture surface such that the center-to-center distance between the microorganisms has as a median at least 10 microns, and more preferably 20 microns, and even more preferably 40 microns. This distance will ensure that even after a number of divisions, wherein the sibling microorganisms from a single founder will number 16 or 32, most minicolonies (called here "clones", as discussed in more detail below) will remain distinct and not overlapping.

In some cases, electrophoresis under certain of the conditions outlined herein results in an inhomogeneity of dispersion of the microorganisms on the detection surface, as evidenced by areas of concentration and rarefaction of cells. This has been observed under conditions of 10 mM benzoquinone and 10 mM hydroquinone, an indium tin oxide (ITO) electrode separation of 300 microns, and a potential of greater than 1.5 Volts and less than the breakdown voltage of the ITO. There are several methods that can be utilized to control this phenomenon. In one aspect, the strength of the electrophoretic force can be reduced, either by decreasing the voltage, or by increasing the conductivity of the solution. For example, in a solution of 10 mM benzoquinone and 10 mM hydroquinone and very low conductivity (e.g. <100 mS/cm), the cells do not appear very strongly below 1.4 volts. In an additional aspect, periods of strong electrophoretic force can be interspersed with periods of lesser or no electrophoretic force, wherein the amount of lesser electrophoretic force is preferably less than 50% of the maximal force, and more preferably less than 25% of the maximal force, and is most preferably less than 10% of the maximal force. In general, the period of strong electrophoretic force should be less than that at which the cells first form, and such periods are preferably no more than 5 seconds, and more preferably no more than 2 seconds, and most preferably no more than 1 second. The periods without electrophoretic force are conveniently substantial enough to allow diffusion of ions to distances large compared with the vertical size of the cells (i.e. the distance between the electrodes), and are preferably more than 100 milliseconds, and more preferably more than 300 milliseconds, and most preferably more than 1 second. In a further aspect, it is convenient to allow liquid flow to break up the cells, such as through the use of temperature convection aided by unequal heating of the walls of the chamber, or through movement of fluid through the chamber, for example mixing or washing.

It can also be beneficial in certain circumstances to have the bacteria distributed in a non-uniform manner on the detection surface. For example, in the case where the number of bacteria can range over numbers larger than the nominal range of the system with uniform distribution of bacteria, by having a non-uniform distribution on the detection surface, areas of relative paucity of bacteria can be used when the number of bacteria in the sample is high, whereas areas of relative concentration can be used when the number of bacteria in the sample is low.

In one aspect, several of these techniques are combined together. For example, the capture ligand density can be controlled and a viscosity agent can be used. Similarly, intermittent electrophoresis in the presence of a viscosity agent can be used.

Washing

As will be appreciated by those in the art, any number of optional washing steps can be used during the methods of the invention.

In one aspect, washing step(s) are done to remove loosely-bound exogeneous materials, and can include, but are not limited to, different salt concentrations different pH conditions, or other chemical or physical treatments, including the use of high force/pressure washes. These wash(s) can also be done to exchange buffers to increase binding affinities.

In one aspect, washing steps are used to discriminate binding affinities of the targets to the detection surface(s), both non-specific binding as well as specific binding. That is, different microorganisms (as well as contaminants) may associate with the detection surface(s) with different binding affinities. In some cases, washing steps can be used to discriminate between different entities, e.g. washings corresponding to a number of binding energies can be used (reference is made to FIG. 9 of U.S. application Ser. No. 10/88, 8828, and the corresponding legend and discussion, incorporated by reference). It should be noted that the use of electrophoretic forces can be used in both accelerating the reaction as well as in providing discrimination between specific and nonspecifically bound material. It should be understood, however, that it is within the spirit of the present invention that in a given application, both uses of the electrophoretic forces acting on target-probe complexes, or alternatively, only one or the other of these uses of electrophoretic forces can be used to beneficial effect.

In one aspect, washing steps are used to provide new nutrients for growth conditions. That is, there may be one buffer system for use in the electrophoretic concentration step which is exchanged after the binding to the detection surface(s) has occurred. Alternatively, the electrophoretic buffer system is constant, due to the sporadic pulse of electrophoretic force during growth to keep daughter cells in the vicinity of the founder cell, but the nutrients for growth are consumed, requiring buffer exchange.

It should be noted that in the preceding discussion, the use of each antibodies or other markers for identification can be used in both manners as described elsewhere in this specification. That is, the microorganisms can be identified with the antibodies either through staining processes, or alternatively, through the use of different regions on the capture surface to which specific antibodies are adhered, and to which then specific microorganisms will be bound.

Growth of the Microorganisms

Once the microorganisms have been associated with the detection surface(s), they are now grown in order to determine their viability, growth characteristics, and susceptibility to various agents (such as antibiotics). The growth occurs by the incubation of the microorganism in the presence of a suitable medium at proper temperatures and oxygen saturation or depletion (e.g. for anaerobic or aerobic bacteria, depending generally on the source of the sample). The incubation medium will be in general matched to the bacteria being monitored—for example, lung aspirates, urine samples and blood samples would all be incubated with media that are well suited for microorganisms of the respective origins, as is well known in the art. In addition, the antimicrobial agents to be tested for effects are also well-known in the art, and will change with the discovery of new agents and as the mix of current agents in use changes with the advent of resistance.

As outlined herein, during the growth of the bacteria, it can be optionally convenient to apply a continuous or frequent electrophoretic force, in order that daughter or new microorganism are in roughly the same location as the original microorganism from which they are derived. This allows the determination of which of the original microorganisms are growing, and it secondarily allows the determination of the type of microorganism without having to do additional tests (e.g. antibody staining).

It should be noted that the electrophoretic force experienced by the bacteria is inversely related to the conductance of the medium, and therefore it is convenient to have a low conductance growth medium. Most media used for the growth of bacteria, yeast, and other organisms, however, generally has $Na+$, $K+$, $Mg+2$, $Cl-$, $SO4-2$, $NO3-$ and other ions as both nutrients as well as to maintain an ionic strength of the medium. It is preferable for the growth medium to have a conductivity of less than 5 mS/cm, and more preferable for the growth medium to have a conductivity of less than 2 mS/cm, and even more preferable for the growth medium to have a conductivity of less that 1 mS/cm. It should be noted that these conductivities are generally higher than that used in movement of bacteria and other molecules for concentration of these at the electrode, as described above. However, because the daughter microorganisms are created at or proximal to the electrodes, the movement required is small in distance, and lower amounts of electrophoretic force are required. In addition, the application of the electrophoretic force need not be constant, and can be applied intermittently, especially in those cases where the growth medium is not under constant bulk movement. Because of the slow diffusion of microorganisms, it is preferable to apply electrophoretic force when the medium is not in bulk movement no more frequently than every 10 seconds, and even more preferable no more frequently than every 60 seconds. In general, many growth media contain large amounts of salt (e.g. 0.5% NaCl in L Broth), and it is preferred that this salt be replaced by a zwitterionic species, such as alanine or cysteine, that contributes very little conductance. It is also preferable for the osmotic strength of the medium be high enough so that the bacteria do not undergo osmotic shock. Non-ionic osmotic components, such as glycerol or sucrose, can be used for this purpose.

Positive growth by itself indicates primarily the viability of the organism, and potentially the relative rates of growth of the microorganism. However, it can also be used to study the susceptibility of the organism to various anti-organism agents as outlined herein, and combinations thereof. In addition, the clonal relatedness of individual organisms that grow during testing substantially improves the sensitivity and specificity of certain tests. Statistical tests based on clonal relationships thus add power to the tests performed by the present invention.

Detection and Identification of the Microorganisms

The monitoring of the binding and/or growth of the microorganism can be performed for an average of all of the material that is bound—for example, measuring the total output of light that is scattered from a tag that has a light scattering indicator. However, if the detector is an optical detector, and the detector is an imaging detector such as a camera or a laser scanner coupled with a photo multiplier tube, it is also within the spirit of the present invention for the binding to be determined for individual microorganisms. In this case, the detector will need to store the locations of each microorganism between sequential detections and determine growth. A variety of methods are described herein.

In addition, one useful method of the invention utilizes both brightfield and darkfield images, as the combination of these techniques allows the discrimination of microorganisms from contaminant debris. Debris often looks similar to bacteria in darkfield because of similar scattering efficiencies (e.g. the change in refractive index times the cross sectional scattering area) as bacteria but in brightfield absorptive properties between bacteria and debris can be dramatically different. For example, in many cases the debris are visible in brightfield imaging and the bacteria are not.

There are a wide variety of methods suitable to detect and identify microorganisms, including methods that include labels and methods that do not.

Use of Labels in Detection and/or Identification

In one aspect, detection of the microorganisms is done using detectable labels that can be either specific or non-specific. That is, just as for the capture of microorganisms on detection surface(s), the labeling of the microorganisms for detection can be specific to the type (e.g. species or genus) of microorganism, or can be non-specific, e.g. will bind to a number of different microorganisms. Thus, the detection moiety has two components: a binding component and a label component. Binding components can be independently selected from the moieties outlined above for capture ligands.

As will be appreciated by those in the art, there are a wide variety of available labels which will be tailored to the type of detection used. Suitable labels include, but are not limited to, enzyme indicators; optical labels including but not limited to optical dyes, fluorescent dyes, upconverting phosphors, quantum dots, light scattering particles, light absorbing particles (e.g. colored particles), or phase contrast particles (i.e. to confer index of refraction differences that can be visualized in a phase contrast microscope or by surface plasmon resonance), chemiluminescent indicators; electrochemical (e.g. redox) indicators; radioactive indicators, etc. Up-converting phosphors are particles that convert lower frequency light into higher frequency light (see Orasure Technologies, Inc. of Bethlehem, Pa.), and are convenient to use due to the few natural compounds having this property, leading to generally low background in detection assays. Quantum dots function much in the same way as fluorescent dyes, but with a considerably larger shift between the excitation and admission frequencies. This large shift allows the use of higher efficiency optical filters that reduce the amount of background noise in a detection assay. An example of quantum dots is the nanocrystals produced by Quantum Dot Corp. (Hayward, Calif.). Direct visualization particles can be metallic (e.g. gold), ceramic, colored glass, or other opaque or largely opaque material and is conveniently at least 250 nanometers, and more preferably at least 500 nanometers, so that it is visible via light microscopy. An example of such a light scattering particle 294 is resonance light scattering particles by Genicon (San Diego, Calif.).

Many of these indicators can be used with optical detection systems which are matched to that of the indicator. Thus, for example, fluorophores, quantum dots, and upconverting phosphors, paired excitation illumination (e.g. laser excitation or broad-spectrum illuminators with bandpass fitters) and emission-specific detectors (e.g. bandpass filtered) are utilized along with proper imagers (e.g. cameras with or without magnification optics). Light scattering particles will often use oblique incident illumination (including standard darkfield condensers) or evanescent illumination, or may alternatively use phase contrast optics, since particles with sufficient difference in refractive index to give rise to phase optical effects will also give rise to light scattering. In addition, the phase contrast particles will also generally be visible in surface plasmon resonance. Phase microscopy can be used for phase contrast particles, and light absorbing particles and enzymatic reactions can be used in both phase contrast microscopy and brightfield imaging (e.g. with microscopic imaging or other forms of magnification). Chemiluminescence can be detected with proper magnification and detectors arranged to have the proper receptivity to the chemiluminescent signal. The descriptions above are not exhaustive, and other combinations of indicator and detector are within the spirit of the present invention.

QM can use techniques such as affinity binding to identify individual organisms by species. In one embodiment, the surface capture agent itself is a specific affinity agent (such as an antibody) immobilized into a discrete zone mapped onto an observation surface. A plurality of such discrete capture zones then provides an array of different affinity agents directed at different microbial species or groups. After capture and stringent washing to remove nonspecifically adsorbed materials, the organisms that remain on each zone are those against which the zone's specific capture agent is directed. The zone map reveals the identity.

For example, a "panel" or specific set of bacterial species for a suspected type of infection might include *Staphylococcus aureus, Streptococcus pneumoniae, Haemophilus influenzae, Pseudomonas aeruginosa*, and so forth. A QM array would then consist of high affinity antibodies, aptamers, or other affinity-binding agents developed against these particular species and immobilized on the analytical surface, each in a discrete zone, according to a mapping scheme, such as a linear arrangement in the sequence just described.

As additionally described below, in order to detect the captured organisms, a QM detector use a device such as a digital microscope that provides electronic images suitable for analysis by a computer. The image analysis program then analyzes each image according to algorithms developed for the purpose of identifying individual organisms. As the computer analyzes the images for each mapped zone, it scores organism recognition events, records their identity by virtue of the zone identity being analyzed, and records their spatial coordinates. The QM system thus creates a spatial map of each identifiable organism, implicitly linking each organism's location to its group identity, such as species.

This form of mapping occurs very quickly during or immediately after capture by the use of high-speed computing. It therefore adds insignificant time to the analysis.

In an additional embodiment, as described herein, the capture agent is not specific, but captures all organisms in a single discrete zone of immobilized binding agent. In this mode such a capture agent does not allow direct identification, as does the mapped array form.

Instead, in one aspect, this QM mode applies specific agents, such as those described for mapped capture, but in free solution or suspension and conjugated to a measurable moiety such as a fluorescent dye, light-scattering particle, and so on. After exposure to the captured organisms, brief incubation, and wash, affinity labels remain bound to their cognate ligands or targets. The QM detector is designed to identify such labels at the scale of individual organisms, operating in a manner to that described for the specific capture image analysis mode, including mapping the location of each organism and its group identity.

This labeling and analysis step typically requires considerably less than thirty minutes to complete.

In addition, negative growth (e.g. necrosis) can be determined using mortal stains as outlined herein.

Methods not Relying on Labels

For the detection of microorganisms not relying on the use of labels (either capture ligands or labeling ligands), in general optical techniques, as outlined herein, are used to monitor growth, including positive, neutral and negative growth.

Anti-Microbial Assays and QM

Approximately half of antibiotics require bacteria to be actively in cycle (positive growth) in order to exert their antimicrobial effect. Therefore, prior to the application of AOAs as described hereunder, it is generally preferable, at least for those AOAs for which positive growth is needed, for the microorganisms to be grown for at least one, and preferably two or more cell divisions prior to the administration of AOAs. These cell divisions can be monitored directly by image analysis as described elsewhere in this specification.

In the simplest case, this involves the incubation of the organism in a constant concentration of anti-organism agent (AOA), and determining the rate of growth and/or the rate of death of the organism. FIG. 33E shows how this would be performed with the present invention. In FIG. 33D, the bacteria 830, 835 and 840 have been specifically bound to capture surfaces 820. After a period of incubation in one concentration of an AOA in a growth medium (indicated by light stippling), the bacteria 840 have increased in number, and the bacteria 830 and 835 have not, indicating that the bacteria 840 are not susceptible to AOA at the concentration used, and that the bacteria 830 and 835 are susceptible at the concentrations of the AOA used. It should be noted that bacteria 835 are of the same type as bacteria 830, except that they are dead. Given a mortal or vital stain, therefore, it can be determined that bacteria 830 have not been killed by the concentration of AOA, indicating either that AOA prevents positive growth but does not kill the bacteria 830, or that at the concentrations used, AOA only acts to stops positive growth (neutral growth).

In FIG. 33F, the concentration of the AOA is increased, and the number of bacteria 840 still increases, indicating that the bacteria 840 are non susceptible to the bacteria even at this concentration. However, now the bacteria 830 have been killed (indicated by the dead bacteria 835), indicating that at this concentration, AOA is lethal. Thus, as indicated in FIGS. 33E-F, by using increasing concentrations of the AOA in the growth medium, the concentration response of the bacteria to the AOA can be determined. Clearly, by increasing the amount of AOA in steps over a period of time, a minimum inhibitory concentration (MIC) can be determined. In addition, because viability of the bacteria can also be determined at each concentration, a minimum bactericidal concentration (MBC) can also be determined.

It should be noted that organizations such as the National Committee for Clinical Laboratory Standards (NCCLS) have standardized rigorous procedures for determining MIC using gold standard methods and have circulated a draft proposal for standardizing procedures for determining MBC.

It should be noted that the detection of growth (including viability) at different concentrations of AOA can be performed either by using a series of chambers 805 in the cell 804, each of which challenges the bacteria with a specific concentration of AOA, or alternatively, by increasing the concentration within a given chamber 805. In the former case, the time response of the bacteria can be easily established, as well as the persistent response of the bacteria once the AOA has been removed (e.g. a post-antibiotic effect). That is, the bacteria can also be challenged with a given concentration of AOA for a brief period, and then the medium replaced with a medium lacking the AOA, and the growth of the bacteria can be monitored over time.

As described above, so as not to use separate chambers 805 for every different concentration of AOA, the concentration of AOA within a chamber 805 can be increased over time. FIGS. 38A-B are graphs of the response of bacteria to a changing concentrations of AOA. In FIG. 38A, the concentration of AOA is increased over time, generally according to an exponential increase with time, although it is also convenient for the concentration to increase linearly or according to other concentration/time relationships, including step functions increasing the concentration; these step functions can be placed at regular concentration intervals, or alternatively at standard concentrations as indicated or suggested by clinical laboratory standards as might be set by organizations such as the National Committee for Clinical Laboratory Standards. The system is then used to determine the total number of bacteria, the number of dead bacteria, and the number of live bacteria (as described above, any two of these numbers gives rise to the third number).

The relationship of AOA effect to the growth of microorganisms has many different meanings in conventional use. For example, the visual LLOD for the microdilution method of the ASM Handbook might require the inoculum of $5 \times 10^4$ CFU per well (concentration of approximately $5 \times 10^5$ CFU/mL) to grow to approximately $1 \times 10^6$ CFU ($1 \times 10^7$ CFU/mL, cited by M. Mueller et al., Antimicrob. Agents Chemother., 48:369-377, 2004). This amount of increase represents net positive growth of approximately a factor of twenty times within the observation period. Negative findings would include any amount less than this. In this context, it would be preferable to declare positive growth inhibition to occur if net aggregate population change, during a counterpart period, to be less than the factor of twenty times the starting population. Positive growth rates less than threshold score as "growth inhibition" and higher rates score as drug failure.

At the point that the total number of bacteria does not continue to increase, indicated in the figure at the concentration A, is considered to be a minimum concentration that inhibits bacterial positive growth (MIC). The point where the number of live bacteria begins to decline (at the concentration B) is considered to be a minimum concentration that is bactericidal (MBC). It should be noted that the actual MIC and MBC can be lower than the concentrations A and B respectively, and will only be the MIC and MBC in those cases where the rate of increase in concentration is very slow relative to the positive growth of the bacteria. Thus, given that it is desired that the MIC and MBC of AOA be determined within a factor of X, it is preferable for the concentration of AOA to increase by a factor of X no faster than half the doubling time of the bacteria under the conditions of the incubation lacking AOA, and it is more preferable for the concentration of AOA to increase by a factor of X no faster than the doubling time of the bacteria, and it is most preferable for the concentration of AOA to increase by a factor of X no faster than twice the doubling time of the bacteria. It should be noted that MIC's and MBC's generated using these methods may not correlate exactly to standard MIC's and MBC's defined by organizations such as the NCCLS.

The less positive growth of bacteria required in order for there to be high confidence that positive growth has occurred will reduce the time needed to perform a test. By monitoring individual bacteria, positive growth can be seen with the doubling of only a small number of bacteria. That is, if looked at in bulk as in conventional turbidity assays, for example, the limit of sensitivity of detecting bacterial positive growth is limited by the signal to noise ratio in the turbidity measurement. However, the fission of a bacterium is a discrete event that can be detected, even if that bacterium is one of many thousands of bacteria. Thus, the present invention can have a very high sensitivity, with the system preferably able to detect doubling of less than 25% of the bacteria, more preferably able to detect doubling of 10% of the bacteria, and most preferably able to detect doubling of 5% of bacteria. Note that the doubling time for a fraction of the bacteria can be either predetermined (e.g. by calibration in a laboratory with experimental specimens), or more preferably, by comparing the bacteria in the absence of the AOA with those in the presence of the AOA—this makes the results internally controlled.

The measurement cut-off points for determining antibiotic susceptibility can be, as discussed above, be expressed in absolute terms, such as the doubling of a given percentage of the bacteria. However, the number of bacteria required to make a statistically valid judgment can be dependent on the number of bacteria present in the sample. For example, if there are only 10 bacteria present in each chamber, evidencing a single bacterium doubling represents 10% of the sample. Alternatively, with very large numbers of bacteria on the surface (e.g. more than 100,000), the doubling of even 1,000 bacteria (i.e. 1%) is usually statistically significant. Thus, it is in many cases preferable to analyze the number of bacteria required to show doubling in the control condition (i.e. growth medium absent the AOA) relative to the number of bacteria showing doubling in the experimental condition (i.e., growth medium with the AOA) as to be statistically relevant. For example, a conventional method would be to apply a chi-squared test to these two numbers, and to decide whether the results met a particular probability of significance. In general, it is preferable for this probability to be less than 0.05, and even more preferable for this probability to be less than 0.025 and most preferable for this probability to be less than 0.01. Because small numbers of bacteria will not permit very small chi-squared probabilities, the standards for probability can be conveniently reduced for cases of very small numbers of bacteria (e.g. less than 20 viable bacteria in the growth medium control).

It should be understood that the doubling time of bacteria is a population phenomenon, and that within a population of bacteria, some bacteria will divide more quickly that others. This could be due both to slight genetic differences in a population, or purely statistical effects. However, it can also be due to the stage at which each bacterium is growing during its harvest or preparation, as the bacteria will exhibit substantially different lag times in their positive growth when placed in new medium depending on that stage. While a longer period of time is generally going to provide more information about the growth characteristics and AOA susceptibility of the bacteria, there is a need to supply to medical personnel information about the bacteria and their susceptibility to AOAs. Given that average lag times for most of the bacteria of interest on the order of 2-6 hours, and the doubling time of the bacteria are generally 1-2 hours, it is preferable for measurements of bacterial growth and susceptibility to AOA use detection of the bacteria at no more than 8 hours, and more preferably less than 6 hours. Even if not all bacteria in a sample have an opportunity to demonstrate doubling, a large enough fraction of those bacteria will have so as to be able to indicate susceptibility.

In this case, it is useful to have all information available for individual bacteria relating to vital and/or mortal staining (indicating live versus dead bacteria), as well as growth in the presence of growth medium with and without the presence of AOA. Any observation in which the fraction of live bacteria decreases by a first predetermined fraction in the presence of AOAs, or in which the positive growth of bacteria (evidenced either by doublings or by increases in the size of the bacteria) is decreased by a second predetermined fraction in the presence of AOA, are evidence of the action of the AOA. In general, the first determined fraction, because of its evidence of higher death, will generally be smaller than the second predetermined fraction. A preferable value of the first predetermined fraction is 20%, and a more preferable value is 33% and the most preferable value is 50%. A preferable value for the second predetermined fraction is 50%, and a more preferred value is 66%, and a most preferred value is 80%.

As indicated above, most studies on AOA susceptibility relate to the concentration at which a particular effect is encountered, rather than the specific kinetics and effects that are observed. That is, in conventional tests, the bacteria are usually challenged with a number of different concentrations (or even changing concentrations) of AOAs to determine the concentration at which the bacteria exhibit death or lowered rates of positive growth, from which the MIC or MBC are determined in accordance to established standards from organizations like the NCCLS. Consider, for example, a conventional antibiotic test employing an agar plate with an antibiotic disk. Around the disk are colonies of various sizes, representing not simply death, but slower growth in the presence of differing concentrations of antibiotic. By this measure, the MIC is not easy to define, since incubating the plates for an extended period of time would allow colonies to appear at concentrations that are considered inhibitory.

However, both from a standpoint of time and cost, it can be convenient in some cases to instead challenge the bacteria with single, constant doses of the AOA, and then to observe the specific effect and rate of effect of the drug, in order to determine susceptibility. In the present invention, a constant dose of AOA can be provided, and the rate at which bacteria are killed, or the degree to which their positive growth is reduced, can be used to gauge the likely effects at a multiplicity of therapeutic doses. These responses can be described with new measures of AOA effect, such as the bacterial doubling time in the presence of an AOA divided by the bacterial doubling time in the absence of the AOA. In this case, for bacteria that are resistant to an AOA but whose doubling time is tripled in the presence of the AOA, treatment with the AOA can still be meaningful. These values can be provided either at a single dose, or at multiple doses. To the extent that bacteria of differing levels of susceptibility can be isolated and studied, the information at one or more concentrations of the AOA can be useful in then predicting the response at other concentrations.

In a direct counterpart to conventional antibiotic susceptible testing, the present invention uses drug exposure at two breakpoints for each species/drug pair as specified by the Clinical and Laboratory Standards Institute (www.clsi.org) publication M100-S15. This version does not provide MIC but does provide SIR categorization (susceptible, intermediate, resistant). The MIC counterpart uses parallel analyses at doubling dilutions, in the same range and manner as the conventional microdilution assay. However the present invention can use the growth rate response of individual organisms as in the SIR variation.

In addition to the counterparts of conventional AST, the methods of the present invention can also use a high drug concentration (well above the upper CLIS breakpoint) to reveal very minor resistant clones. The exact concentration for each species/drug pair is determined on the basis of the drug's mode of action. For example, resistance provocation testing for beta-lactam antibiotics uses concentrations above the upper breakpoint but below the concentration at which the so-called "paradoxical effect" or "Eagle effect" occurs.

In the provocation test, the drug concentration should quickly arrest positive growth in all founders and clones. However, if individual cells continue to divide repeatedly within individual clones, analysis quickly detects drug failure and reports the number and proportion of minority clones that exhibit resistance.

The present invention includes at least two ways that provide substantially higher sensitivity for resistance detection than is now possible using other methods. First, the methods analyze substantially all organisms or a very large number (at least 1,000, and preferentially more than 10,000) of organisms from the original specimen. Standard culturing methods typically use only about 3 to 20 original organisms, which are selected after enrichment and isolation. Therefore QM eliminates the sampling error inherent to standard culturing methods.

Additionally, the QM methods of the present invention use provocation testing with individual clone statistics to identify even a single resistant clone. QM uses the relatedness of individual cells, by virtue of their clonal derivation, to statistically increase analytical sensitivity.

For example, QM methods can detect a single resistant clone against a background of 10,000 clones (0.01% or 100 parts per million) or more that are susceptible. Standard methods that use, for example, colony isolates that represent 10 founder CFUs can on the average detect only one resistant founder in 10, or 10% detection sensitivity. Among other reasons, this sampling error helps to explain the poor clinical record of standard culturing methods to detect "cryptic growth" (invisible resistant minority strains) or "persisters" as is well recognized in the clinical research literature.

QM uses the periodic mortality counts to compute a so-called "time-kill curve" (TK) with great precision and differentiated according to component clone responses. The clone response for resistance is based on the probability of individual cell divisions in a contiguous cellular cluster in comparison with the average population or most-susceptible statistical cluster independent cellkill probability. When the positive growth rate within a contiguous cell cluster statistically exceeds that of the surrounding reference rate, QM scores the clone as resistant.

QM analyzes statistical clusters of kill rates (by clone) and aggregates the data to determine overall kill rate. Time-kill (TK) curves for each species/drug pair have statistically stereotypical forms. Therefore QM methods use the first statistically significant time-kill data points to select the corresponding reference curve, and then the maximum kill rate for that standard curve. QM reports this maximum kill rate (logarithm of the maximum number of cells killed per hour).

In addition, TK standard curves correlate with the MIC as determined using standard culturing AST methods. Having selected the best-fit TK standard curve, QM methods then look up the corresponding MIC and report it.

QM methods require only a few hours to complete because of their ability to predict endpoints based on the responses of individual cells and clones. In addition, QM methods report data that have much more predictive power than the standard MIC value alone. For example, the clinically optimum drug to use in treating an infection is the one that kills the pathogens most quickly and with the fewest intervening cell divisions prior to eradication.

MIC alone does not provide this information. Given two or more drugs that have MICs well within the susceptibility range, the physician must determine which of them is most likely to eradicate the infection and kill pathogens most quickly. The MIC does not contain this information. QM, in contrast, provides direct comparison data for all clinically useful parameters.

It should be noted that the AOA effects on positive growth (e.g. doubling time) in addition to information regarding the rate of microorganism death provide sufficient information to predict results in an standardized NCCLS test format. For example, the NCCLS broth microdilution MIC determination involves the exposure of a standardized inoculum to a concentration of AOA for a defined period of time under rigorously controlled environment. An organism susceptibility is defined as the minimum concentration at which microorganism positive growth is impeded below the threshold limit of detection. Thus given an AOA that effects microorganism positive growth rate only has a critical growth rate at which above this concentration the organism will exceed the threshold for detectable positive growth. Additionally, and AOA that effects organism viability and not the organism growth rate will have a critical viability threshold at which an organism will not exceed threshold for detectable positive growth. Furthermore, it is likely that the AOA will affect both the positive growth rate and viability of a population of organisms. Therefore, correlation of before mentioned kinetic measurements of positive growth rates and viability with standardized NCCLS MIC and MBC methods can predicted from modeling bacteria positive growth and viability modeling.

It should be noted that the concentration of AOA in a human or animal is determined by the amount and frequency of treatment (e.g. injection), as well as the AOA pharmacokinetics. In many cases, the pharmacokinetics are well-known for disease-free humans, and can be modeled on the basis of the known medical state (e.g. liver failure) of the person being monitored. Using this information, the concentration of AOA over time in the target organ (e.g. blood, urinary tract, lungs) can be estimated. This AOA concentration can be approximated in the chamber by mixing medium with AOA in relative parts with medium lacking AOA, to produce the estimated profile of AOA such as that shown in FIG. 38B. In general, the concentration of AOA will rise, peak, and then exponentially decay. As before, the total number of bacteria, the dead bacteria and the live bacteria can be monitored over time. In this case, the pharmacodynamic parameters MIC and MBC are not well defined, since one is looking at the response to the bacteria including the pharmacokinetics of AOA, and one looks therefore at the minimum inhibitory dose and the minimum bactericidal dose by running replicates of the system at different doses, and then monitor if the overall AOA concentration profile results in the cessation of positive growth or the death of the bacteria. It should be noted that while the analysis of FIG. 38B deals with only a single dose of AOA (i.e. rise, peak, decay), it is also possible to continue the analysis on sequential doses of AOA as would often be used in treatment (e.g. injection 4 times daily).

It should be noted that the methods of the present invention can be applied not only to the response of organisms to AOA, but also the response to other conditions, such as other bioactive agents, including hormones, drugs (e.g. for drug sensitivity testing), environmental or other agents. These agents can be so analyzed, as long as the response is detectable by the detector employed. In many cases, a stain of some sort may be required in order to make the response to the condition visible.

In the discussion above, the timing of the application of AOA can be related either to the time at which the bacteria are first placed into growth medium, or alternatively, to the time at which bacterial positive growth is first detected (e.g. through changes in the size of the bacteria, or the presence of daughter cells). In the latter case, positive growth can be monitored continuously, and AOA added to the incubation at such time as it is determined that the lag time has completed. The completion of lag time will generally be that point at which some predetermined fraction of cells have shown signs of positive growth, which is preferably less than 50% of cells, and more preferably less than 30% of cells, and most preferably at less than 20% of cells.

As described above, a feature of quantum microbiology (QM) is the use of single microorganisms as an important unit of analysis. By doing the analysis on individual microorganism, a number of advantages arise. For example, the time necessary to grow the microorganisms into large numbers (e.g. for counting on an agar plate) requires considerable time, which may not be available for the treatment window for certain medical conditions. Furthermore, the analysis of large numbers of organisms makes more problematic the detection and analysis of small numbers of resistant microorganisms in the population. In addition, with certain types of analysis (e.g. the appearance of colonies on an agar plate), it is hard to distinguish at times the mortality of microorganisms from effects that increase the doubling time for microorganism growth, or which act to stop positive growth, but not to kill the microorganisms (e.g. neutral growth).

In QM, observations can be made on four different entities, sometimes simultaneously. These entities are:

individual microorganisms, either isolated or present as a part of a larger entity (e.g. a clone or a population, as described below), clones, which represent the progeny from an individual microorganism, or from a CFU, which can comprise a cluster of physically associated microorganisms.

strains, which represent all microorganisms which react with the same strainspecific antibody or other method of strain identification. The strain designation can comprise serotypes of individual species, species-wide serotypes, genus-wide serotypes, Gram-positive or negative, or any similar subset of microorganisms that can be distinguished as described in the methods above.

populations, which comprises the totality or a subset of individual microorganisms and clones all of which derive from the same medical sample (e.g. a lavage sample):

It should be noted that an individual microorganism, when it divides into two during cell division, creates two microorganisms in which, because the division is largely into two roughly equal parts, it is often difficult to label one the parent and the other the "child". Rather the two microorganisms are "siblings". It is most convenient in general with respect to QM to follow a particular individual microorganism only form division to division, and the resulting sibling microorganisms can be considered to be new individuals. Thus, in a database of microorganisms that are grown and measured by the present invention, a given microorganism is not of continuous existence, but comes into existence at the division of its progenitor, and whose existence is considered to end at its division. Alternatively, at a cell division, one of the microorganisms can be considered to be continued existence of the progenitor (e.g. the larger of the microorganisms, or the microorganism that most overlaps in position with the position of the progenitor), and the other resultant microorganism from the division considered to the be "child" microorganism.

While individual microorganisms can be distinguished by their size, shape and other characteristics from a microscopic image, clonal relationships are more difficult to establish. For example, while two microorganisms that a physically contiguous can represent members of a single clone, they can alternatively represent two microorganisms that are adventitiously physically adjacent. Thus, to establish true clonal relationships, it is preferable to have a series of microscopic images over time, in which the appearance of two microorganisms in the location where there had been only one microorganism is indicative of a sibling relationship. This relationship can be more strongly established even, inasmuch as the volume of the "parent" microorganism can increase over time, with an abrupt decrease in volume coinciding with the appearance of a new, sibling microorganism. It should be noted that the volume of the microorganism will in general not be measured directly, but rather in terms of the apparent area in a two-dimensional image.

It should be noted that some species have stereotypical multicellular clustering morphology, such as grape-like clusters for *Staphylococcus aureus* or bead-like chains of *Streptococcus pneumoniae* diplococci. Therefore, it is convenient to convert individual viable counts to CFU equivalents, as these are more akin to measurements conventionally determined, assuming that any contiguous cluster that includes one or more viable individuals counts as one CFU.

When making observations of individual microorganisms, the position of the microorganism is established. It is important for this and other measurements described below for the absolute position of the field of microorganisms be maintained, even should the test piece in which the measurements are made is moved from time to time with respect to the optical and imaging system. This absolute position can be maintained through the use of optical calibration marks on the test piece, for example, In addition to the position of a microorganism, the strain identity (as established, for example, by the identification of the microorganism by a labeled antibody preparation, as described above) can be observed. Furthermore, the doubling time of the microorganism in the absence of an AOA can be established, for example by looking for the appearance of clonal siblings (especially whose appearance is matched by a decrease in the apparent volume of the microorganism). While this doubling time can be maintained for each generation individually, this information is preferably maintained as a mean or median time interval between doublings. Given that there may be a lag time in the initial positive growth of the microorganism, which would be evidenced as an initially long doubling time, the statistical averaging (e.g. mean, median) can be maintained for only the last N doublings (e.g. by keeping a running average or median), where N is preferably less than 5, and more preferably less than 3.

Doubling time is normally measured with respect to population of microorganisms, wherein the number of microorganisms at different times (generally at fixed intervals) are measured. With respect to measuring doubling time of a particular individual microorganism, different methods can be employed. In a first method, repeated observation of the individual microorganism allows one to determine the difference in time between the prior cell division giving rise to the individual microorganism as the cell division resulting from the individual microorganism. This will give a measurement of the doubling time of the microorganism to within approximately the time interval of observation (i.e. plus or minus half the interval at each time boundary between divisions). If the observations are made every minute or two, this will provide an accurate estimate of doubling time. However, if the observations are made less frequently (e.g. every 15 minutes), then the uncertainty of the individual doubling time may be a large fraction of the actual doubling time. However, these numbers, when summed over a number of microorganisms—whether in a clone, a strain, or a total population, will average out to a highly accurate measurement of the doubling time of the entity being measured, even with relatively few individual microorganisms (as in a clone). This felicitous feature means that the doubling times of individual microorganisms can be monitored and stored, prior to the assignment of the microorganism to a particular larger entity. For example, consider two sub-strains of a microorganism that are initially labeled as being the same entity (e.g. through antibody staining). However, at some later point, it might be determined that there are actually two different substrains within the strain, which are distinguished, for example, by their AOA susceptibility. In this case, having stored the doubling times of the individual microorganisms, as they can be retrospectively assigned to the sub-strains, the doubling times of these sub-strains can be reconstructed from the beginning of the observations. It should be noted that this discussion with respect to doubling times also relates to other measurements of growth and death kinetics, such as time-kill curves.

It is of particular interest to monitor the behavior of the microorganism in the presence of an AOA. After the addition of the AOA to the growth broth, observations that can be made include the new doubling time of the microorganism, and the viability or mortality of the microorganism (where the viability and/or mortality is monitored as described above). This information will in general be maintained as an absolute time or time relative to the introduction of the AOA. The doubling time, it should be noted, will generally not change abruptly to a final state, but can change over a period of time. In general, this can be modeled as an increase in doubling time which approaches the "final" doubling time asymptotically (and which can often be modeled as an exponential approach), which allows the final doubling time to be approximated with only a few data points.

Another parameter of considerable use that is available from the observations above is the time at which the AOA kills the microorganism, which can be measured either by the loss of viability or the onset of mortality, generally observed through the use of stains as described above. This number can be of considerable interest medically, since killing removes the possibility either of the onset of resistance, or positive growth due to periods in the pharmacodynamic time-dependent concentration of the AOA falling below some threshold such that the AOA is allowed to grow.

With respect to clones of microorganisms, similar observations can be made. For example, the position of the clone can be observed, as well as the strain identity of the microorganisms comprising the clone. This position can include a number of different related parameters, which can include the positions of the perimeter of the clone, the center of mass (in X-Y terms) of the clone, and the approximate diameter of the clone. Observations about the number of cells, the doubling time of the microorganism (before and after the administration of AOA), the fraction of live and dead microorganisms, and other information can be monitored. It should be noted that with respect to, for example, the doubling time of the clone, this can be expressed either as the fastest doubling time of a microorganism within the clone, or some population number (e.g. the time for the number of microorganisms within the clone to double), or an average or median time of doubling of the individual microorganisms within the clone.

It should be noted that in order to maintain clone observations, one preferred method is to keep observations about each individual microorganism, as well as membership information about which clone each microorganism is a member, and then the clonal observations can be comprised of the appropriate information of each individual microorganism of a clone assembled with the proper information. Furthermore, with the generation of new microorganisms through the division of existing microorganisms, the store of information must be allowed to grow in order to accommodate all of the new microorganisms.

One of the advantages of looking at a clone of microorganisms as opposed to an individual microorganism is that effects of AOA administration can be more unambiguous and quantitative. For example, if an individual microorganism dies upon AOA administration, it may be because of a host of factors unrelated to the AOA. However, if some, most or all of the microorganisms that comprise a given clone are affected, then one can be confident of the effect of the AOA on microorganisms of that type. Likewise, if the doubling time of an individual microorganism increases by a factor of two upon administration of an AOA, the statistical reliability of the doubling time can be low, especially given that most samples will not be continuously monitored, but only monitored at predetermined intervals, where the intervals will generally be at least 15 minutes. However, with a clone of 32 microorganisms, for example, individual 15-30 observations of microorganisms that are doubling every 30-60 minutes will generally yield reliable doubling times even with only two or three observations.

Strain and population observations will in general be obtained through observations on clones and individual microorganisms followed by algorithmic manipulation of the data, The information that will be maintained can include the strain/serotype identity, the number of cells sharing the same identification, and the doubling time in the absence of AOA (which can include both minimal doubling time, as well as statistical averages such as means, medians, weighted means, and the like). In addition, it is of particular interest to obtain measures of AOA susceptibility, including the average/median time to kill the microorganisms, the fraction of live and dead microorganisms as a function of time after AOA administration, the fraction of microorganisms that are positively growing as opposed to fraction that are in apparent stasis (determined relative to a predetermined doubling time threshold), the doubling times of the fastest microorganisms within the particular strain or population, and the fraction of clones that are affected (i.e. with a change in viability or fractional increase in doubling time greater than a predetermined factor).

In general, two of the advantages of the present invention can be broadly stated. The monitoring of individual microorganisms and their response to AOAs provides low limits of detection, good statistics for analysis, and more reliable results. The quantitative monitoring of growth at more than one interval allows us to measure changes in growth rates and doubling times, as well as measuring the kinetics of killing and changes in growth rates, which allows us to make quantitative predictions of the growth of the microorganisms in the patient, which predictions can indicate clinically relevant parameters (microorganism burden, the appearance of resistant strains) as a function of time.

The observations for individual microorganisms, clones, strains and populations will generally be kept in a computer, which can store the information either in a database (such as a SQL database), or which can alternatively be stored in memory and binary files specific for such data. Rapid access to the information is required in order to maintain and update the data.

Other Quantum Microbiology Statistical Methods

As mentioned above, the methods of the present invention operate at many different levels, but the application of QM to individual microorganisms and clones from individual founder microorganisms are of particular benefit. This type of analysis, which can be performed on small samples sizes (at the methods limits of sensitivity, tens or even less of microorganisms or clones in a particular channel), requires different statistical analyses from conventional methods, which can be expressed as the probabilities of events.

For example, one can determine $P(+)$ as the fraction of all live cells in the sample population that divide during a standardized time interval in the presence of a fixed antimicrobial concentration. This is the probability that any particular single cell being observed during such a time period actually divides.

Similarly, $P(-)$ is the fraction of cells killed in the same standardized observation interval, and the probability that any particular single cell being observed during such a time period actually dies. Eradication is possible as long as $P(-)$ is greater than $P(+)$. Generally, conventional AST reveals results for populations in which $P(-)$ is much greater than $P(+)$. Within any susceptible clone the observations remain the same. Observation over serial time intervals will approximate the frequency distributions of the aggregate susceptible population.

However, $P(-)$ for resistant cells is much lower than for susceptible cells. By definition, $P(-)$ is much less than $P(+)$ for resistant cells. In a microbial population in which susceptible cells substantially outnumber resistant cells, aggregate population statistics require extended observation in order for the resistant population to become large enough to be detectable. However, the ability to identify members of a clone markedly increases the speed of detection.

An AOA kills large numbers of susceptible cells in such a mixed population, and a small subset of resistant cells continues to grow. By examining individual cells of known clonal relationship it is possible to calculate the kill rate within an average clone. Therefore any clone that shows statistically significant departure from the intra-clonal death rate indicates resistance.

For example, one can select conditions in which the observation interval is long enough to produce an average of one kill per interval in susceptible clones and random cell divisions (of susceptible cells) occur at substantially lower frequency, or not at all. Then, when observing each clone during AOA exposure, any clone that begins to statistically exceed the birth rate of majority clones then represents resistance. Thus the sensitivity of QM clonal statistics exceeds that of aggregate statistics. Given a drug concentration and a fixed observation time interval, it is useful in QM to count births and deaths in each identified clone during the first observation interval. The system classifies clones in which births exceeded deaths as potentially resistant, and those in which deaths exceeded births as potentially susceptible. The QM method can repeat the counting in the second time interval, while retaining the counts for prior counts in separate bins. The time of action of the AOA can be determined by the duration over which births continue to exceed deaths, relative to clones in which deaths exceed births.

Presentation of Quantum Microbiology Information

The data on individual microorganisms, clones, strains and populations that is observed and maintained as described above has, as raw data, limited usefulness to the medical personnel dependent on the data. The data must be converted into a format that is easy for the medical personnel to interpret, and which supports treatment decisions.

In general, the medical personnel do not need to have information on individual microorganisms or clones, but on aggregate data that is arranged either by strain or by population. The information, furthermore, should preferably be provided with information including:

separation of killing from stasis or lengthening of doubling time, as the killing of microorganisms has, as described above, treatment benefits.

the timing of killing, as the more rapidly that an AOA kills microorganisms, the more rapidly the patient condition will improve, the lower the likelihood of resistance arising, and the less harm that will arise from the eventual removal of AOA resistance.

doubling time information, as this can distinguish approximate stasis from infections that will appear shortly (i.e. a microorganism that does not appear on an AOA infuse agar plate might not be in stasis or dead, but rather only another few hours from appearance).

the number of resistance clones—that is, clones of resistant microorganisms will be unambiguous, and their presence will indicate the potential for infections to appear later even in the presence of AOA for which the majority of the population is susceptible.

This information is voluminous, and can be provided to the medical personnel in a variety of different formats. For example, in a format similar to that of a conventional antibiogram, columns can represent individual strains, whereas rows can represent individual parameters from above (killing, time of killing, stasis, doubling time, resistance), which can be provided either in number values (i.e. specific numbers, percentages, times), or in relative numbers (e.g. numbers of pluses or minuses).

The antibiogram is particularly useful for organizing the information by strain or organism. An alternative arrangement is the use of a predictogram. In a "predictogram," information about all of the different microorganisms and their susceptibility and specific responses to AOAs can be incorporated into an integrated format, with quantitative projections made of future growth based on measured current microorganism population numbers, kill rates from time-kill kinetics at different AOA concentrations, and growth of microorganisms from doubling time measurements at different AOA concentrations. Consider first that all of the microorganisms in a sample are of the same strain, which is characterized by a time/kill curve, a doubling time after AOA exposure, and other parameters. In this case, the predictogram would be a graph, with time in the abscissa (generally in hours, and extending for preferably at least 48 hours, and more preferably for more than 96 hours) and number of live microorganisms in the ordinate (which can be formatted with a logarithmic scale), in which the number of live microorganisms as a function of time is given. This graph is given for a constant concentration of AOA, or alternatively, a concentration of AOA that is derived from the known pharmacokinetics of the AOA, assuming that the microorganisms have been challenged in the test apparatus with concentrations to mimic the AOA concentration profile. The numbers of microorganisms over time can be estimated from time/kill curves combined with doubling times, in which the number of microorganisms at a given time can be approximated as the sum of the time/kill curve and the exponential growth curve for each individual entity in the sample, where the entity can be individual microorganisms, clones or strains. Conveniently, the system can also be modeled as a series of time steps, wherein at each time step, microorganisms are killed according to the time-kill curve, and microorganisms reproduce according to the doubling time.

The predictogram can be presented either for the population as a whole, or separate predictograms can be presented for each strain. The predictograms can include the results for a series of AOAs, or can be presented a different concentrations of the same AOA. The predictograms can be presented with multiple graphs overlaying the same axes, and conveniently would show the responses of the total or selected sub-populations with different AOAs or concentration of the same AOA so that the different treatments could be directly compared.

Alternatively, along the time axis of the predictogram, the predicted most prevalent microorganisms (for example, any microorganisms predicted to constitute at least a predetermined fraction, such as 10%, of the total population) at each time interval can be annotated.

It should be noted that the predictogram intrinsically reports the time-kill curves of each AOA. The kinetics of killing is important to the efficacy of AOAs, since the generation of resistant microorganisms proportional to the total number of microorganism divisions. If an AOA takes many cell divisions to kill a microorganism, this will increase the chances that a resistant strain will arise.

It should be noted that the results from most conventional methods do not provide good information about the doubling time for microorganisms, which does not allow predictions of microorganism growth over time to be made. Thus, the currently gold standard is the minimum inhibitory concentration, which represents a roughly arbitrary cutoff in terms of the time that the microorganism cultures are allowed to grow (e.g. if microorganisms on agar plates with AOA are allowed to grow indefinitely, bacterial growth will appear throughout the plate, both because the concentration of AOA may be spread throughout the plate and decrease in local concentration, but moreover, the microorganism doubling time is lengthened, but growth is not eliminated). Thus, providing medical doctors with information about the killing of microorganisms as a function of time, as well as growth of microorganisms as a function of time, provides new and important information in medical treatment.

As discussed above, the definition of MIC varies according to the method of susceptibility testing, but it generally refers to the minimum concentration of AOA that strongly affects the growth of the microorganism. In the present invention, the microorganisms can be challenged with a range of concentrations of AOA, and the MIC can then be determined in a number of different ways. For example, the MIC can be determined as the concentration at which the doubling time of the microorganism is increased by a predetermined factor, which factor is preferably two or more, and more preferably 4 fold or more. Alternatively, the overall growth of the microorganisms over time can be determined, and that concentration that results in no net additional growth (from a combination of killing, stasis and increase in doubling time) can be defined as the MIC. Another definition of MIC can be that concentration at which the total number of microorganisms over a predetermined period of time (which is preferably one day, and more preferably two days or more) is at some predetermined factor relative to the current number of microorganisms, wherein the predetermined factor can be either greater than, equal to, or less than one (1), and which is preferably less than 10, and more preferably one or less. It should be noted that a predetermined factor of one is equivalent to stasis.

While some measures of MIC make use of a continuous measure (e.g. the radius of the cleared zone around an disk containing a specific amount of antibiotic that is placed on an agar plate), the analyses of the present invention are generally made on the basis of discrete AOA concentrations. In order to estimate more precisely specific MICs, which might fall between the discrete concentrations tested, it is convenient to perform interpolations and extrapolations based on the discrete data obtained. The interpolations and extrapolations can be linear, quadratic or exponential, with the type of interpolation or extrapolation determined by laboratory investigations with known microorganism samples. Furthermore, it is preferable for the interpolations and extrapolations to be made independently with respect to killing and changes in doubling time, since the effects of AOAs with respect to killing and doubling time can be different, after which overall rates of microorganism growth or decay can be independently synthesized from the independent numbers.

An important secondary goal of drug selection in medical treatment is to minimize the probability of inducing or selecting resistant strains. As has been well known since the seminal paper of Luria and Delbruck in 1943 (Genetics 28:491-511), bacteria mutate at a relatively rapid rate (in the range of approximately 10.6 to $10^{-9}$ per cell division) in a selective environment. Since the total number of bacterial cell divisions in an infectious population exceeds $10^9$ by orders of magnitude, resistance can be expected to emerge spontaneously during treatment. The clinical effect may be magnified by the presence of numerous types of mobile genetic element, such as plasmids and the like, in bacterial infections, causing rapid spread of emergent or induced resistance.

Therefore rapid completion of therapy is almost as important as selecting an effective drug. The QM method can include computation of the therapeutic eradication time and therefore the optimum treatment duration. In addition, the QM method can compute the most-likely number of cell divisions throughout the course of treatment, based on sample counts, kill rates, and growth rates following onset of drug exposure. The method can then report a hierarchical listing of each drug's performance, including MIC, MBC, maximum kill rate, total treatment cell divisions, and estimated total treatment duration. This report presents a detailed, clinically relevant antibiogram for each case.

Conventional antibiograms have at least two forms. The first presents a list of MICs and/or SIR categories for a particular organism as subjected to AST. The second presents a matrix of species and drugs, with the intersection stating the percentage of isolates susceptible (or resistant) over the time period and location of the data sources (typically a year or more for a community, a whole hospital, or a hospital department).

QM methods can further provide kill kinetics (maximum kill rate) from TK curves. SIR categories have high granularity and low precision. MICs might be more precise, but are well known by those of ordinary skills in the art to embody limited predictive power. Therefore the QM method can include the production of antibiograms based on kill kinetics.

For surveillance statistics, each species/drug intersection in the QM antibiogram presents a sub-listing of strain prevalence by kill rate cluster. This offers the infection control officer a far more complete picture of trends and formulary guidance than does the conventional antibiogram.

The inherently high speed of QM analysis permits new diagnostic strategies and treatment optimization that are not possible using slower methods. Among other capabilities, QM provides factual in vivo TK curves that impute the individual's unique pharmacokinetic and pharmacodynamic variations. In addition, the in vivo TK response imputes the effects other nonquantifiable host factors such as macrophage activation and other phenomena.

This permits the QM computational methods to adjust the individual patient's in vitro model to include such effects in adjusting its projections for the total treatment regimen. Similarly, the QM database accumulates these time-based results to continually improve its statistical models.

It should also be noted that a large fraction of the microorganisms that cause human infection do not get identified by the antibodies used in clinical identification. One reason for this is that it is practically possible only to use a limited number of antibody or other identifiers, and there are a very large number of strains that cause infections. For those microorganisms that are not identified, it is convenient to provide the user with useful information that could help the medical specialists determine the likely etiological agent. This information can include image information derived from the image analysis program, including the size of the microorganism in microns, the approximate aspect ratio of the microorganism (i.e. round or elongate), the topology of growth of the microorganism (in clusters or chains, in two or three dimensions), the doubling rate of the microorganism, the susceptibility of the microorganism to each AOA, and more. Additionally, it is of particular value for the medical specialist to have images of some characteristic microorganisms. These images can either be stored as part of the normal analysis of the sample, but more preferably can be taken at a separate time, where individual microorganisms or clones representing median or modal values for the parameters above can be selected and possibly images under optimal conditions (e.g. higher magnification, or better objectives and methods that are particularly suited for visual inspection, as opposed to the mechanical analysis and staining that characterizes the overall process). These images can be presented in printed form or on a computer screen to the medical specialist, which imaging can assist him in identification of the microorganism.

It should be noted that microscopy as a measure of cell growth has a long history. Examples of the use of microscopy to demonstrate cell growth are provided by J. R. Lawrence, D. R. Korber, and D. E. Caldwell (1989) "Computer-enhanced darkfield microscopy for the quantitative analysis of bacterial growth and behavior on surfaces", J. Microbiol. Methods 10: 123-138 and A. Elfwing, Y. LeMarc, J. Baryani, and A. Ballagi (2004) "Observing Growth and Division of Large Numbers of Individual Bacteria by Image Analysis", Applied and Environmental Microbiology 70(2):675-678. It should be noted from Elfwing et al. that growth of bacteria can be measured under laminar flow whereby daughter cells are sheared away, giving a sawtooth optical profile in which the cell size increases, and then with the removal of the daughter cell, the cell size abruptly declines. In the present invention, in addition to cell size (e.g. the number of pixels), the amount of fluorescence or the amount of light scatter can also be used.

Organism viability can be determined by a variety of methods, and can include both methods that highlight viable organisms (vital stains) as well as dead organisms (mortal stains). These stains can comprise ethidium or propidium dyes, hexidium iodide, SYTO nucleic acid stains, 7-aminiactinomycin D, SYTOX Green/Orange/Blue nucleic acid stains, and others. A good introduction to these and other stains is available from the Molecular Probes Handbook, at www.probes.com, as well as "Vigor, vitality, and viability of microorganisms", David Lloyd, Anthony J. Hayes in FEMS Microbiology Letters 133 (1995).

It can be useful to detect the presence of new organisms or the increase in size of existing organisms.

It is of particular value in quantum microbiology to interrogate microorganisms repeatedly with respect to their viability or mortality. In particular, many of the stains described above persist in the cells that have been so stained, making repeated staining less accurate. A stain of particular value is resazurin, which is an intracellular redox stain, indicating the vitality of cells. A difficulty in using resazurin in certain applications is that it dissipates from cells, requiring repeated or constant exposure. To reduce this dissipation, variants of resazurin have been developed to reduce its loss from cells, and are in frequent use. However, for the application of the present invention, the dissipation of the unmodified resazurin has advantageous properties, in that it allows the repeated interrogation of cells since it does not persist. For the present invention, it is preferable to use vital and mortal stains which dissipate to the extent that they can be reapplied less than or equal to every hour, or even more preferably less than or equal to every half hour, or most preferably less than or equal to every fifteen minutes.

General Detection of Microorganisms

In some embodiments, the methods and compositions of the invention can be used for rapid detection of the quantity of microorganisms within a sample. Similar to the use of growth followed by monitoring optical density for the detection of microorganisms, the present systems can be used in a similar yet much accelerated fashion. That is, by monitoring positive growth as outlined herein, and summing the growth of individual microorganisms, a rapid determination of the amount of microorganisms can be done.

Organization of Identification and AOA Susceptibility Testing

As discussed herein, the assays of the invention are done in some instances as a "matrix", wherein a sample is divided among detection surfaces and individual experiments (e.g. different antimicrobial agents or different concentrations of antimicrobial agents or both) are run. For example, a system can have multiple "channels", each with its own input port. In such an embodiment, each channel can have more than one detection surface; for example, a test may be directed to the evaluation of five different microorganisms in a sample, each with a specific detection surface, which are then simultaneously tested for different agents and/or concentrations. Alternatively, sequential experiments can be run on the detection surface(s); for example, increasing concentrations of antimicrobial agents can be run, with optional washes in between. Similarly, different antimicrobial agents can be sequentially run.

In general, each sample will be distributed over a number of different channels so that multiple analyses can be performed. In each channel, at least two different types of analyses can be performed: quantitation and identification of the microorganisms present, and determination of the antibiotic susceptibility. For medical personnel making treatment decisions, it is best to have not only the identity of the microorganisms present, but also the AOA susceptibility of the microorganisms in terms of each type of microorganism. That is, if there are two microorganisms in a sample in roughly equal numbers, one of which is susceptible and the other of which is not, it is preferable to know which of the microorganisms is susceptible.

With this in mind, it is most preferable that in each channel, a full panel of identification be performed, and that over the channels, a full panel of anti-organism agents (AOAs) be tested, each AOA at a number of different concentrations. In this manner, each microorganism in each channel can be identified, and the AOA susceptibility determined for each microorganism. In general, because the number of potential different microorganisms is large, and because the number of AOAs and concentrations to test is also large, while the number of channels is, in general, limited.

Alternatively, having identified the microorganisms that constitute the majority of the population in a sample through methods described herein, AOAs that are specific in their action for those microorganisms can specifically be chosen for testing on that sample. This allows either a larger number of AOAs specific for those microorganisms, or alternatively, allow for more concentrations to be tested. Thus, the system controller preferably has the capability of deciding which AOAs and their concentrations to use, as opposed to having a fixed set of AOAs and concentrations.

Alternatively, testing can be organized so that in each channel, only a subset of the possible identifications is attempted, and that AOA testing in each channel is specific for those microorganisms whose identifications are attempted. For example, if there is a panel of 16 antibodies (or similar markers) for identification and there are two channels A and B, eight of the antibodies can be used in channel A and eight of the antibodies can be used in channel B. Then, in channel A, AOAs can be tested that are specific for the microorganisms that are identified via the identification antibodies used in that channel, and in channel B, AOAs can be tested that are specific for the microorganisms that are identified via the identification antibodies used in that channel. This method is particularly effective if the antibodies used for identification in each channel are chosen such that the microorganisms for which they are specific are grouped into areas of AOA susceptibility. For example, antibodies for microorganisms that are susceptible to erythromycins can be used in a single channel, while antibodies for microorganisms that are susceptible to cephalosporins can be used in a single channel, with AOA challenge by the respective AOAs in the respective channels.

Another alternative is to use a different AOA in each channel, and also to use a different set of identification antibodies in each channel. In this case, it is possible to determine what fraction of the microorganism population is susceptible to each of the AOAs, as well as to determine what fraction of the microorganism population is represented in each strain (i.e. through the antibody identification). Thus, by this information alone, it is not possible to unambiguously assign susceptibility to any one type of organism. However, assignment may be provisionally made on the basis of three additional pieces of information. Firstly, the numerical similarities of identification and susceptibility can be highly indicative. For example, if 30% of the microorganism population is strain A and 70% of the microorganism population is strain B, and 30% of the microorganism population is susceptible to AOA X and 70% of the microorganism population is not susceptible to AOA X, then it can be provisionally inferred that strain A is susceptible to AOA X and strain B is not susceptible. Furthermore, as discussed above, certain strains are either never or usually susceptible to a particular AOA, so that in the previous example, if strain B is known rarely or never to be susceptible to AOA X, this would provide confirmatory information of the prior assignment of susceptibility.

A third piece of information that can be marshaled in this assignment of susceptibility to particular strains is the use of physical information that is observed and stored about individual microorganisms, as is described elsewhere in this specification. Thus, if strain A is a 1 micron spherical microorganism that grows in "strings", and strain B is a rod shaped microorganism of dimensions 1 micron by 3 microns, and grows in clusters, then if the susceptible strain is seen to be a 1 micron spherical microorganism, the assignment of the susceptible microorganism as strain A gains additional support.

Another method of using a minimal number of channels for performing both identification and AOA susceptibility testing is to use multiple passes over a period of time. A portion of the sample is placed into channels where identification is done on with groups of antibodies, and the sample is also challenged with multiple AOAs. For example, in channel A, the microorganisms are identified with combined antibodies A, B, C and D and in channel B, the microorganisms are identified with combined antibodies E, F, G, and H, and in channel C, the microorganisms are identified with combined antibodies 1, J, K, and L, wherein a positive identification indicates only that the positive microorganisms are one of the four strains for which the antibodies were specific. Also, the microorganisms in channel A are challenged with AOAs P and Q, in channel B are challenged with AOAs R and S, and in channel C are challenged with AOAs X and Y. Depending on the results of this first pass, in a subsequent second pass, other parts of the sample can then be identified with only those antibodies that were part of the positive result in the first pass, and challenged only with those AOA to which susceptibility was seen. Thus, in the example above, if positive identification of microorganisms was only seen in channel A, and AOA susceptibility was seen only in channel B, then in a subsequent pass on other parts of the sample, identification can be performed only with antibodies A, B, C and D, and AOAs R and S tested. In this example, depending on the distribution of identifications and susceptibilities, three channels in the first pass and channels in the second pass would give complete information about identifications and susceptibilities that could 12 or more channels in a single pass.

It should be understood that this method can be used solely with respect to identification or solely with respect to susceptibility, whereas the other test can be performed in a single pass. Furthermore, in performing multiple passes, microorganisms from the sample can be simultaneously introduced to all of the channels, for which identification and susceptibility testing is initially attempted in only a subset of channels. Microorganisms in the other channels are allowed to grow in broth during the first pass, so that at the beginning of the second pass, the microorganisms are in "log phase" growth, and the larger number of microorganisms provides better information for the second pass.

The number of passes used in the analysis can be more than two, where information from initial passes is used in subsequent passes, and multiple passes can be used in alternative manners. For example, in a first pass, maximum doses of AOAs can be used, in order to indicate overall susceptibility of the microorganisms in the sample to the specific AOAs. In a second pass, using preferably microorganisms that having been growing during the first pass, for those AOAs shown to be effective, titrations with different concentrations of the AOA can be used in order to establish MICs, MBCs and other more detailed information about the interaction of the AOA with the microorganisms in the sample.

Screening for Bioactive Agents Including Antimicrobial Agents

In addition, the present invention also provides methods and compositions for screening for bioactive agents that can be used as antimicrobial agents. In some cases this involves testing candidate agents for bioactivity against a microorganism, e.g. in drug development, as the methods of the invention allow rapid throughput. Additionally, the methods and compositions of the invention can be used to screen microorganisms for susceptibility to agents; for example, as microorganisms become resistant to some antimicrobial agents, they can be tested for susceptibility to other known but currently unused antimicrobial agents.

Thus, the present invention provides methods of screening candidate agents for bioactivity. By "candidate agent" as used herein describes any molecule, e.g., protein, nucleic acid, small organic molecule, polysaccharide, etc. that can be screened for activity as outlined herein. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, as is more fully outlined below, the candidate agents are either randomized proteins (including biased proteins or proteins with fusion partners) or expression products of cDNA libraries or libraries derived from cDNA libraries, such as fragmented (including randomly fragmented cDNA libraries). These are added to the cells as nucleic acids encoding these proteins. As will be appreciated by those in the art, these cDNA libraries may be full length or fragments, and can be in-frame, out-of-frame or read from the anti-sense strand.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eucaryotic genomes or cDNA libraries may be used as is outlined above for proteins.

In a preferred embodiment, the candidate bioactive agents are organic chemical moieties, a wide variety of which are available in the literature.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$ Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In general, the screening for active agents proceeds as outlined herein for general testing, with the modulation of growth (again including positive, neutral and negative growth) serving as an indicator of bioactivity.

Biosensor Components

The present invention provides devices for the detection of target microorganisms that general include a biosensor cartridge and a detection system.

Biosensor Cartridges

The biosensor cartridges of the invention can take on a variety of formats. In general, the cartridge consists of a first "top" substrate and a second "bottom" substrate, separated by a spacer to allow the formation of chambers or modules between the surfaces. Ports for fluid introduction or removal, electronic interconnects, etc., can all be part of the cartridge as well.

Substrates

The biosensor cartridges of the invention comprise at least one a solid substrate. The solid substrate can be made of a wide variety of materials and can be configured in a large number of ways, as is discussed herein and will be apparent to one of skill in the art. In addition, a single device may be comprises of more than one substrate; for example, there may be a "sample treatment" cassette that interfaces with a separate "detection" cassette; a raw sample is added to the sample treatment cassette and is manipulated to prepare the sample for detection, which is removed from the sample treatment cassette and added to the detection cassette. There may be an additional functional cassette into which the device fits; for example, a heating element which is placed in contact with the sample cassette to effect reactions such as growth of the microorganisms. In some cases, a portion of the substrate may be removable; for example, the sample cassette may have a detachable detection cassette, such that the entire sample cassette is not contacted with the detection apparatus.

The composition of the solid substrate will depend on a variety of factors, including the techniques used to create the device, the use of the device, the composition of the sample, the analyte to be detected, the size of the wells and microchannels, the presence or absence of electronic components, etc. Generally, the microbe-contacting devices of the invention should be easily sterilizable and disposable as well.

In a preferred embodiment, the solid substrate can be made from a wide variety of materials, including, but not limited to, silicon such as silicon wafers, silicon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdenum, tantalum, KOVAR, KEVLAR, KAPTON, MYLAR, brass, sapphire, etc. High quality glasses such as high melting borosilicate or fused silicas may be preferred for their UV transmission properties when any of the sample manipulation steps require light based technologies. In addition, as outlined herein, portions of the internal surfaces of the device may be coated with a variety of coatings as needed, to reduce non-specific binding, to allow the attachment of binding ligands, for biocompatibility, for flow resistance, etc. For example, as outlined in the Examples, the use of resistant coatings such as OPTICHEM can be used.

In a preferred embodiment, the solid substrate is configured for handling a single sample that may contain a plurality of target microorganisms. That is, a single sample is added to the device and the sample may either be aliquoted for parallel processing for detection of the microorganisms (see FIG. 1) or the sample may be processed serially, with individual targets being detected in a serial fashion. In addition, samples may be removed periodically or from different locations for in line sampling.

In a preferred embodiment, the solid substrate is configured for handling multiple samples, each of which may contain one or more target microorganisms. See for example FIG. 1. In general, in this embodiment, each sample is handled individually; that is, the manipulations and analyses are done in parallel, with preferably no contact or contamination between them. Alternatively, there may be some steps in common; for example, it may be desirable to process different samples separately but detect all of the target analytes on a single detection surface.

In addition, it should be understood that while most of the discussion herein is directed to the use of planar substrates with microchannels and wells, other geometries can be used as well. For example, two or more planar substrates can be stacked to produce a three dimensional device, that can contain microchannels flowing within one plane or between planes; similarly, wells may span two or more substrates to allow for larger sample volumes. Thus for example, both sides of a substrate can be etched to contain microchannels; see for example U.S. Pat. Nos. 5,603,351 and 5,681,484, both of which are hereby incorporated by reference.

Electrodes

By "electrode" herein is meant a composition, which, when connected to an electronic device, is able to sense a current or charge and convert it to a signal. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide (ITO), palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). ITO electrodes are particularly useful in applications utilizing optical detection, as ITO electrodes can be optically transparent.

The electrodes described herein are depicted as a flat surface, which is only one of the possible conformations of the electrode and is for schematic purposes only. The conformation of the electrode will vary with the methods used. For example, flat planar electrodes may be preferred for optical detection methods or ease of synthesis.

Microchannels

In some embodiments, the devices of the invention include at least one microchannel or flow channel that is used either to allow the flow of sample within the cartridge between cartridge components, or that serves to house the detection surface(s) of the invention. For example, in the former, microchannels can be used for flowing sample from the sample inlet port to the other components or modules of the system. As will be appreciated by those in the art, the flow channels may be configured in a wide variety of ways, depending on the use of the channel. For example, a single flow channel starting at the sample inlet port may be separated into a variety of smaller channels, such that the original sample is divided into discrete subsamples for parallel processing or analysis.

Alternatively, several flow channels from different modules, for example the sample inlet port and a reagent storage module may feed together into a mixing chamber or a reaction chamber. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer and sometimes tortuous flow channels can be used.

Figure 4A:
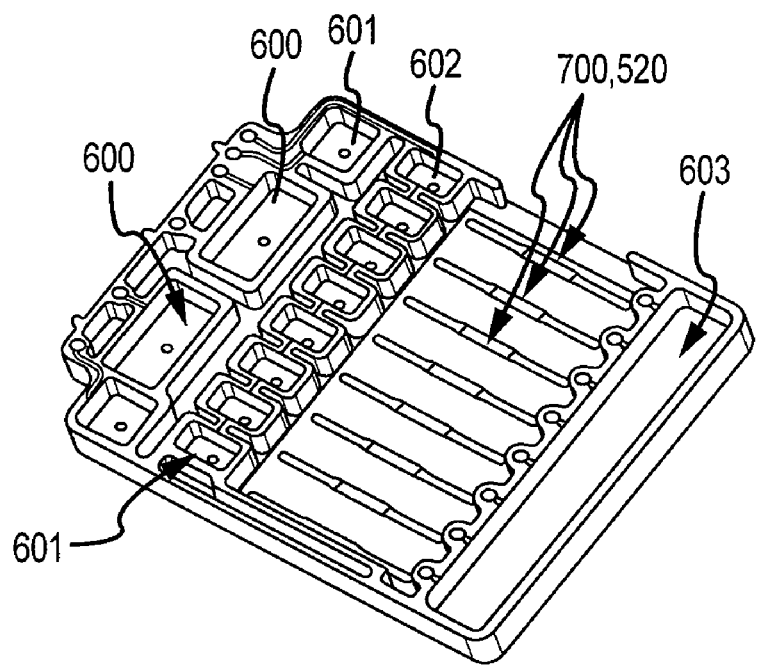
FIGS. 4A and 4B depict several schematics of different potential configurations of biosensor cartridges.
Figure 4B:
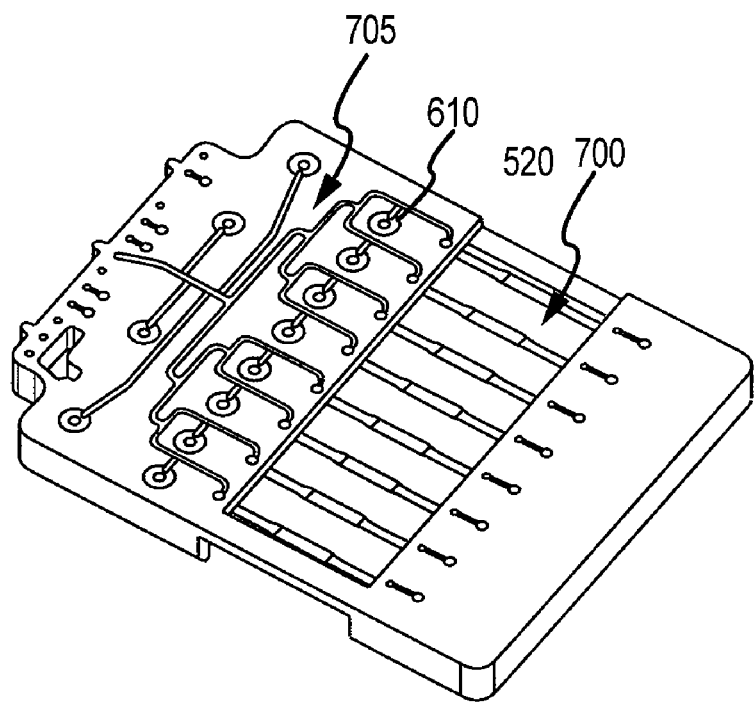

In an additional embodiment, the cartridge comprises one or more microchannels that house detection surfaces. For example, FIG. 1 depicts a cartridge with a plurality of microchannels, each with a plurality of detection surfaces. FIG. 4 depicts a cartridge with a plurality of microchannels, each with a single detection surface.

Modules

In addition to the flow channel system, the devices of the invention may be configured to include one or more of a variety of components, herein referred to as "modules", that will be present on any given device depending on its use. These modules include, but are not limited to: sample inlet ports; sample introduction or collection modules; cell handling modules (for example, cell removal, cell concentration, cell separation or capture, cell growth, etc.); separation modules, for example, for electrophoresis, dielectrophoresis, gel filtration, ion exchange/affinity chromatography (capture and release) etc.; reaction modules for chemical or biological alteration of the sample; chemical, physical or enzymatic cleavage or alteration of moieties on the surface of the microorganisms, or chemical modification of these moieties; fluid pumps; fluid valves; thermal modules for heating and cooling; storage modules for assay reagents; mixing chambers; and detection modules.

In a preferred embodiment, the devices of the invention include at least one sample inlet port for the introduction of the sample to the device. This may be part of or separate from a sample introduction or collection module; that is, the sample may be directly fed in from the sample inlet port to a separation chamber, or it may be pretreated in a sample collection well or chamber.

In a preferred embodiment, the devices of the invention include a sample collection module, which can be used to concentrate or enrich the sample if required; for example, see U.S. Pat. No. 5,770,029, including the discussion of enrichment channels and enrichment means.

In a preferred embodiment, the cell handling module includes a cell separation or capture module. This embodiment utilizes a cell capture region comprising binding sites capable of reversibly binding a cell surface molecule to enable the selective isolation (or removal) of a particular type of cell from the sample population, for example, white blood cells for the analysis of chromosomal nucleic acid, or subsets of white blood cells. These binding moieties may be immobilized either on the surface of the module or on a particle trapped within the module (i.e. a bead) by physical absorption or by covalent attachment. Suitable binding moieties will depend on the cell type to be isolated or removed, and generally includes antibodies and other binding ligands, such as ligands for cell surface receptors, etc. Thus, a particular cell type may be removed from a sample prior to further handling, or the assay is designed to specifically bind the desired cell type, wash away the non-desirable cell types, followed by either release of the bound cells by the addition of reagents or solvents, physical removal (i.e. higher flow rates or pressures), or even in situ lysis.

Alternatively, a cellular "sieve" can be used to separate cells on the basis of size. This can be done in a variety of ways, including protrusions from the surface that allow size exclusion, a series of narrowing channels, a weir, or a diafiltration type setup.

In a preferred embodiment, the cell handling module includes a cell removal module. This may be used when the sample contains cells that are not required in the assay or are undesirable. Generally, cell removal will be done on the basis of size exclusion as for "sieving", above, with channels exiting the cell handling module that are too small for the cells.

In a preferred embodiment, the cell handling module includes a cell concentration module as outlined herein.

In a preferred embodiment, the devices of the invention include a reaction module. This can include either physical, chemical or biological alteration of one or more sample components.

Pumps

In a preferred embodiment, the devices of the invention include at least one fluid pump. Pumps generally fall into two categories: "on chip" and "off chip"; that is, the pumps (generally electrode based pumps) can be contained within the device itself, or they can be contained on an apparatus into which the device fits, such that alignment occurs of the required flow channels to allow pumping of fluids.

In a preferred embodiment, the pumps are contained on the device itself. In one aspect, the pumps are electrode based pumps; that is, the application of electric fields can be used to move both charged particles and bulk solvent, depending on the composition of the sample and of the device Suitable on chip pumps include, but are not limited to, electroosmotic (EO) pumps and electrohydrodynamic (EHD) pumps; these electrode based pumps have sometimes been referred to in the art as "electrokinetic (EK) pumps". All of these pumps rely on configurations of electrodes placed along a flow channel to result in the pumping of the fluids comprising the sample components. As is described in the art, the configurations for each of these electrode based pumps are slightly different; for example, the effectiveness of an EHD pump depends on the spacing between the two electrodes, with the closer together they are, the smaller the voltage required to be applied to effect fluid flow. Alternatively, for EO pumps, the spacing between the electrodes should be larger, with up to one-half the length of the channel in which fluids are being moved, since the electrode are only involved in applying force, and not, as in EHD, in creating charges on which the force will act.

In a preferred embodiment, an electroosmotic pump is used. Electroosmosis (EO) is based on the fact that the surface of many solids, including quartz, glass and others, become variously charged, negatively or positively, in the presence of ionic materials. The charged surfaces will attract oppositely charged counterions in aqueous solutions. Applying a voltage results in a migration of the counterions to the oppositely charged electrode, and moves the bulk of the fluid as well. The volume flow rate is proportional to the current, and the volume flow generated in the fluid is also proportional to the applied voltage. Electroosmostic flow is useful for liquids having some conductivity is and generally not applicable for non-polar solvents. EO pumps are described in U.S. Pat. No. 4,908,112, U.S. Pat. No. 5,632,876, PCT US95/14586 and W097/43629, incorporated by reference.

In a preferred embodiment, an electrohydrodynamic (EHD) pump is used. In EHD, electrodes in contact with the fluid transfer charge when a voltage is applied. This charge transfer occurs either by transfer or removal of an electron to or from the fluid, such that liquid flow occurs in the direction from the charging electrode to the oppositely charged electrode. EHD pumps can be used to pump resistive fluids such as non-polar solvents. EHD pumps are described in U.S. Pat. No. 5,632,876, hereby incorporated by reference.

In a preferred embodiment, a micromechanical pump is used, either on- or off-chip, as is known in the art.

In a preferred embodiment, an "off-chip" pump is used. For example, the devices of the invention may fit into an apparatus or appliance that has a nesting site for holding the device, that can register the ports (i.e. sample inlet ports, fluid inlet ports, and waste outlet ports) and electrode leads. The apparatus can include pumps that can apply the sample to the device. Such pumps are well known in the art.

In a preferred embodiment, the devices of the invention include at least one fluid valve that can control the flow of fluid into or out of a module of the device, or divert the flow into one or more channels. A variety of valves are known in the art. For example, in one embodiment, the valve may comprise a capillary barrier, as generally described in PCT US97/07880, incorporated by reference. In this embodiment, the channel opens into a larger space designed to favor the formation of an energy minimizing liquid surface such as a meniscus at the opening. Preferably, capillary barriers include a dam that raises the vertical height of the channel immediately before the opening into a larger space such a chamber. In addition, as described in U.S. Pat. No. 5,858,195, incorporated herein by reference, a type of "virtual valve" can be used.

In a preferred embodiment, the devices of the invention include sealing ports, to allow the introduction of fluids, including samples, into any of the modules of the invention, with subsequent closure of the port to avoid the loss of the sample.

In a preferred embodiment, the devices of the invention include at least one storage module for assay reagents. These are connected to other modules of the system using flow channels and may comprise wells or chambers, or extended flow channels. They may contain any number of reagents, buffers, enzymes, redox mediators, antimicrobial agents, salts, etc., including dried reagents that may be reconstituted using inline flow, storage, dilution, and selective dispensing.

In one aspect, a plurality of storage modules are used on a cartridge that store a plurality of different antimicrobial agents and other reagents as needed, including dyes (e.g. mortal stains, specific binding ligands, etc.).

In a preferred embodiment, the devices of the invention include a mixing module; again, as for storage modules, these may be extended flow channels (particularly useful for timed mixing), wells or chambers. Particularly in the case of extended flow channels, there may be protrusions on the side of the channel to cause mixing.

In a preferred embodiment, the devices of the invention include a detection module. As outlined herein, there are several basic ways the assays of the invention may be run, generally including the presence or absences of labels.

Manufacture of Biosensors

The devices of the invention can be made in a variety of ways, as will be appreciated by those in the art. See for example W096139260, directed to the formation of fluid-tight electrical conduits; U.S. Pat. No. 5,747,169, directed to sealing; EP 0637996 131; EP 0637998 1311; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071,531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876-15,593,838; 5,585,069; 5,637,469; 5,486,335; 5,755,942; 5,681,484; and 5,603,351, all of which are hereby incorporated by reference. Suitable fabrication techniques again will depend on the choice of substrate, but preferred methods include, but are not limited to, a variety of micro-machining and microfabrication techniques, including film deposition processes such as spin coating, chemical vapor deposition, laser fabrication, photolithographic and other etching techniques using either wet chemical processes or plasma processes, embossing, injection molding and bonding techniques (see U.S. Pat. No. 5,747,169, hereby incorporated by reference).

Detection Systems

A number of methods of realtime detection are convenient within the spirit of the present invention, including confocal microscopy in conjunction with scattering, fluorescence, upconverting phosphors, quantum dots or other indicators, as well surface plasmon resonance (SPR). Confocal microscopy takes advantage of a very shallow depth of field, such that objects away from the surface are out of focus and the light energy is either dispersed or reduced through spatial filtering. Imaging similar to confocal imaging is also possible using very large numerical aperture objectives which also have shallow depth of field. Surface plasmon resonance uses an arrangement of components similar to that of detection using single bounce non-waveguide architectures, as described above, in which the top surface of the glass is coated with a reflective, metallic surface which is conveniently gold. In this case, the amount of light reflected by the gold is affected by the presence of material bound to the microorganisms bound to the detection surface. Surface plasmon resonance is well suited to the present invention, in that the gold surface can serve both as a reflective surface, as well as the electrode for use in reaction acceleration and binding force discrimination.

The methods above have the advantage that microorganisms binding to the detection surface are visible and distinguishable even in the presence of unbound microorganism, since only that target that is bound is visible. However, it is further within the spirit of the present invention for alternative arrangements of illuminators and detectors, given that unbound microorganisms can be removed from the region of detection, either by removal of the solution in which the microorganisms are provided (e.g. as shown below in the case of chambers for the detection of bacteria), or through the sequestration of the microorganisms in another region. The latter method can involve, for example, the electrophoresis of microorganism to another electrode that is not in the optical path either of the detector and/or illuminator.

Some of the arrangements that are available within the present invention can be understood with reference to two parallel substrates (a lower and an upper substrate) with electrodes on these substrates facing each other across an internal gap. We can then define from bottom to top four different surfaces—the lower bottom surface, the upper bottom, surface (i.e. with an electrode on which probe is deposited), the lower top surface (i.e. with an electrode without probe) and an upper top surface. The detector in-general will be either below the lower bottom surface or above the upper top surface (i.e. it is not in the gap between the two substrates).

If the detector is below the lower bottom surface, then the electrode on the upper bottom surface will generally be transparent, except in the case of surface plasmon resonance. In the case of surface plasmon resonance, the detector must also be below the lower bottom surface. The illumination can either be also below the lower bottom surface, passing through the bottom substrate electrode, with back-scattered light, evanescent light (which reflect off of the upper bottom surface), or light that is meant to excite fluorophores, upconverting phosphors or quantum dots. Alternatively, the illumination can be from within the bottom substrate, as described above. Also, the illumination can be from within the gap between the two substrates, which would generally be best for a light scattering application. Alternatively, the illumination can be from above the upper top surface, transiting through the top substrate, through the gap, and then to the upper bottom surface where it interacts with the target or a tagged target. In those cases, once again, the detector can detect either scattered light (e.g. forward scattered light), or fluorphores, upconverting phosphors, or quantum dots, or the samples can be viewed for brightfield, darkfield, phase or other forms of microscopic imaging (generally using light from a condenser).

If the detector is above the upper top surface, receiving light from the tagged target, in this case the electrode on the upper bottom surface need not be transparent, while the electrode on the lower top surface should be transparent. If the upper bottom surface is opaque, then the illumination must either come from above that electrode surface, or be generated at the tagged target, as might occur with chemiluminescence. With an opaque upper bottom surface, the illumination can be within the cap (most likely for scattered light analysis), and otherwise most likely for scattered light or excitation illumination for fluorphores, upconverting phosphors, or quantum dots. If the electrode on the upper bottom surface is transparent, however, light can be transmitted from below, including by evanescent wave illumination as described above.

While the detector is generally an imager (e.g. a CCD or CMOS camera), it can also comprise a laser scanner with a PMT or other light gathering device. In certain cases, the detector can also entail a general light gathering device (PMT, photodiode, photoresistor) with diffuse illumination. The latter case will be primarily used in those cases where averaged signal over an area provides suitable signal, as discussed below.

When using a CCD or CMOS camera, the information is obtained pixel by pixel, generally in 8-12 bit grayscale, though in certain cases (e.g. with indicators color-coded for different targets) a color image can alternatively be used. In those cases where it is useful or important to register individual target binding events, there are potentially two modes of operation. In a first mode, target binding is limited so that only a fraction of the pixels register with a signal—most pixels are at some background level, so that the change from the background level to a level significantly above background level at a pixel denotes a binding event. Depending on the size of the target (and/or its tag), a single binding event may correspond to an increase in the signal above background at a number of different contiguous pixels (most image processing software has routines that can group together regions of contiguous pixels into discrete "events"). In this case, the dynamic range of the system ranges from less than 100 targets and as small as 1 target (and is limited by the statistical variation of the small number of targets), to as roughly as high as the number of pixels in the camera divided by the average number of pixels per target (with a floor of one), and then divided by a factor approximating 10, which is the "saturation point" at which new targets would more likely overlap with existing targets rather than being deposited on areas with approximately background levels of signal. For a camera with 5 megapixels, and a target that spans approximately 2 pixels, this corresponds to a dynamic range that spans roughly from 10 to 250,000 targets, or a dynamic range of 25,000. This range is adequate for many applications, and in those applications for which a greater dynamic range is required, multiple dilutions can be used.

In a second mode, the differences between a single target and different numbers of targets within a pixel can be discriminated. For example, if the signal is measured with an 8-bit pixel, with 256 levels, and a background signal is 12, then a single binding event might average 62, two targets in the same pixel might average 112, and so on. In this case, the dynamic range is far higher, and is roughly the number of pixels times the number of levels that can be discriminated divided by the average number of pixels per target (with a floor of one) and further divided by a factor of approximately 10, representing the saturation at which additional target binding could raise levels in a significant number of pixels above the pixel saturation level. In this case, with 5 levels being able to be discriminated and an average number of pixels per target being 1, the dynamic range is still roughly a minimum of 10 (limited by solely statistical considerations), but the upper level now extends to approximately 2.5 million, or an additional ten fold dynamic range from the previous example. The difficulty encountered with this second mode of operation is that it becomes increasingly difficult to distinguish specific from non-specific binding on the basis of image analysis—both because on average each target spans a smaller number of pixels, and because the contrast between different levels is generally poor.

While these methods can distinguish individual binding events, it should be noted that the greatest value of counting individual binding events occurs when there is significant non-specific binding or other forms of noise. For example, low level background noise can sum over a large area to comprise a large noise signal, for which a large amount of specific signal is required to show above background. However, in cases where the signals are generally large above background, it can be convenient to use a signal summing method, wherein the signal is summed either by adding the signal values at each pixel, or by using an analog summing technique such as the use of a photodiode or a photoresistor or a photomultiplier tube (PMT).

It should be noted that while ITO or other transparent electrode material is preferable for real-time monitoring via visible indicators, this does not mean that both the cathode and the anode need to be comprised of ITO. In other instances, it can be preferable for one of the electrodes to be transparent, allowing observation into the reaction cell, while the other electrode to be a relatively non-reactive, opaque electrode, such as gold or a refractory metal, such as platinum, palladium, or iridium which are stable in electrophoresis. In these cases, the resistance in the metallic electrode will be very small, which can reduce the inhomogeneity effects above, and furthermore, the potential on the metallic electrode may not have the same deleterious effect as on the ITO electrode (e.g. with a Pt electrode), allowing higher potential to be used in the cell. Alternatively, both electrodes can be opaque, with one electrode being coated with gold. In this case, the detection can be made optically via surface plasmon resonance.

There are a number of other components comprising compete systems according to the present invention, including power controllers for establishing the potential differences between electrodes that will be cause and control the electrophoretic force on the microorganisms, illuminators, detectors, and storage controllers (e.g. controllers and hard disk drives) that store the information from the detectors and then present it to the user or compare information from multiple sources or times. Some of these components are well-known in the art, such as electrophoresis power supplies (which can be computer controlled and which can be set to provide either constant voltage or constant current, and which can be supplemented with digital or analog electronic circuitry to provide low to high frequency waveforms as described elsewhere in this specification and which can also be used for dielectrophoresis), illuminators (e.g. lasers, arc lamps, incandescent lamps, microscope light condensers, and which can involve methods of coupling the light into light waveguides), indicators (as described above and below), detectors (cameras, lenses, filter sets, image analysis software), and the like, even as their arrangement and use is novel and to novel effect in the present invention. Where the components differ from prior art, they will be discussed both above and below.

The automated detector may comprise an optical detector. The optical detector may utilize optical detection methods including light scattering imaging, brightfield imaging, darkfield imaging, surface plasmon resonance, phase imaging, fluorescence imaging, upconverting phosphor imaging, quantum dot imaging, and chemiluminescence imaging.

In one aspect, evanescent illumination techniques are used for detection; see U.S. Ser. No. 10/888,828, incorporated by reference herein.

The following examples serve to more fully describe the manner of using the above described invention, as well as to set forth the best modes contemplated for carrying out various aspects of the invention.

EXAMPLES

Example 1

Electrokinetic Concentration

A flow cell was constructed by sandwiching two ITO modified glass microscope slides between a plastic laminate structure forming a 4 channel flow cell as illustrated in FIG. 50. The distance between the slide surfaces is approximately 500 microns. The bottom ITO slide was precoated with amine reactive OptiChem (Accelr8) and chemically modified with diethylene triamine (DETA) to yield a cationic bacteria capture surface.

A mixture of $1\times10^7$ CFU/ml of Staphylococcus aureus in 10 mM hydroquinone, 10 mM DTT, and 10 mM CAPS pH 6.5 was injected into a flow chamber. A potential difference (1.6 V) was applied across the ITO slides for approximately 3 minutes to surface concentrate and bind the bacteria to the DETA OptiChem modified ITO electrode. Photomicrographs of the surface of the anode before the application of the potential and 50 seconds later show the presence of the electrokinetically concentrated S. aureus microorganisms. The number of bacteria within a predetermined area was plotted as a function of time after application of the potential, and within 30 seconds, the number of bacteria had saturated, and from other measurements was known to include nearly all of the bacteria in the original sample (data not shown).

Example 2

Microorganism Growth

The redox solution from Example 1 was replaced with tryptic soy growth media and incubated at 37 C on an inverted microscope to establish detectable growth of bacteria bound to DETA surface. Photomicrographs of the S. aureus at the beginning of growth and after different incubation times were taken (data not shown). The photomicrographs were taken with phase optics, and the flare surrounding the bacteria indicated the presence of additional bacteria resulting from cell division of the original bacteria. Thus bacterial growth ca follow electrokinetic concentration.

Example 3

AOA Susceptibility

Bacteria concentrated and grown as in Examples 1 and 2 were challenged by 5 micrograms/ml of oxacillin to which the S. aureus strain used was susceptible. Simultaneous with the administration of oxacillin was the administration of 10 micromolar propidium iodide, which is excluded from live cells, and thus whose presence in fluorescence images is indicative of cell death. Photomicrographs of the bacteria at the beginning of AOA treatment were taken, under phase contrast and fluorescence microscopy, and additional images were taken one hour later (data not shown). There was a large increase in fluorescence which indicated the large amount of cell death from the administration of oxacillin.

Example 4

Modeling of AOA Susceptibility

The effect of oxacillin on S aureus can be modeled using a mathematical Hill function:

$$\text{Effect} = \frac{E_{max} \times t^n}{ET_{50} + t^n}$$

Where Emax is equivalent to the maximum effect over time t, ETW is the time at which half the maximal effect is achieved and n is the shape factor for the effect. The number of bacteria at time t is equivalent to the effect subtracted from the initial population of bacteria (N°).

$$N = N_o - \frac{E_{max} \times t^n}{ET_{50} + t^n}$$

The shape effect n, Emax and ET50 can adequately model growth or death of bacteria as a function of time.

The NCCLS broth microdilution MIC determination involves the exposure of a standardized inoculum (approximately $1\times10^5$ CFU/ml) to a concentration of antibiotic for a defined period of time (24 hrs) under rigorously controlled environment (cation adjusted Muellerhinton broth at 37° C.). The MIC is defined as the minimum concentration at which organism growth is impeded below the threshold limit of detection by unaided eye ($1\times10^7$ CFU/ml). Correlation of kinetic measurements of growth rates and viability with standardized NCCLS MIC and MBC methods can therefore be estimated using mathematical models of bacteria growth and/or death.

The NCCLS defines oxacillin resistant *S. aureus* break point as detectable growth in a broth microdilution assay at or above 0.12-0.5 ug/ml. It is preferable to minimize the antibiotic concentrations analyzed so single concentrations of antibiotics at or above breakpoints can be used to perform kinetic diagnostic susceptibility testing.

The mathematical modeling of the antibiotic effects on bacteria growth can be very useful in correlating kinetic diagnostic curves with established breakpoints used to classify bacteria as susceptible, intermediate, or resistant. For example, the kinetic generation of bacteria and drug interactions can be fitted in real time. Once fitting parameters are satisfied the data can be extrapolated to estimate the final bacteria concentration at 24 hours. Endpoint windows can be defined to correlate effectiveness of antibiotic with gold standard methods. Bacteria samples with concentrations significantly lower than $1\times10^6$ CFU/ml were called susceptible, in the range of $1\times10^6$-$1\times10^7$ CFU/ml were called intermediate, and significantly greater than $1\times10^7$ were called resistant.

Bacteria growth curves show "S" shaped curve consisting of an initial lag phase, followed by an exponential growth phase, and then a stationary phase is achieved when growth is resource limited. Bacteria growth in liquid broth cultures (NCCLS broth microdilution methods) slows to stationary phase at approximately $1\times10^8$ to $1\times10^9$ CFU/ml. Therefore, the Emax for bacteria in liquid cultures is about $1\times10^9$ defined for modeling purposes where n and $ET_{50}$ define the rate at which bacteria grow. n and $ET_{50}$ are determined from kinetic diagnostic data and fitting rules can be developed. For example, the maximum rate of change of bug growth cannot exceed the growth rate constant defined for exponential phase bacteria (unexposed bacteria) as described by the traditional exponential equation:

$$N = N_o e^{kt}$$

where N=concentration of bacteria at time t, and No is the initial bacteria concentration. Bacteria exposed to antibiotics likely change growth rates in which constant ken is relevant. Since both models describe bacteria growth as a function of time they can are equivalent (after lag time and before the onset of stationary phase). Rearrangement yields keg in terms of n, EC50, Emax, and t:

$$k_{\textit{eff}} = \frac{ln\left[\frac{N_o - \frac{E_{max} \times t^n}{ET_{50} + t^n}}{N_o}\right]}{t}$$

Therefore at time t and previously defined Emax, the n and EC50 cannot yield a Keg.>K0. Furthermore the Emax model can easily be converted into a growth rate that has an intuitive physical correlation to doubling time of bacteria. Positive Keg correlates with bacteria growth and negative Ken correlates with bacteria death. Parameter fitting can be complete upon determination of maximal effect of antibiotic, or recording kinetics up to inflection point of the response curve, or minimally gathering sufficient data enabling statistical confidence in defining shape factor and EC50 of curve prior to an inflection point.

Graphs of models of the growth of different *S. aureus* strains were made after the administration of 5 micrograms/ml of oxicillin. Growth constants during exponential growth phase are approximately 2.3 correlating to about one doubling every 20 minutes in the case of oxicillin resistant bacteria. Curves show the effects of oxicillin on an *S. aureus* stain of intermediate resistance (data not shown); growth after 24 hrs is on the order of $1\times10^7$ CFU/ml, and significantly lower than that of the resistant bacteria. Growth with a strain of *S. aureus* that is susceptible to oxicillin shows a negative $K_{\textit{eff}}$ growth constant indicating death of bacteria as a function of time.

Once the bacteria and antibiotics are described mathematically, the models can be used to estimate results obtained by gold standard AST methods. Dramatic effects on bacteria growth rates (no growth observed over 16 hrs) and viability results shows good fit between actual data and models for the effects of 5 micrograms/ml of oxicillin on the growth of susceptible *S. aureus*, using data measured from methods previously discussed, with the use of propidium iodide staining above a threshold used to determine cell viability. Such modeling enables the determination of bacteria susceptibility as defined by predefined breakpoints since:

$K_{\textit{eff}}$ is less than zero since bacteria are dying with respect to time.

Inflection point encountered at hour 1 determining a negative slope to the maximum rate of change of bacteria with respect to time indicating high rate of bacteria death.

Effect essentially complete at end of hour 2 reducing the overall population of bacteria. No observable growth present in sample.

Given that our concentration was above the NCCLS defined break point for oxacillin and *S. aureus* we use kinetic diagnostics to identify a susceptible *S. aureus* sample after a 1-2 hour oxacillin incubation. The modeling also can provide means for better describing antibiotic effects enabling quantitative comparisons of antibiotics characterized as susceptible by NCCLS standards but with different kill rates. Antibiotics with the fastest and most effective kill rate can be determined and reported for clinical relevance.

*S. aureus* and oxacillin reach steady state wherein two classes of bacteria were identified within the test sample. One class of *S. aureus* stained with propidium iodide indicating loss of viability while another class did not stain but did not double over course of antibiotic exposure. Post antibiotic exposure studies conducted using *S. aureus* and oxacillin indicated that none of the *S. aureus* organisms doubled after 3-5 hours of incubation indicating a state of dormancy or cryptobiosis incapable of generating significant rates of growth. This class of organisms should be considered dead for the purposes of correlating bacteria kinetics to NCCLS susceptibility.

The shape of bacteria antibiotic kinetics and depend heavily on mechanism of action of antibiotics on organism. Gentamicin, a protein synthesis inhibitor, and its kinetic effects on susceptible *E. coli* was tested. The ken is negative, inflection point occurred around hour 2 with the Em . . . , and was complete after approximately 4 hours of exposure. Kinetic differences are evident in comparison to *S. aureus* and oxicillin effects.

Example 5

Demonstration of Device and Method for Rapid Concentration and Detection of Microorganisms at a Detection Surface In this example we demonstrate a device and rapid method for concentrating microorganisms at a detection surface using electrokinetic concentration (EKC).

Microfluidic Flow Cell. The flow cell device described in this Example provides microfluidic, electrochemical, and optical functionality. The device consists of a gasket defining a flow cell with channel dimensions 30×2.5×0.5 mm (L×W×H) (Grace BioLabs, Inc.). The gasket is sandwiched between two indium tin oxide (ITO) coated glass slides (Delta Technologies). In order to provide fluid access to the flow cell, holes were drilled through the top ITO electrode at locations that provide access to a gasket chamber when the device is assembled. The back or outside of these holes are fitted with NanoPort™ adhesive fittings (Upchurch Scientific), which allow plastic tubing connection to the flow cell. Fluid pumping through the tubing is via a syringe pump (Kloehn, Inc.). A valving system attached to the Kloehn pump allows reagent solutions from different reservoirs to be pumped into the flow cell. An additional syringe access port is available on the tubing inlet to the flow cell, which allows low volume reagents, materials, or bacterial samples to be introduced to the flow cell. Because the ITO glass slides are transparent, there is optical access to the entire flow cell. For electrochemical applications, the top and bottom ITO electrodes were attached to a power supply through wire clips attached directly to the slide.

In addition to the gasket based flow cell described in the previous paragraph, the assays in this Example have also been performed in laminated plastic cartridges equipped with ITO glass slide electrodes, such as that shown in FIGS. 4D and 4E.

The flow cell is maintained at approximately 35° C. by resistively heating the top ITO slide. A power supply is attached through clips on opposite ends of the slide. Current flows through the ITO surface causing heating. In order to monitor temperature, a thermocouple is inserted in a temperature sensing fluid well on the slide.

Affinity Surface Preparation. Prior to assembling the cell, the bottom or capture electrode was coated with an affinity component to which microorganism irreversibly bind. The affinity component in this experiment was a two-part coating comprising bovine serum albumin (BSA) and the polycationic polymer poly-L-lysine (PLL). The affinity component coating was prepared as follows. First, the ITO-glass slides were carefully cleaned using a 15-minute hot (60° C.) detergent (Alconox) sonication followed by a 15-minute hot water sonication. After removal from the second sonicator, the slide was extensively washed with ultrapure water and spun dry in a centrifuge (Beckman) equipped with a swing-arm slide carrier. Once dry, the clean slides were coated with PLL using well-established literature protocols. Briefly, the slides were submerged in a solution containing approximately 0.01% PLL in 0.1× phosphate buffered saline (PBS). The slides were incubated in the PLL solution at room temperature for one hour, were then rinsed with ultrapure water and then centrifuged dry. The dry PLL slides were then heat sealed with a desiccant pouch in a foil barrier bag and were allowed to age for four days at room temperature.

After four days aging, the slides were removed from the packaged and were submerged in a solution containing 5% (w/v) BSA (Sigma) in PBS. The BSA incubation proceeded at room temperature for one hour, at which point the slides were rinsed with PBS containing 0.01% Tween20 (PBST) and then with ultrapure water. Slides were then centrifuged dry and were ready to use.

While it is desirable to strongly attach microorganisms to the bottom electrode, it is generally desirable to keep microorganisms off of all other surfaces in the microfluidic device. This is particularly try of the top ITO slide, which in addition to serving as the top electrode also defines the top part of the flow. For this reason the top ITO electrode was coated with a low non-specific binding polymer surface called OptiChem® (U.S. Pat. No. 6,844,028).

Electrokinetic Concentration (EKC). EKC was performed in an identical manner for each microorganism. The steps were as follows. Stock bacterial tryptic soy broth solutions were centrifuged to pellet organisms. The pellet was resuspended in 1 mM histidine as a wash step and then re-pelleted. This pellet was then resuspended in electrokinetic concentration (EKC) buffer. The EKC buffer was an aqueous solution containing 1 mM histidine, 10 mM hydroquinone, and 40 mM DTT at pH 6.8. Resuspension was to an estimated organism concentration of 1E+07 CFU/ml. The baceteria/EKC buffer suspension was then pumped into the microfluidic flow cell. One microscope field of view in the flow cell, 0.593× 0.444 mm, was monitored throughout the entire experiment. The pump was stopped once the flow cell was full. At that point, the power to the ITO electrodes was turned on, and electrokinetic concentration proceeded for 5 minutes at 1.6 V. At the end of 5 minutes, essentially all organisms migrated to the affinity surface (BSA-PLL) where they bound to the surface, and the power to the electrodes was turned off.

Following EKC, the flow cell was washed by pumping approximately 1 ml histidine buffer through the system. This removed any loosely bound organisms, and more importantly flushed out the EKC buffer. The histidine wash was then followed by a tryptic soy broth growth medium flush.

Imaging. Detection in this example is by darkfield microscopy performed on a customized Olympus IX71 inverted microscope equipped with a 20× LCPlan Fluor objective with a 0.40 NA. The microscope is equipped with an Optronics MicroFire CCD camera and image acquisition software.

Model Bacterial Strains. The primary bacterial strain used in this and several following examples is *Klebsiella pnuemoniae* (ATCC 700603). Additional bacterial strains investigated include: *Staphylococcus aureus* (ATCC 29213), *Escherichia coli* (ATCC 25922), *Escherichia coli* O157:H7, *Pseudomonas aeruginosa* (ATCC 49189), *Stenotrophomonas maltophilia* (ATCC 13637), *Kiebsiella pnuemoniae* (ATCC 49472), *Acinetobacter* (ATCC 49139), *Streptococcus pneumoniae* (ATCC 49136), and *Haemophilus influenzae* (ATCC 10211). These bacteria constitute an important panel of pathogenic microorganisms with particular relevance to hospital-acquired pneumonia.

Figure 5A:
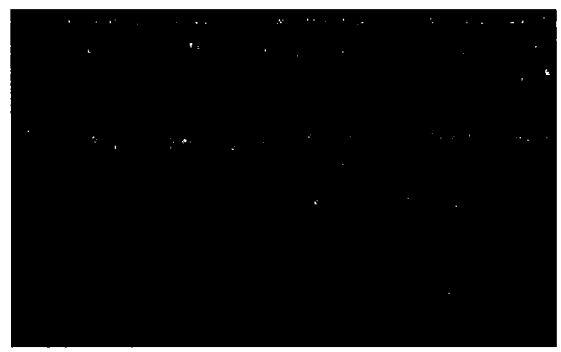
FIGS. 5A-5D depict some results from Example 4.
Figure 5B:
Figure 5C:
Figure 5D:

Representative Time-Lapse Images. Representative darkfield microscopy images of *K. pneumoniae* (ATCC 700603) during electrokinetic concentration are provided in FIG. 5. FIG. 5(a) shows the detection surface at the time of sample introduction into the EKC cell. This image shows that initially, very few organisms are located at the surface. FIG. 5b provides an image of the detection surface after 1 minute of EKC. A large number of microorganisms can be seen in the detection surface plane. Bacteria approaching the detection surface appear as out of focus blobs. FIG. 5(c) shows the detection surface after 2 minutes of EKC. Here an even larger number of bacteria are in the detection plane. Finally, FIG. 5(d) shows the detection surface after 3 minutes of EKC, at which point concentration is complete essentially no more bacteria enter the field of view. This sequence of photos demonstrates the rapid concentration of the bacterial sample at the detection surface.

Figure 6:
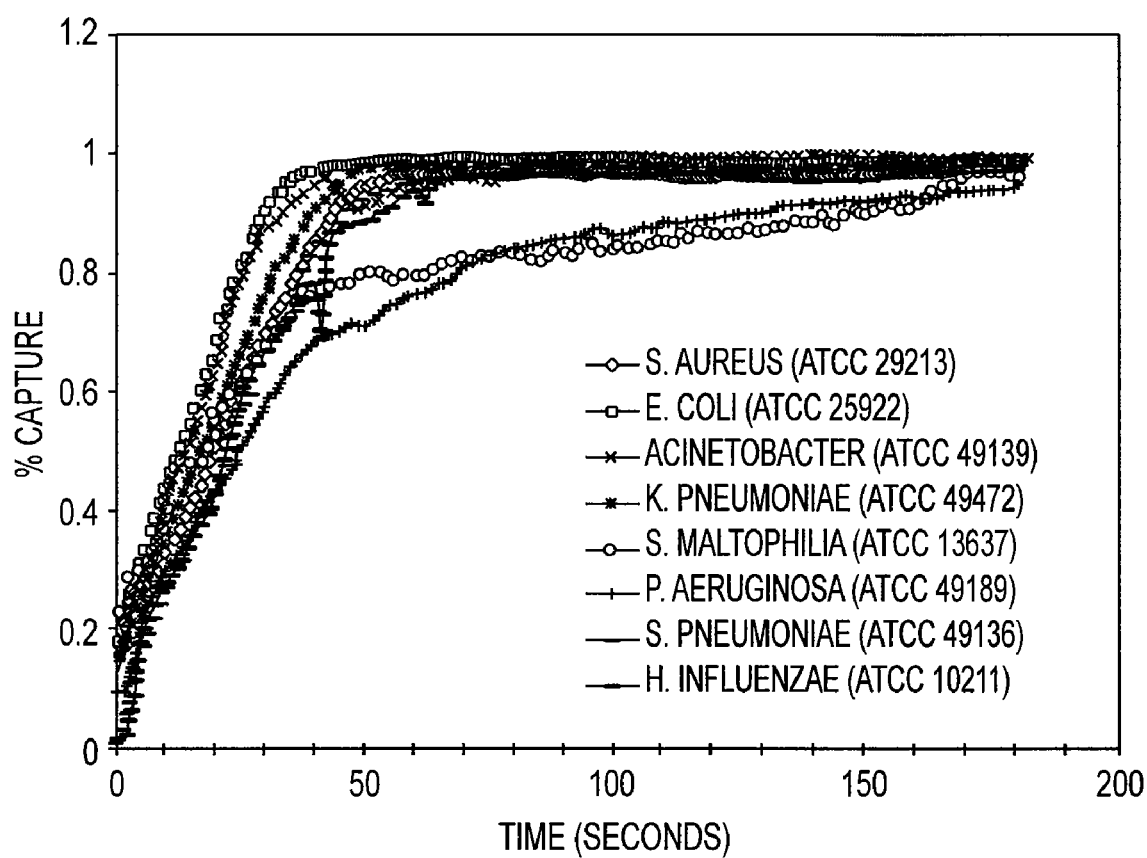
FIG. 6 depicts some results from Example 4.

EKC Results for a Panel of Microorganisms. A variety of pathogenic bacteria have been tested in order to demonstrate the broad compatibility of the EKC approach with clinically relevant microorganisms. FIG. 6 shows electrokinetic concentration profiles in the form of number of captured bacteria as a function of time. Results clearly demonstrate that all of the microorganisms on this clinically relevant pneumonia panel can be rapidly concentrated to a detection surface.

Example 6

Demonstration of Device and Method for Rapid Identification and Mapping Of Microorganisms at a Detection Surface Using Immunochemistry In this example we demonstrate a device and rapid method for identifying microorganism species using immunochemistry. The starting point for this Example is the detection surface after electrokinetic concentration of K. pneumoniae (ATCC 700603) as described in Example 4. Here we demonstrate immuno-identification of this of this known control species.

Immunoassay. The immunoassay in this Example is a two-step identification method. The primary antibody was a mouse anti-Klebsiella IgG (abCAM, #ab8065-1). The secondary, or detection antibody was goat anti-mouse IgG labeled with the fluorescent dye Alexa 546 (Molecular Probes). Primary and secondary antibodies were suspended in tryptic soy broth (TSB) at an antibody concentration of approximately 5 ug/ml immediately prior to use. The primary antibody was introduced to the microfluidic flow cell through the inlet port. After the primary antibody solution filled the flow cell, the flow was stopped and the antibody was allowed to incubate for 15 minutes. The cell was then rinsed with 2.5 ml of TSB and then the secondary was introduced and incubated for 15 minutes. After the secondary antibody incubation, the flow cell was finally rinsed with TSB and microorganisms at the detection surface were imaged.

Imaging. For each field of view in the assay, two images are taken using the Olympus IX-71 described in Example 4. A darkfield image (as described above) is first taken to observe the location of all objects at the detection surface. Without repositioning the field of view, the microscope is then switched to epi-fluorescence mode, which for Alexa546 requires the green Olympus filter cube. By registering the darkfield with the fluorescence image, those organisms that stain with a given antibody are designate as a known species.

Figure 7A:
FIGS. 7A and 7B depict some results from Example 5.
Figure 7B:
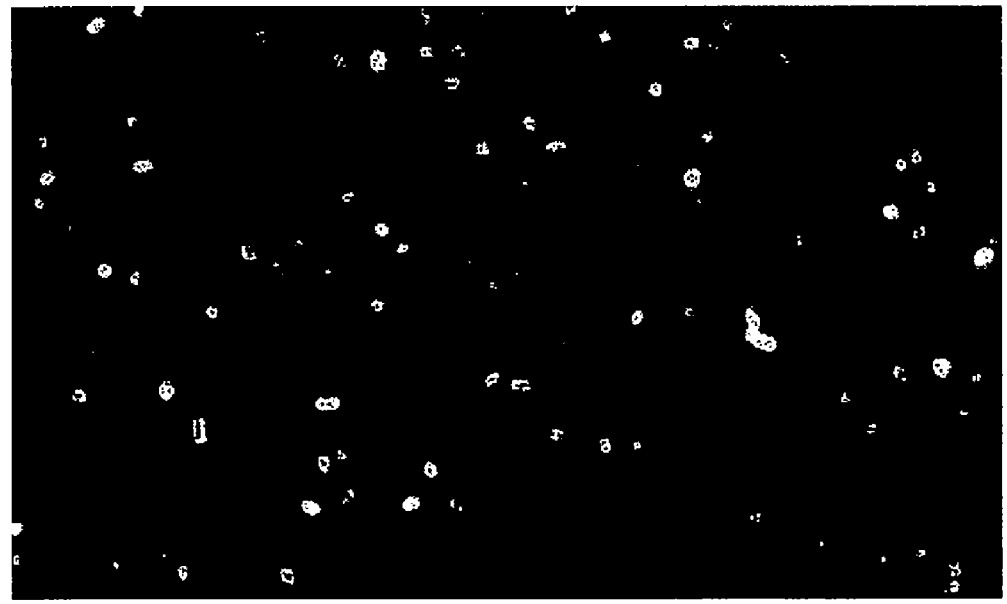

Results. Representative immunoassay images are provided in FIG. 7. FIG. 7(a) provides darkfield image of the detection surface immediately after EKC (see Example 4. FIG. 7(b) shows the same field of view in the fluorescence channel. Here we note that essentially all of the microorganisms are labeled with the antibodies, as was expected in this control experiment. Note that some of the microorganisms appear significantly brighter with the antibody stains than do others. Note also that the fluorescence image gives more diffuse blobs than does the darkfield image.

Example 7

Demonstration of Device and Method for Rapid Identification of Microorganisms in a Model Bronchoalveolar Lavage (BAL) Specimen using Immunochemistry This example demonstrates the selectivity of antibodies for their cognate target in the model K. pneumoniae system described in Example 5. In this Example, instead of introducing a neat suspension of K. pneumoniae into the flow cell, the bacteria were first spiked into a sheep bronchoalveolar lavage (BAL) sample. The sheep BAL was performed on healthy sheep at the Colorado State University College of Veterinary Medicine. Sterile normal saline was used as the lavage fluid. The K. pneumoniae was spiked to a concentration of $10^7$ CFU/ml.

This sample was introduced to the flow cell and the immunoassay was performed in the same manner as described in Example 5. In this Example, phase contrast microscopy was used instead of darkfield. Antibody detection was with epi-fluoroescence microscopy as described above.

Figure 8A:
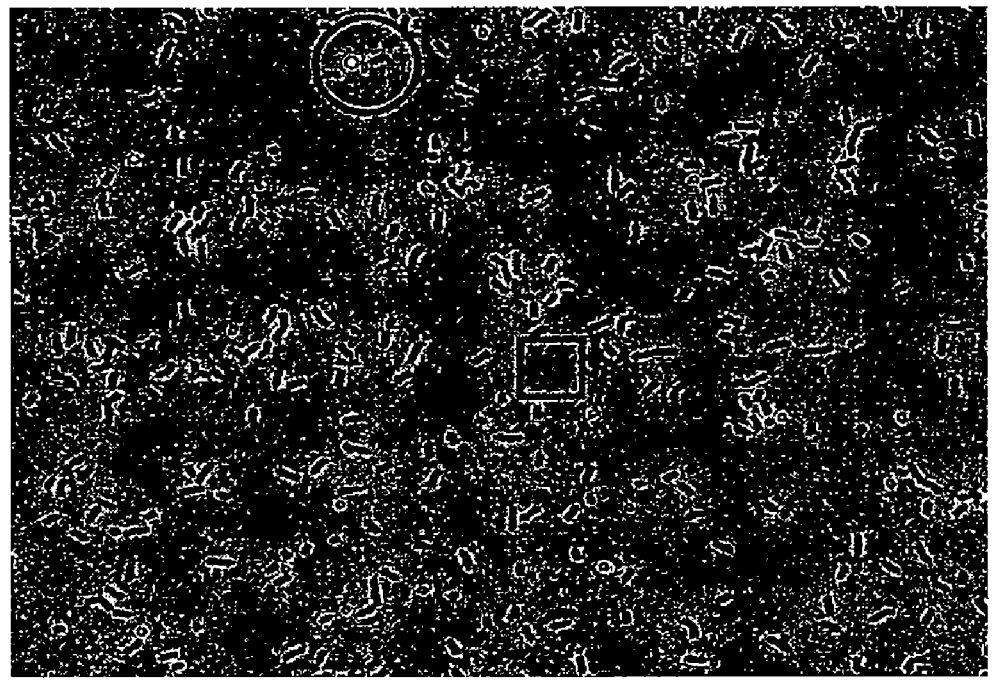
FIGS. 8A and 8B depict some results from Example 6.
Figure 8B:

Results are presented in FIG. 8. Boxes have been drawn on the two images to highlight sheep BAL components that were not stained, demonstrating the selectivity of the antibodies for their cognate microorganism.

Example 8

Demonstration of Device and Method for Simultaneous, Temporal Tracking of Individual Microorganism Growth in a Collection of Large Numbers of Microorganisms In this example we demonstrate a device and method for simultaneously tracking the growth of a large number individual microorganisms in time. The starting point for this example is the detection surface after electrokinetic concentration and immunoassay of K. pneumoniae (ATCC 700603) as described in Examples 4 and 5.

Growth. Captured organisms were incubated in TSB under static conditions. The flow cell volume is large relative to the number of microorganisms on the detection surface, so nutrient and waste flux is not considered to be an issue during this short time growth assay.

Figure 9A:
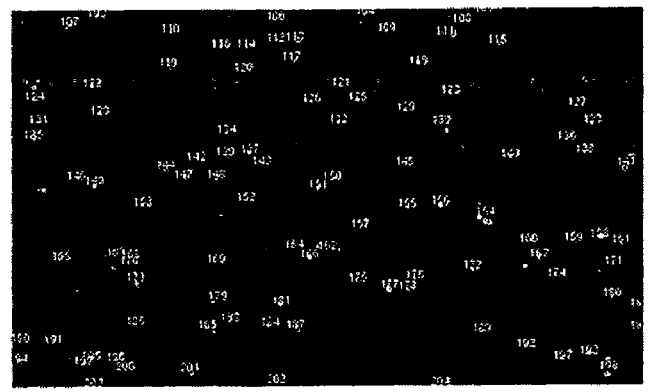
FIGS. 9A, 9B, 9C and 9D depict some results from Example 7.
Figure 9B:

Individual Microorganism/Clone Tracking. Within a given field of view, the location of all captured microorganisms can be determined using image analysis tools. These locations are stored in software. Since the immunoassay has been completed, the location and species identity of the founder organisms in the field of view is known and can be monitored in time. FIG. 9(a) shows the detection surface field of view with each founder microorganism or clone assigned a unique identifier. FIG. 9(b) shows the same field of view without the identifiers. This is designated as the time=0 point for growth, although it should be noted that there has previously been 30 minutes of incubation in the TSB during the immunoassay step. The inset shows four individual microorganisms or clones, which were assigned identifiers 158, 161, 171, 180 in the top image. The microorganism in the top left of the inset image (#158), is likely a rod shaped bacteria oriented perpendicular to the capture plane.

Figure 9C:
Figure 9D:

FIG. 9(c) shows the same field of view after 20 minutes of growth. Individual microorganisms/clones have increased in size. FIG. 9(d) shows the same field of view after 45 minutes of growth. At this point many of the individuals have doubled in apparent sized.

This set of images demonstrates our ability to track growing individuals in time.

FIG. 10 provides a plot of growth curves of all individual clones in the field of view at the detection surface. The point of including this figure is to illustrate that we can track and obtain quantitative growth information for every individual clone within the field of view. The metric used to track growth in this example is integrated intensity, which is based on blob analysis of the darkfield images and is a mathematical function of the two-dimensional projected area and pixel intensity of a given clone. The superposition of all growth curves show that a large fraction of the clones have very similar, near logarithmic growth. A subset are slow growers and an additional subset show no growth at all.

Example 9

Demonstration of Device and Method for Monitoring the Antibiotic Susceptibility of Individual Microorganisms in a Collection of Large Numbers of Microorganisms This Example is a continuation of Example 7, in which we demonstrate the ability to monitor antibiotic susceptibility of individual microorganisms in a collection of a large number of microorganisms. The starting point for the Example is the field of view in the device detection surface after 45 minutes of growth as described in Examples 4-7.

Antibiotic Introduction and Mortal Staining. The antibiotic Ciprofloxacin was suspended at a concentration of 100 ug/ml in tryptic soy. The solution also contained the fluorescence mortal stain YO-PRO-1 (Molecular Probes) at a concentration of 1 uM. YO-PRO-1 is mortal stain, and does not penetrate live cells. When a dead or dying cell loses membrane integrity, the YO-PRO-1 dye enters the cell and interacts with nucleic acids.

This Ciprofloxacin/YO-PRO/tryptic soy solution was pumped into the flow cell and then flow was shut off. The microorganisms at the detection surface were then allowed to incubate under static conditions at 35° C. A pair of images was collected every 10 minutes—first a darkfield image as described above, then a epi-fluorescence image to detect YO-PRO.

Figure 11A:
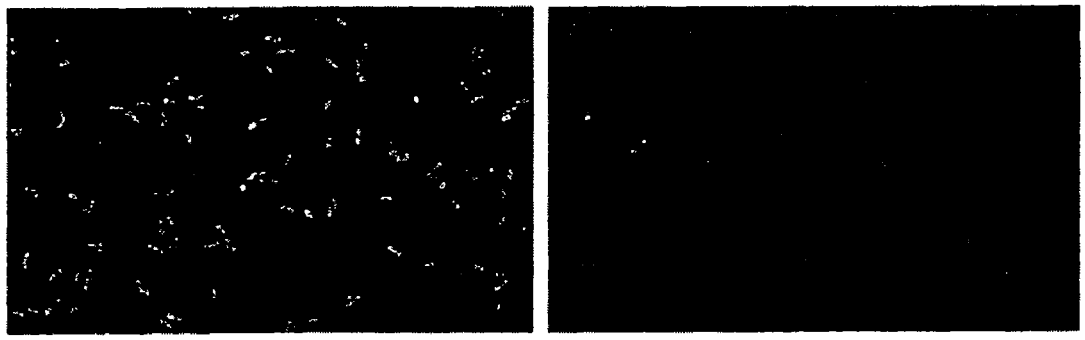
FIGS. 11A, 11B and 11C depict some results from Example 8.
Figure 11B:
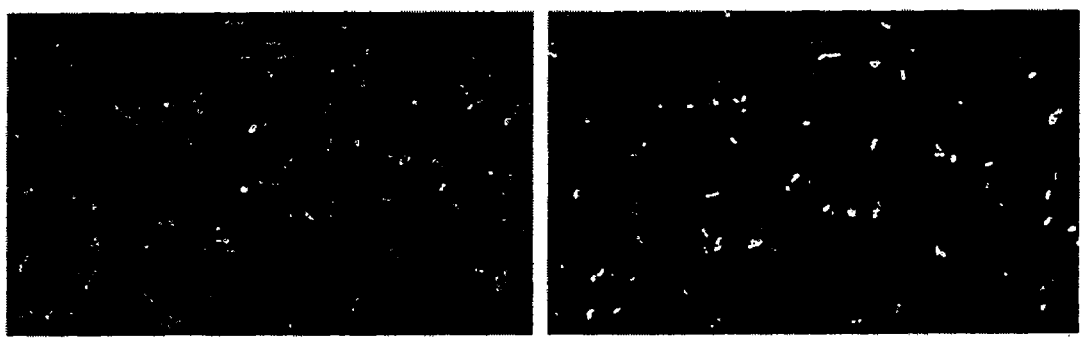
Figure 11C:
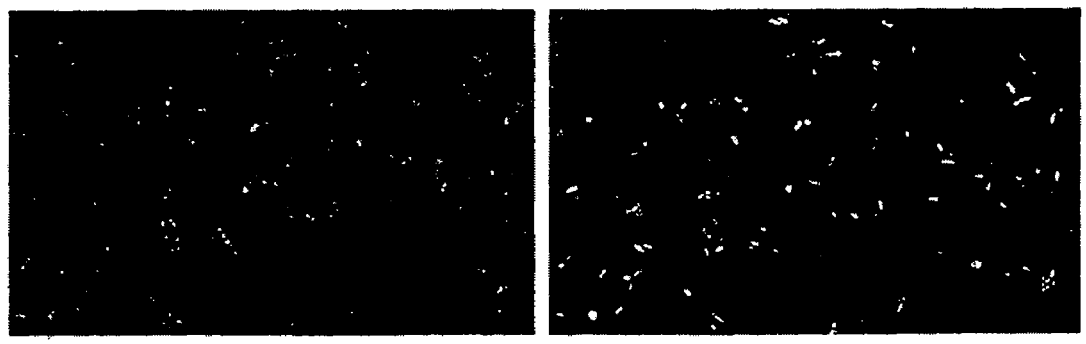

Results. Representative time-lapse images are provided in FIG. 11. A pair of images are presented for each time point. The darkfield image of all microorganisms at the detection surface is shown at the left. The YO-PRO fluorescence image of the same field of view is shown on the right. FIG. 11(a) shows the pair of images at the time of antibiotic introduction. Only a very small number of microorganisms show any signal in the YO-PRO channel, indicating that nearly all are viable at the time of antibiotic introduction. FIG. 11(b) provides the image pair after 80 minutes of antibiotic exposure. While the darkfield image is largely unchanged, relative to the initial time point, large numbers of microorganisms are clearly staining with the YO-PRO, indicating effective kill with the antibiotic. FIG. 11(c) provides the image pair after 170 minutes of antibiotic exposure. Again, large numbers of individual microorganisms are staining as dead. Because all microorganisms/clones are tracked individually, each has a time point at which is declared dead by mortal stain.

Figure 12:
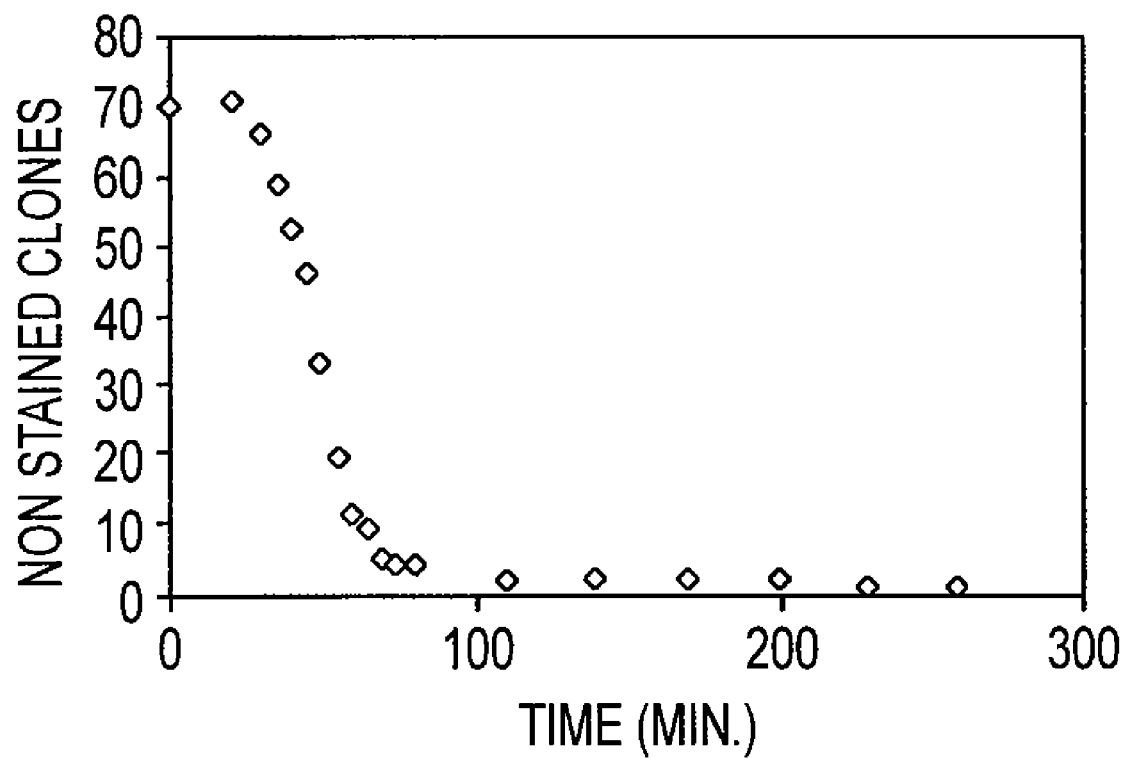
FIG. 12 depicts some results from Example 8.

FIG. 12 provides a quantitative assessment of the antibiotic kill rate (time-kill curve) by reporting the number of non-stained (i.e. live) clones as a function of time. Here we see the Ciprofloxacin at 100 ug/ml has effectively killed essentially all K. pnuemoniae clones within 90 minutes of exposure.

Example 10

Demonstration of Device and Method for Detecting Minority Resistant Microorganisms in a Collection of Large Numbers of Microorganisms Exposed to Antibiotics In this example we demonstrate a device and method for detecting minority resistant organisms in a collection of large numbers of microorganisms exposed to antibiotics. The instrument described in Example 4 is used here, but phase contrast microscopy is used instead of darkfield.

Minority Resistance Model System Description. Two bacterial species were used for this Example. The first is E. coli (ATCC 25922), which is known to be susceptible to β-lactam antibiotics. The second is K. pneumoniae ESBL bla$_{SHV-18}$ (ATCC 700603), which is known to be resistant to β-lactam antibiotics. In order to simulate a specimen containing minority resistant organisms, E. coli and K. pneumoniae were mixed at a 100:1 ratio. Thus, 1% of the clones in the starting specimen were known resistant organisms.

Figure 13A:
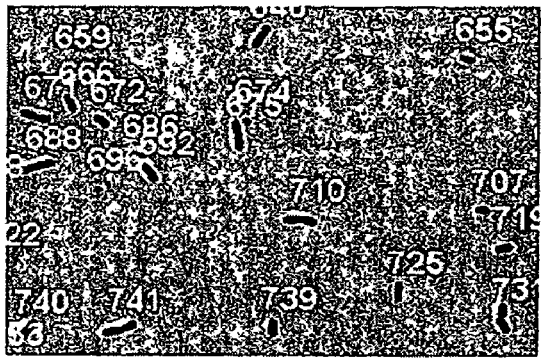
FIGS. 13A, 13B, 13C, 13D, 13E and 13F depict some results from Example 9.
Figure 13B:

Assay. The mixed species specimen was introduced into the flow cell and was driven to the detector surface as described in Example 5. FIG. 13(a) shows a small area of a field of view at the detector surface after EKC. Note that both species are gram negative rods and it is impossible to determine species based on morphology. Immunoassay, however, can be used for species identification. In this experiment, we used the antibody system described in detail in Example 5. FIG. 13(b) shows an image of the K. pnuemoniae immunoassay fluorescence channel. The image clearly shows that one of the microorganisms/clones in the field of view, designated as #675, stained positively as K. pnuemoniae. None of the other clones in the image gave antibody signal so all of those organisms are assumed to be E. coli ATCC 25922 by default.

Figure 13C:
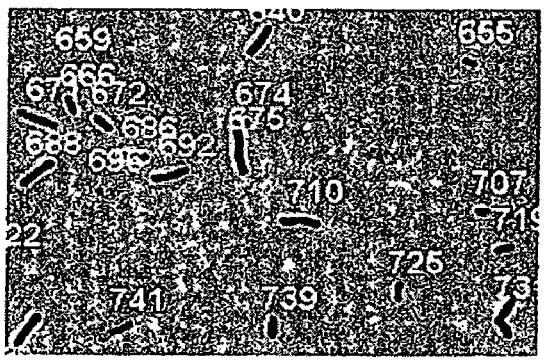
Figure 13D:
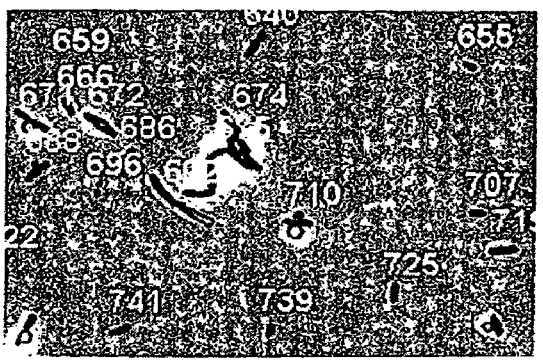
Figure 13E:
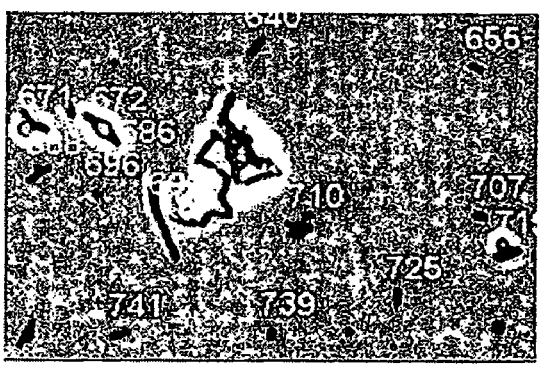
Figure 13F:
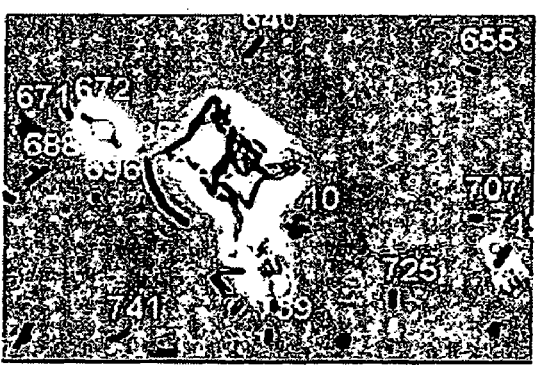

The β-lactam antibiotic Ampicillin was suspended in tryptic soy broth at a concentration of 40 ug/ml and was delivered to the flow cell. The clones then underwent static incubation in this presence of this antibiotic. A sequence of time lapse images were collected every 15 minutes, a representative set of which is shown in FIG. 13(c-f). FIG. 13(c) shows the clones after 30 minutes of antibiotic exposure. The majority of clones show little or no growth in this time frame, and in fact a large fraction stain as dead with YO-PRO-1 (data not shown, see method of Example 8). K. pneumoniae clone #675, the known resistor, has nearly doubled in length during this first 30 minutes of antibiotic exposure. FIG. 13(d) shows the clones after 60 minutes of antibiotic exposure. Here a majority of the E. coli clones are losing their physical integrity as the antibiotic takes effect. K. pneumoniae clone #675, however, continues to grow, and in the image has gone through at least one full doubling. FIGS. 13(e) and (f) provide images at 90 and 120 minutes of antibiotic exposure. At these time points nearly of E. coli are dead (confirmed with YO-PRO). But it is readily apparent that the K. pneumoniae ESBL bla$_{SHV-18}$ is indeed showing resistance in this assay as the original founder organism has now become a multicellular clone.

This clear demonstration of the identification and detection of a minority resistant strain is an important demonstration of the disclosed technology. A known weakness of traditional bacterial culture and isolation methods is that they miss minority resistant microorganisms. In this case, a 1:100 minority organism would not be selected for isolation and would be missed in diagnosis. If, however, this were a patient sample and the positive E. coli culture results were used to direct therapy with Ampicillin as the antibiotic, this example clearly shows that the pathogenic strain of K. pneumoniae would not be affected by the selected therapy and the infection would continue. The device and rapid method described for detecting and identifying minority resistant organisms in a large collection of microorganisms has important implications for clinical diagnosis and improving patient outcomes.

Example 11

Demonstration of Device and Method for Rapid Detection of Erythromycin-Induced Clindamycin Resistance in a MLS$_B$i Staphylococcus aureus Strain In this example we demonstrate a rapid, less than 4 hour in vitro diagnostic assay to correctly identify the resistance phenotypes of three model S. aureus strains. The assay has been performed on two different microfluidic/electrokinetic flow cell configurations, both of which include optically transparent electrodes. Detection in this example is by phase contrast microscopy, although fluorescence and darkfield have also been demonstrated. Imaging is performed on a customized Olympus IX71 inverted microscope equipped with a 20× objective and a Optronics MicroFire CCD camera.

Affinity Surface Preparation. Prior to assembling the cell, the bottom or capture electrode was coated with an affinity component to which microorganism irreversibly bind. The affinity component in this experiment was a two-part coating comprising bovine serum albumin (BSA) and the polycationic polymer poly-L-lysine (PLL). The affinity component coating was prepared as follows. First, the ITO-glass slides were carefully cleaned using a 15-minute hot (60° C.) detergent (Alconox) sonication followed by a 15-minute hot water sonication. After removal from the second sonicator, the slide was extensively washed with ultrapure water and spun dry in a centrifuge (Beckman) equipped with a swing-arm slide carrier. Once dry, the clean slides were coated with PLL using well-established literature protocols. Briefly, the slides were submerged in a solution containing approximately 0.01% PLL in 0.1× phosphate buffered saline (PBS). The slides were incubated in the PLL solution at room temperature for one hour, were then rinsed with ultraclean water and then centrifuged dry. The dry PLL slides were then heat sealed with a desiccant pouch in a foil barrier bag and were allowed to age for four days at room temperature.

After four days aging, the slides were removed from the packaged and were submerged in a solutions containing 5% (w/v) BSA (Sigma) in PBS. The BSA incubation proceeded at room temperature for one hour, at which point the slides were rinsed with PBS containing 0.01% Tween20 (PBST) and then with ultrapure water. Slides were then centrifuged dry and were ready to use.

While it is desirable to strongly attach microorganisms to the bottom electrode, it is generally desirable to keep microorganisms off of all other surfaces in the microfluidic device. This is particularly try of the top ITO slide, which in addition to serving as the top electrode also defines the top part of the flow. For this reason the top ITO electrode was coated with a low non-specific binding polymer surface called OptiChem® (U.S. Pat. No. 6,844,028).

Microfluidic Cassette. Two different microfluidic/electrokinetic flow cell configurations have been used to successfully perform the described assay. The first is a simple device in which a rubber gasket with channel dimensions 30×2.5×0.5 mm (L×W×H) (Grace BioLabs, Inc.) is sandwiched between two indium tin oxide (ITO) coated glass slides (Delta Technologies). In order to provide fluid access to the flow cell, holes were drilled through the top ITO electrode at locations that provide access to a gasket chamber when the device is assembled. The back or outside of these holes was fitted with NanoPort™ adhesive fittings (Upchurch Scientific), which allow plastic tubing connection to the flow cell. Fluid pumping through the tubing was via a syringe pump (Kloehn, Inc.). When the two slides were sandwiched around the gasket, a flow cell was defined, one that has optical access through the transparent electrodes and fluidic access through the NanoPort™ fittings. The flow cell was also an electrochemical cell, as the parallel top and bottom ITO electrodes were attached to a power supply through wire clips attached directly to the slide.

The second configuration comprised a simple laminated plastic microfluidic cassette. The cassette features a single flow cell chamber (20×4×0.7 mm) with inlet and outlet ports and valves integrated into the plastic cassette. Fluid access is through a manifold at the end of the cassette that interfaces to the microfluidic pump station (Micronics MicroFlow). The plastic laminate cassette uses the same top and bottom ITO-glass slides as described above. They are attached to the cassette through a pressure-sensitive adhesive layer that provides a no-leak seal.

The flow cell was maintained at approximately 37° C. by resistively heating the top ITO slide. A power supply was attached through clips on opposite ends of the slide. Current flowed through the ITO surface causing heating. In order to monitor temperature, a thermocouple is inserted in a temperature sensing fluid well on the slide.

Model Bacterial Strains. Three model strains of Staphylococcus aureus from the American Type Culture Collection (ATCC, Manassas, Va.) were used in this experiment. The ATCC 29213 strain is a control strain known susceptible to both clindamycin and erythromycin. The BAA-976 strain is resistant to erythromycin but susceptible to clindamycin. The BAA-977 strain is the model MLS$_B$i organism. The known susceptibilities of the three organisms, including inducibility, was confirmed experimentally in our lab using standard D-Test procedures.

Induction Assay. The induction assay was performed in an identical manner each organism. The steps were as follows. Stock bacterial tryptic soy broth solutions were centrifuged to pellet organisms. The pellet was resuspended in 1 mM histidine as a wash step and then re-pelleted. This pellet was then resuspended in electrokinetic concentration (EKC) buffer. The EKC buffer was an aqueous solution containing 1 mM histidine, 10 mM hydroquinone, and 40 mM DTT at pH 6.8. Resuspension was to an estimated organism concentration of 1E+07 CFU/ml. The bacteria/EKC buffer suspension was then pumped into the microfluidic flow cell. One microscope field of view in the flow cell, 0.593×0.444 mm, was monitored throughout the entire experiment. The pump was stopped once the flow cell was full. At that point, the power to the ITO electrodes was turned on, and electrokinetic concentration proceeded for 5 minutes at 1.6 V. At the end of 5 minutes, essentially all organisms migrated to the affinity surface (BSA-PLL) where they bound to the surface, and the power to the electrodes was turned off.

Following EKC, the flow cell was washed by pumping approximately 1 ml histidine buffer through the system. This removed any loosely bound organisms, and more importantly flushed out the EKC buffer. The histidine wash was then followed by a tryptic soy broth growth medium flush. Once the immobilized organisms were exposed to growth medium, the flow was stopped and the organisms were allowed to grow on the surface for one hour. At that point, the induction step was started. The flow cell was filled with 0.07 ug/ml erythromycin in growth medium and was allowed to incubate for one hour. This is defined as the induction period. Following induction, the flow cell was exchanged with 8 ug/ml clindamycin admixed with 0.07 ug/ml erythromycin in growth medium. Note that the susceptibility break point for S. aureus for both of these antibiotics is 0.5 ug/ml. So in this assay, the induction concentration is well below MIC, while the susceptibility test is at a concentration well above MIC. Organisms were allowed to grow for 4 hours under these conditions. This was defined as the susceptibility test period and is also called the kill phase. We note again that the microscope field of view remains fixed during the entire process, from sample introduction through the final treatments with antibiotics, allowing real-time monitoring of all individual organisms in the field.

This process was run on the three model organisms described above. In a separate experiment, the BAA-977 MLS$_B$i strain was also run without the induction step.

Results. FIG. 14 shows growth profiles for the BM-977 and BAA-976 strains during the susceptibility test period. The curve marked BM-977 Induced clearly shows that after induction with low concentration erythromycin, the organism grows in the presence of >MIC clindamycin. The organism is showing induced resistance. The apparent decrease in bacterial counts at the 240-minute time point is an artifact of the measurement system. At 240 minutes, the S aureus surface concentration has grown beyond what is countable with the current image analysis software.

The BAA-976 control strain shows no growth on under the same conditions. This is expected, as the BAA-976 is known susceptible to clindamycin.

The BM-977 "Clindamycin Only" curve is an important demonstration. The lack of growth shown in that curve shows that in the absence of the erythromycin induction, the BAA-977 strain appears susceptible to clindamycin. This is an incorrect diagnosis of the MLS$_B$i strain. The ATCC 29213 strain, known susceptible to both antibiotics, showed no growth in this assay (data not shown).

Results in FIG. 13 show that statistically significant evidence of induced resistance can be found within two hours of introduction of clindamycin to the flow cell. The entire cycle time of this assay after the introduction of the bacterial sample to the cassette was less than 4 hours. This is a dramatic improvement over the current D-Test method, which requires an overnight growth of plated organisms.

It is understood that these examples in no way serve to limit the true scope of this invention, but rather are presented for illustrative purposes. There are numerous specific mathematical formulae that will match, to one extent or another, phenomena of this sort.

The methods and devices of the present invention have been described primarily with respect to the identification and AOA susceptibility of microorganisms. However, as mentioned earlier in this specification, it is also possible to use the methods of the present invention with respect to other veterinary or medically important conditions than bacterial infection. For example, in order to test the efficacy of antiviral drugs on a patient with a viral infection, suitable host cells (which depending on the nature of the infection, can be collected from the patient, or alternatively from host cells cultured for the task) can be collected on a surface, and then exposed to samples of the virus from the patient. In each channel, different antiviral agents, at possibly different concentrations, can be placed into the system, and the progress of the viral infection observed. Such observation can include antibody reactivity with cellular markers of infection, with biomarkers associated directly with viruses, with change in cellular physiology (e.g. rates of respiration), with rates of cell division, with patterns of cell division (e.g. cells growing outside of a monolayer), or with changes in cell structure observable by microscopy (possibly in conjunction with stains).

The use of the system with respect to anti-tumor/anti-cancer agents can involve the use of cancer cells obtained from a patient in a biopsy or blood sample. If the cells are taken from a solid tumor, the cells can be dispersed by mechanical and/or enzymatic means (e.g. protease treatment). At this point, the cells can be introduced into the system in the manner of microorganisms, with electrokinetic concentration used if necessary to bring the cells to the surface for attachment. At this point, anti-cancer agents can be introduced, and changes in the cancer cells, either death, cessation of cell division, or changes in cellular morphology can be observed and measured. This form of analysis can be used not only to gauge the effect of anticancer agents on cancer cells, but also to determine the toxicity of these agents to non-cancer cells, should the toxicity be highly variable among people.

In a similar way, the system can be used to gauge the presence or lack of side effects of a beneficial drug, by taking samples of patient cells, and challenging them with the drugs to gauge the appearance of the side effects by microscopic examination of the cells, whether by morphology, growth characteristics, or by staining with biochemicals that reflect the physiology of the cells, or by staining with antibodies or similar stains that indicate the presence or levels of various biomarkers.

Numerous and varied other arrangements can be readily devised by those skilled in the art without departing from the spirit and scope of the invention. Moreover, all statements herein reciting principles, aspects and embodiments of the present invention, as well as specific examples thereof, are intended to encompass both structural and functional equivalents thereof. Additionally, it is intended that such equivalents include both currently known equivalents as well as equivalents developed in the future, i.e. any elements developed that perform the same function, regardless of structure. All references cited herein are incorporated by reference.

We claim:

1. A method for measuring the growth of a plurality of individual microorganisms in a sample comprising:
   contacting said sample with a biosensor comprising:
      a chamber having at least one detection surface configured to bind a plurality of said microorganisms wherein each said individual microorganism binds to said detection surface in spatially discrete sites;
      an input port configured to transport a solution into the chamber; and
      an output port configured to transport said solution out of said chamber;
   allowing said individual microorganisms to grow on said detection surface for a first period of time; and
   detecting growth of individual microorganisms on said detection surface as an indication of the presence of said microorganisms.

2. The method according to claim 1 wherein said allowing step comprises adding at least one bioactive agent to said chamber.

3. The method according to claim 1 wherein a plurality of bioactive agents are added to the chamber.

4. The method according to claim 2 wherein said agent(s) are added after a first growth period.

5. The method according to claim 3 wherein said agent(s) are added after a first growth period.

6. The method according to claim 2 further comprising measuring growth of said individual microorganisms prior to said addition of said agent(s); and measuring growth of said individual microorganisms after a second growth period in the presence of said agent(s).

7. The method according to claim 3 further comprising measuring growth of said individual microorganisms prior to said addition of said agent(s); and measuring growth of said individual microorganisms after a second growth period in the presence of said agent(s).

* * * * *